US009676715B2

(12) United States Patent
Denis et al.

(10) Patent No.: US 9,676,715 B2
(45) Date of Patent: Jun. 13, 2017

(54) BIS-INDOLIC DERIVATIVES, A PROCESS FOR PREPARING THE SAME AND THEIR USES AS A DRUG

(75) Inventors: Jean-Noël Denis, Jarrie (FR); Marcelle Claude Jolivalt, Sceaux (FR); Louis Maurin Max Maurin, Meylan (FR); Matthieu Jeanty, Louviers (FR)

(73) Assignee: UNIVERSITE JOSEPH FOURIER, Grenoble (FR)

( * ) Notice: Subject to any disclaimer, the term of this patent is extended or adjusted under 35 U.S.C. 154(b) by 0 days.

(21) Appl. No.: 14/234,251

(22) PCT Filed: Jul. 20, 2012

(86) PCT No.: PCT/EP2012/064337
§ 371 (c)(1),
(2), (4) Date: Apr. 17, 2014

(87) PCT Pub. No.: WO2013/014102
PCT Pub. Date: Jan. 31, 2013

(65) Prior Publication Data
US 2014/0309272 A1    Oct. 16, 2014

(30) Foreign Application Priority Data

Jul. 22, 2011  (EP) .................................... 11305963

(51) Int. Cl.
*C07D 209/42*  (2006.01)
*A61K 31/4045*  (2006.01)

(52) U.S. Cl.
CPC ........ *C07D 209/42* (2013.01); *A61K 31/4045* (2013.01)

(58) Field of Classification Search
None
See application file for complete search history.

(56) References Cited

U.S. PATENT DOCUMENTS

2010/0029598 A1*  2/2010  Kopitz ................ C07D 209/42
                                                    514/165
2010/0144726 A1  6/2010  Denis et al.

FOREIGN PATENT DOCUMENTS

WO    WO2008152099    * 12/2008

OTHER PUBLICATIONS

Chemical abstract registry No. 920456-32-2, indexed in the Registry File on STN CAS Online Feb. 11, 2007.*
CAPLUS printout of Shea et al., Growth of carrot cell suspension cultures in medium containing amino acid conjugates of indoleacetic acid. Journal of Plant Physiology, 1988, 132, 298-302.*
Ito et al., A medium-term rat livery bioassay for rapid in vivo detection of carcinogenic potentical of chemical. Cancer Science, 2003, 94, 3-8.*
CAPLUS printout of Foreign Patent No. CN1453275.*
Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Wang et al., One-Pot Synthesis of 2-Amino-indole-3-carboxamide and Analogous. ACS Combinatorial Science, 2011, 13, 140-146.*
International Search Report, Dated Sep. 11, 2012, in PCT/EP2012/064337.

* cited by examiner

*Primary Examiner* — Matthew Coughlin
*Assistant Examiner* — Po-Chih Chen
(74) *Attorney, Agent, or Firm* — Young & Thompson

(57) ABSTRACT

Novel bis-indolic derivatives, processes for their preparation, and their potential use as new antibacterial drugs.

3 Claims, 2 Drawing Sheets

BIS-INDOLIC DERIVATIVES, A PROCESS FOR PREPARING THE SAME AND THEIR USES AS A DRUG

The present invention relates to novel bis-indolic derivatives, processes for their preparation, and their potential use as new antibacterial drugs.

Penicillin G was the first natural antibiotic identified, first by Ernst Duchesne in the 19th century, then rediscovered in 1928 by Alexander Fleming.

Sulfonamides, synthetic antibiotics, have emerged at the same time as penicillin G. Prontosil was the first compound of this class to be synthesized in 1932 by Gerhard Domagk. However, the sulfamidotherapy only began after J. and T H. Trefouël, F. Nitti and D. Bovet discovered in 1935 that prontosil was metabolized in the active compound sulfanilamide.

Most of the major classes of natural antibiotics have been isolated and characterized between 1940 and 1960. The quinolones, synthetic antibiotics, were introduced in 1962. Then, it was only 40 years later, in 2000, that a novel class of synthetic antibiotics was discovered: the oxazolidinone class.

Despite the discovery of numerous active compounds, their medical interest has been more or less quickly reduced because of development of bacterial resistances. Resistance mechanisms include the inactivation of the drug by specific enzymes, alteration of the antibiotic target, bacterial wall impermeability to antibiotic entry, and efflux of the antibiotic from the bacterial cytosol. These mechanisms usually develop within a few years after a new drug is introduced into clinical practice.

To overcome the problem of antibiotic resistance, three ways can be considered:
1) structural modifications of existing drugs to obtain new compounds with maintained activity in the presence of known resistance mechanisms
2) restoration of the activity of existing antibiotics by combining a compound that inhibits bacterial resistance mechanisms, and
3) development of novel antibiotic classes with original chemical structures and modes of action, as to avoid the deleterious effect of previously selected antibiotic resistance mechanisms, these new antibiotics will thus be effective against major antibiotic-resistant human pathogens.

As an example, *Staphylococcus aureus* (a major human pathogen) may resist to antibiotics by the production of enzymes (e.g., penicillinase leading to resistance to penicillin G, transferases leading to resistance to aminoglycosides), by the modification of natural targets (e.g., acquisition of mecA gene in methicillin-resistant strains), or by efflux systems (e.g., NorA and fluoroquinolone resistance).

Because the dramatic increase in antibiotic resistances became a public health problem, the pharmaceutical industry relaunched at the beginning of the 1990's the research on antibacterial compounds. This led to the linezolide success (Y. Van Laethem, J. Sternon *Rev. Med. Brux.* 2004, 25, 47-50), oxazolidinones development by Pfizer, and daptomycin development by Novartis (F. P. Tally, M. F. DeBruin, <<Development of daptomycin for Gram-positive infections>>, *Journal of Antimicrobial Chemotherapy,* 2000, 46, 523-526; L. Robbel, M. A. Marahiel <<Daptomycin, a bacterial lipopeptide synthesized by a nonribosomal machinery>> *J. Biol. Chem.* 2010, 285, 27501-27508).

Since 2000, oxazolidinones and cyclic lipopeptides have been the two only new antibiotic classes with a complete original structure approved in the treatment of Gram-positive bacterial infections. Linezolide and daptomycin are the only commercialized compounds of the oxazolidinone and lipopeptide classes, respectively. Their antibacterial spectrum comprises most of Gram-positive bacteria responsible for human infections, including multi-drug resistant strains such as the vancomycin-resistant *Enterococcus* sp. (VRE) and methicillin-resistant *Staphylococcus aureus* (MRSA).

Other new antibiotics with a known structural moiety have been recently commercialized or are currently under development (V. Cattoir, C. Daurel, <<Médecine et Maladies infectieuses>>, 2010, 40, 135-154) such as tigecycline, first glycylcycline that is a new class of hemi synthetic antibiotics derived from the tetracycline family (L. R. Peterson, <<A review of tigecycline—the first glycylcyline>>, *Int. J. Antimicrob. Agents,* 2008, 32, S215-222). Tigecycline has a broad antibacterial spectrum comprising aerobic or anaerobic, Gram-positive or Gram-negative bacteria.

Among β-lactams, new carbapenems have been developed. They have a broad antibacterial spectrum because of greater stability to the action of most β-lactamases. Three carbapenems are currently commercialized: imipenem, meropenem and ertapenem. A fourth one, doripenem, is close to the commercialization (M. Wolff, M.-L. Joly-Guillou, O. Pajot, <<Les carbapénèmes>>, *Réanimation,* 2009, 18, 5199-5208). Their antibacterial spectrum encompasses most of aerobic and anaerobic bacteria. However, they are not effective against multi-drug resistant bacteria such as MRSA, methicillin-resistant coagulase-negative staphylococci, penicillin-resistant *E. faecium*, carbapenemase-producing Enterobacteraceae or *Pseudomonas aeruginosa*, and *Stenotrophomonas maltophilia*.

Two new cephalosporins (ceftobiprole and ceftaroline) with a broad antibacterial spectrum and an activity against MRSA are currently in phase III clinical trial.

Pharmacokinetic parameters of vancomycin (lead of glycopeptides) and its relative toxicity have always been a hindrance to its intensive clinical use. Many endeavors have been accomplished to optimize its structure and this work has recently led to the development of the lipopeptides. Structurally close to the glycopeptide family, these compounds have a lipophilic chain added to the glycopeptide moiety (M. T. Guskey, B. T. Tsuji, <<A comparative review of the lipoglycopeptides: oritavancin, dalbavancin, and telavancin>>, *Pharmacotherapy* 2010, 30, 80-94). Among these three compounds, telavancin is the only compound to be commercialized, the two others being still in phase II clinical trials.

All these new compounds, except oxazolidinones and lipopeptides, present a structure derived from a molecule with a biosynthetized active moiety. This may facilitate rapid development by bacteria of resistance mechanisms to these new compounds. In addition, most of these new molecules have very complex structures, leading the big pharmaceutical company to hesitate to invest in this medicinal domain because the earning potential is unpredictable and could be even null in case of a fast apparition of resistance.

There is thus an urgent need to develop new compounds that may help solving the problem of bacterial resistance to currently available antibiotics. This may be obtained by developing new classes of antibacterial agents with original structures and modes of action, and thus able to maintain their activity against microorganisms harboring known resistance mechanisms. Ideally, the newer compounds may prevent or delay the emergence of new resistance mechanisms leading to their inactivation. Another solution will consist in developing molecules liable to block existing bacterial resistance mechanisms, in order to restore the activity of currently available antibiotics.

Recently, a new class of molecules showing antimicrobial activity named indole derivatives has been disclosed in the international application WO 2008110690. However, the minimum inhibitory concentrations (MIC) obtained for various bacterial species, especially multi-drug resistant bacteria, are relatively high.

One objective of the present invention is to provide new compounds, with new structures, and an improved antibacterial activity as compared to monoindole derivatives, including against bacteria resistant to multiple antibiotics.

Another aim of the invention is to provide new compounds with an original structure liable to inhibit the NorA efflux pump of *Staphylococcus aureus*, responsible for fluoroquinolone resistance in this species.

Another aim of the invention is to provide new compounds having both an antibiotic activity when used alone or in association with fluoroquinolones, and a NorA efflux pump inhibition activity.

Still another aim is to provide pharmaceutical compositions comprising said new compounds.

The present invention relates to a compound of the following formula I:

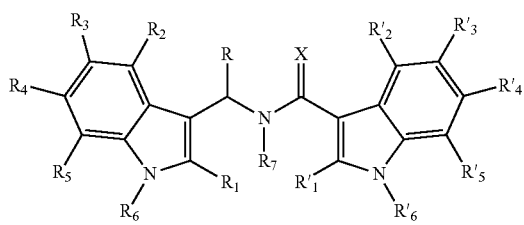

I wherein:
X represents O or S,
$R_1$, $R_2$, $R_3$, $R_4$, $R_5$, $R'_1$, $R'_2$, $R'_3$, $R'_4$ and $R'_5$ represent independently from each other:
H,
a linear or branched $(C_1-C_7)$alkyl, if appropriate substituted by:
  a halogen, a hydroxyl group, a $OR_a$ or $NR_aR_b$, wherein $R_a$ and $R_b$ represent:
    H, a linear or branched $(C_1-C_7)$-alkyl, a $(C_3-C_7)$-cycloalkyl, an aryl substituted or not, $CH_2$-aryl, CO—$(C_1-C_7)$-alkyl, CO-aryl, $CO_2$—$(C_1-C_7)$-alkyl, $CO_2$-aryl, wherein aryl is a substituted or not aromatic group or a substituted or not heteroaromatic group
  a $(C_3-C_7)$-cycloalkyl, an aryl substituted or not, $CH_2$-aryl, CO—$(C_1-C_7)$-alkyl, CO-aryl, $CO_2$—$(C_1-C_7)$-alkyl, $CO_2$-aryl, wherein aryl is a substituted or not aromatic group or a substituted or not heteroaromatic group,
  F, Cl, Br, I, $CF_3$, OH, $OCF_3$, $COCF_3$, $OR_a$, $NH_2$, $NHR_a$, $NR_aR_b$, wherein $R_a$ and $R_b$ represent:
    H, a linear or branched $(C_1-C_7)$-alkyl, a $(C_3-C_7)$-cycloalkyl, an aryl substituted or not, $CH_2$-aryl, CO—$(C_1-C_7)$-alkyl, CO-aryl, $CO_2$—$(C_1-C_7)$-alkyl, $CO_2$-aryl, wherein aryl is a substituted or not aromatic group or a substituted or not heteroaromatic group,
  CN and $NO_2$ provided that $R_1$, $R_2$, $R_3$, $R_4$, $R_5$, $R'_1$ are different from CN and $NO_2$.
R represents H, a $(C_1-C_7)$-alkyl, $CH_2NHCO_2$—$(C_1-C_7)$-alkyl, $CH_2NHCO_2$—$(C_3-C_7)$-cycloalkyl, $CO_2H$, $CO_2$—$(C_1-C_7)$-alkyl, $CO_2$—$(C_3-C_7)$-cycloalkyl, $(CH_2)_nOH$, $CH_2NH(CH_2)_n$—OH, $CH_2NH(CH_2)_n$—$NR_aR_b$, CONH—$(C_1-C_7)$-alkyl, CONH—$(C_3-C_7)$-cycloalkyl, CONH-aryl, CONH—$(CH_2)_nOH$, CONH—$(CH_2)_nNR_aR_b$, wherein n=2 to 12 and $R_a$, $R_b$, aryl and alkyl being as defined above.

$R_6$ and $R'_6$ represent independently from each other H, $(C_1-C_7)$-alkyl, $SO_2$aryl, wherein aryl being as defined above, OH, O—$(C_1-C_7)$-alkyl, CO—$(C_1-C_7)$-alkyl, CO-aryl, $CH_2NH_2$, $CH_2NHR_a$, $CH_2NR_aR_b$, $Si(R_c)_3$, the Rc groups being identical or different and representing independently of each other a linear or branched $(C_1-C_7)$-alkyl, a $(C_3-C_7)$-cycloalkyl, or an aryl, aryl and alkyl being as defined above,
$R_7$ represent H, OH, $OR_a$, $R_a$ being as defined above.
and their pharmaceutically acceptable salts,
for use as a medicament, suitable especially for an antibacterial activity and/or NorA efflux pump inhibition.

By linear alkyl group from $C_1$ to $C_7$ is meant a group such as methyl, ethyl, propyl, butyl, pentyl, hexyl or heptyl.

By branched alkyl group is meant an alkyl group as defined above bearing substituents selected from the list of linear alkyl groups defined above, said linear alkyl group being also liable to be branched.

Both linear and branched alkyl definitions apply to the entire specification.

By cycloalkyl group from $C_3$ to $C_7$ is meant a group such as cyclopropyl, cyclobutyl, cyclopentyl, cyclohexyl or cycloheptyl. Such groups can also be substituted by a linear or branched alkyl group as defined above.

The definition of cycloalkyl group applies also to the entire specification.

The term "aryl" refers to any functional group or substituent derived from a simple aromatic ring.

The aryl can be substituted by one or more groups chosen independently among an halogen, a linear or branched $(C_1-C_7)$-alkyl, a $(C_3-C_7)$-cycloalkyl, CN, $CF_3$, OH, $OR_x$, $NH_2$, $NHR_x$, $NR_xR_y$, $R_x$ and $R_y$ being a linear or branched $(C_1-C_7)$-alkyl, a $(C_3-C_7)$-cycloalkyl, an aryl substituted or not, $CH_2$-aryl, CO—$(C_1-C_7)$-alkyl or cycloalkyl, CO-aryl, $CO_2H$, $CO_2$—$(C_1-C_7)$-alkyl or cycloalkyl, The term "heteroaromatic" refers to a compound having the characteristics of an aromatic compound whilst having at least one non-carbon atom in the ring.

The heteroaromatic can be substituted by one or more groups chosen independently among those defined for aryl.

A basic group such as the nitrogen of the indole moiety or an amino group present on the molecule can be under a salt form, the salt being any pharmaceutically acceptable salt obtained by reaction of an inorganic acid, an organic acid or a halogenoalkyl, on an amino group to give a quaternary ammonium.

Examples of inorganic acid allowing obtaining pharmaceutically acceptable salts include, without being limited to them, hydrochloric acid, hydrobromic acid, hydroiodic acid, nitric acid, carbonic acid, formic acid, monohydrogenocarbonic acid, phosphoric acid, monohydrogenophosphoric acid, dihydrogenophosphoric acid, perchloric acid, sulfuric acid, monohydrogenosulfuric acid.

Examples of organic acid allowing to obtain pharmaceutically acceptable salts include, without being limited to them, acetic acid, lactic acid, propionic acid, butyric acid, isobutyric acid, palmitic acid, malic acid, glutamic acid, hydroxymalic acid, malonic acid, benzoic acid, succinic acid, glycolic acid, suberic acid, fumaric acid, mandelic acid, phthalic acid, salicylic acid, benzenesulfonic acid, p-tolylsulfonic acid, citric acid, tartaric acid, methanesulfonic acid, hydroxynaphthoic acid.

As the molecule can also bear an acid group, and as at least one substituent of the indole moiety or of the aryl or heteroaromatic groups can be a phenol, they can also be under a pharmaceutically acceptable salt form.

The salt can be obtained with organic or mineral bases, to give for instance alkali metal salts such as, lithium, sodium, potassium salts.

As an example, see Berge et al, "Pharmaceutical Salts", *Journal of Pharmaceutical Science,* 1977, 66, 1-19.

When R is different from H, the molecule present an asymmetric carbon and thus compounds of the invention can be the R or the S enantiomer, a racemic mixture of both enantiomers or a mixture comprising 0.01%-99.99% of the R enantiomer and 99.99%-0.01% of the S enantiomer.

The inventors have found that some compounds bearing two indole moieties, present an antibiotic activity on bacteria, and said compounds presenting an original structure with regards to all existing antibiotics; they are promising candidate not to develop a resistance or to develop only late resistance.

The finding of the inventors is that compounds lacking the indole moiety borne by the carbonyl group of the amide function lose completely the antibiotic activity (see comparative examples).

The inventors have also found that some compounds are NorA efflux pump inhibitor and thus could be used in association with known antibiotics allowing reversing the antibiotic resistance toward said antibiotics.

Further, compounds of the invention present also both intrinsic antibacterial activity and NorA efflux pump inhibitor activity.

In an advantageous embodiment, the present invention relates to compounds of formula I defined above, wherein the antibacterial activity is against Gram-positive and Gram-negative bacteria.

Another advantage of the invention is to provide antibiotics active both against Gram-positive and Gram-negative bacteria.

The term "Gram-positive bacteria" refers to the two bacterial phyla defined in the Bergey's manual of systematic bacteriology ($2^{nd}$ edition, G. M. Garrity (ed.), Springer, 2005), Actinobacteria, and Firmicutes, and include the well known genera *Staphylococcus, Streptococcus; Enterococcus, Listeria* and *Bacillus,*

The term "Gram-negative bacteria" refers to 22 bacterial phyla defined in the Bergey's manual of systematic bacteriology ($2^{nd}$ edition, G. M. Garrity, Springer, 2005), Aquificae, Thermotogae, Thermodesulfobacteria, Deinococcus-Thermus, Chrysiogenetes, Chloroflexi, Thermomicrobia, Nitrospira, Deferribacteres, Cyanobacteria, Chlorobia, Proteobacteria, Planctomycetes, Chlamydiae, Spirochaetes, Fibrobacteres, Acidobacteres, Bacteroidetes, Fusobacteria, Verrucomicrobia, Dictyoglomi, and Gemmatimonadetes.

Proteobacteria, in particular, include a large number of human pathogens such as the Enterobacteriaceae, Pseudomonadaceae, Vibrionaceae, Moraxellaceae, Neisseriaceae and Pasteurellaceae families.

In an advantageous embodiment, the present invention relates to compounds of formula I defined above, wherein said compounds are narrow spectrum antibiotics having the advantage not to alter the intestinal microbiota.

By the expression "narrow-spectrum" it must be understood that compounds of the invention are able to act as an antibiotic effective against only specific families of bacteria (in the invention Gram-positive *Staphylococcus aureus* and coagulase-negative *Staphylococcus* species, and to a lesser extent Gram-positive *Streptococcus* and *Bacillus* species and Gram-negative *Haemophilus* species).

This is in contrast to a broad-spectrum antibiotic which is effective against a wide range of disease-causing bacteria.

In an advantageous embodiment, the present invention relates to compounds of formula I defined above, wherein said bacteria are resistant to conventional antibiotics, Compounds of the invention are not only active against sensitive bacteria but also present the advantage to be active against bacteria resistant to currently available antibiotics.

In an advantageous embodiment, the present invention relates to compounds of formula I defined above, wherein the antibacterial activity is against *Staphylococcus* species, in particular *Staphylococcus aureus*, especially *Staphylococcus aureus* resistant to β-lactams (including methicillin-resistant strains, also referred as MRSA), *Staphylococcus aureus* resistant to glycopeptides (vancomycin-resistant or glycopeptides-resistant strains, also referred as VISA or GISA) and *Staphylococcus aureus* resistant to fluoroquinolones.

Compounds of the invention are also active against coagulase-negative *Staphylococcus* species such as *Staphylococcus epidermidis*, including strains resistant to β-lactam or fluoroquinolone antibiotics.

Compounds of the invention also present the advantage to be active against bacteria that are multi-resistant, i.e., resistant to several classes of antibiotics including those cited above.

In an advantageous embodiment, the present invention relates to compounds of formula I defined above, having further an antifungal and/or antiviral activity.

A further advantage of the compounds of the invention is that they present not only an antibacterial activity but also an antifungal activity or an antiviral activity. Some of the compounds also present the triple activity.

In an advantageous embodiment, the present invention relates to compounds of formula I defined above, having the following formula II:

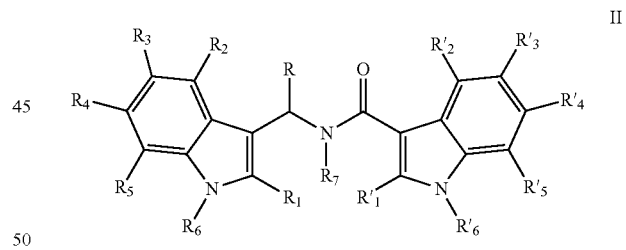

wherein $R_1$, $R_2$, $R_3$, $R_4$, $R_5$, $R_6$, $R_7$, $R'_1$, $R'_2$, $R'_3$, $R'_4$, $R'_5$, $R'_6$ and R are as defined above.

In an advantageous embodiment, the present invention relates to compounds of formula I or II defined above, wherein $R_6$ and $R'_6$ represent H.

In an advantageous embodiment, the present invention relates to compounds of formula I or II defined above, wherein $R_2$, $R_5$, $R'_2$ and $R'_5$ represent H.

In an advantageous embodiment, the present invention relates to compounds of formula I or II defined above, wherein $R_7$ represent H.

In an advantageous embodiment, the present invention relates to compounds of formula I or II defined above, wherein $R_6$ and $R'_6$ are different.

In an advantageous embodiment, the present invention relates to compounds of formula I or II defined above, wherein $R_1$ is different from $R'_1$, and/or $R_2$ is different from $R'_2$, and/or $R_3$ is different from $R'_3$, and/or $R_4$ is different from $R'_4$, and/or $R_5$ is different from $R'_5$.

In an advantageous embodiment, the present invention relates to compounds of formula I or II defined above, wherein $R_1$ is similar to $R'_1$, and/or $R_2$ is similar to $R'_2$, and/or $R_3$ is similar to $R'_3$, and/or $R_4$ is similar to $R'_4$, and/or $R_5$ is similar to $R'_5$ and/or $R_6$ is similar to $R'_6$.

In an advantageous embodiment, the present invention relates to compounds of formula I or II defined above, having the following formula III:

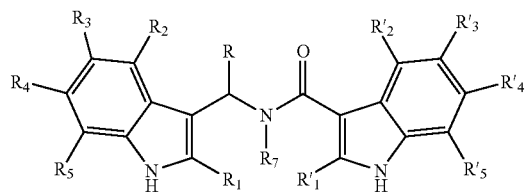

III wherein $R_1$, $R_2$, $R_3$, $R_4$, $R_5$, $R_7$, $R'_1$, $R'_2$, $R'_3$, $R'_4$, $R'_5$ and R are as defined above.

In an advantageous embodiment, the present invention relates to compounds of formula I or II defined above, having the following formula IV:

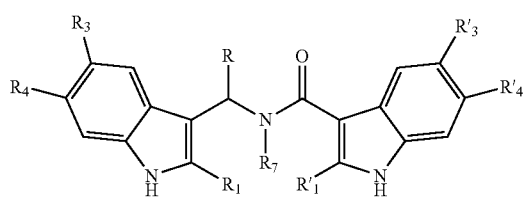

IV wherein $R_1$, $R_3$, $R_4$, $R_7$, $R'_1$, $R'_3$, $R'_4$ and R are as defined above.

In an advantageous embodiment, the present invention relates to compounds of formula I or II defined above, having the following formula V:

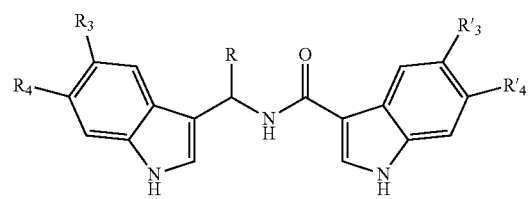

V wherein:
$R_3$, $R_4$, $R'_3$ and $R'_4$ represent independently from each other H, F, Cl, Br, I,
R represents a $(C_1-C_7)$-alkyl, $CH_2NHCO_2(C_1-C_7)$-alkyl, $(CH_2)_nOH$, $CH_2NH(CH_2)_n$—OH, $CH_2NH(CH_2)_n$—$NR_aR_b$, $CO_2H$, $CO_2$—$(C_1-C_7)$-alkyl, $CONH$—$(CH_2)_nOH$, $CONH$—$(CH_2)_nNR_aR_b$.

Preferably at least one halogen atom must be present in $R_3$, $R_4$, $R'_3$ or $R'_4$ position, more preferably two halogens atoms (one halogen atom on each indole cycle) must be present and more preferably said halogen is Br.

In an advantageous embodiment, the present invention relates to compounds of formula V defined above, having the following formula V-I:

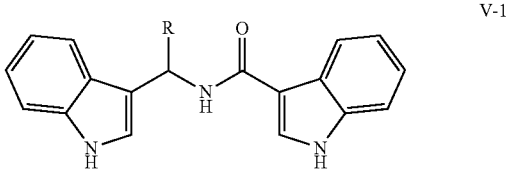

V-1 wherein:
R represents a $(C_1-C_7)$-alkyl, $CH_2NHCO_2(C_1-C_7)$-alkyl, $(CH_2)_nOH$, $CH_2NH(CH_2)_n$—OH, $CH_2NH(CH_2)_n$—$NR_aR_b$, $CO_2H$, $CO_2$—$(C_1-C_7)$-alkyl, $CONH$—$(CH_2)_nOH$, $CONH$—$(CH_2)_nNR_aR_b$.

It has been found by the inventors that compounds of formula V-1 bearing no halogen atom on the two indole moieties present no antibacterial activity but present a NorA efflux pump inhibitor activity.

One of the advantages of the compounds of the invention having a Nor A efflux pump inhibitor activity is the possibility of said compounds to reverse the resistance of a bacterial strain that became resistant to a classical antibiotic if they are administered with said classical antibiotic provided that classical antibiotic and compounds of the invention belong to different families of antibiotics.

In an advantageous embodiment, the present invention relates to compounds of formula V defined above, wherein at least one of $R_3$, $R_4$, $R'_3$ and $R'_4$ represents F, Cl, Br, I, and
R represents a $(C_1-C_7)$-alkyl, $CH_2NHCO_2(C_1-C_7)$-alkyl, $(CH_2)_nOH$, $CH_2NH(CH_2)_n$—OH, $CH_2NH(CH_2)_n$—$NR_aR_b$, $CO_2H$, $CO_2$—$(C_1-C_7)$-alkyl, $CONH$—$(CH_2)_nOH$, $CONH$—$(CH_2)_nNR_aR_b$.

It has been surprisingly found by the inventors that compounds of formula V bearing at least one halogen atom on at least one of the two indole moieties present an antibacterial activity.

For compounds presenting an antibacterial activity as compounds of formula V for instance, the determination of the NorA efflux pump inhibitor activity is possible only with specific techniques.

Therefore, such compounds present either intrinsic antibacterial activity or NorA efflux pump inhibitor activity or both activities.

In an advantageous embodiment, the present invention relates to compounds of formula V defined above, having the following formula V-2:

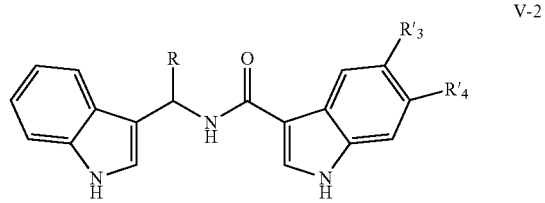

V-2 wherein at least one of $R'_3$ and $R'_4$ represents H, F, Cl, Br, I,
R represents a $(C_1-C_7)$-alkyl, $CH_2NHCO_2(C_1-C_7)$-alkyl, $(CH_2)_nOH$, $CH_2NH(CH_2)_n$—OH, $CH_2NH(CH_2)_n$—$NR_aR_b$, $CO_2H$, $CO_2$—$(C_1-C_7)$-alkyl, $CONH$—$(CH_2)_nOH$, $CONH$—$(CH_2)_nNR_aR_b$.

In an advantageous embodiment, the present invention relates to compounds of formula V defined above, having the following formula V-3:

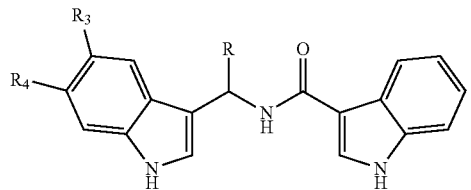

V-3 wherein at least one of $R_3$ and $R_4$ represents H, F, Cl, Br, I, R represents a ($C_1$-$C_7$)-alkyl, $CH_2NHCO_2$($C_1$-$C_7$)-alkyl, $(CH_2)_nOH$, $CH_2NH(CH_2)_n$—OH, $CH_2NH(CH_2)_n$—$NR_aR_b$, $CO_2H$, $CO_2$—($C_1$-$C_7$)-alkyl, $CONH$—$(CH_2)_nOH$, $CONH$—$(CH_2)_nNR_aR_b$.

In an advantageous embodiment, the present invention relates to compounds of one of the formula I to V defined above, having the following general formula VI:

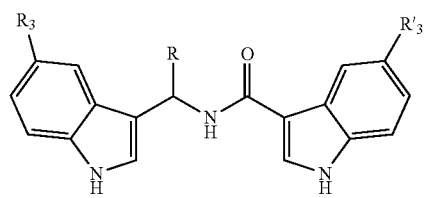

VI wherein:
$R_3$ and $R'_3$ represent independently from each other H, F, Cl, Br, I,
R represents a ($C_1$-$C_7$)-alkyl, $CH_2NHCO_2$($C_1$-$C_7$)-alkyl, $(CH_2)_nOH$, $CH_2NH(CH_2)_n$—OH, $CH_2NH(CH_2)_n$—$NR_aR_b$, $CO_2H$, $CO_2$—($C_1$-$C_7$)-alkyl, $CONH$—$(CH_2)_nOH$, $CONH$—$(CH_2)_nNR_aR_b$.

In an advantageous embodiment, the present invention relates to compounds of the formula VI defined above, wherein at least one of $R_3$ and $R'_3$ represents F, Cl, Br, I, R represents a ($C_1$-$C_7$)-alkyl, $CH_2NHCO_2$($C_1$-$C_7$)-alkyl, $(CH_2)_nOH$, $CH_2NH(CH_2)_n$—OH, $CH_2NH(CH_2)_n$—$NR_aR_b$, $CO_2H$, $CO_2$—($C_1$-$C_7$)-alkyl, $CONH$—$(CH_2)_nOH$, $CONH$—$(CH_2)_nNR_aR_b$.

In an advantageous embodiment, the present invention relates to compounds of the formula VI defined above, having the following general formula VI-1:

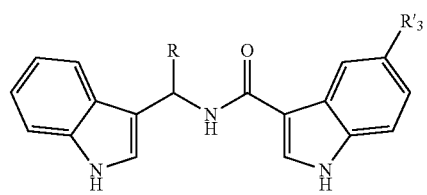

VI-1 wherein $R'_3$ represents F, Cl, Br, I,
R represents a ($C_1$-$C_7$)-alkyl, $CH_2NHCO_2$($C_1$-$C_7$)-alkyl, $(CH_2)_nOH$, $CH_2NH(CH_2)_n$—OH, $CH_2NH(CH_2)_n$—$NR_aR_b$, $CO_2H$, $CO_2$—($C_1$-$C_7$)-alkyl, $CONH$—$(CH_2)_nOH$, $CONH$—$(CH_2)_nNR_aR_b$.

In an advantageous embodiment, the present invention relates to compounds of the formula VI defined above, having the following general formula VI-2:

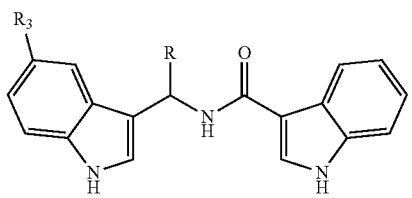

VI-2 wherein $R_3$ represents F, Cl, Br, I,
R represents a ($C_1$-$C_7$)-alkyl, $CH_2NHCO_2$($C_1$-$C_7$)-alkyl, $(CH_2)_nOH$, $CH_2NH(CH_2)_n$—OH, $CH_2NH(CH_2)_n$—$NR_aR_b$, $CO_2H$, $CO_2$—($C_1$-$C_7$)-alkyl, $CONH$—$(CH_2)_nOH$, $CONH$—$(CH_2)_nNR_aR_b$.

In an advantageous embodiment, the present invention relates to compounds of formula VI defined above, wherein the compound of formula VI is selected from the group consisting of:

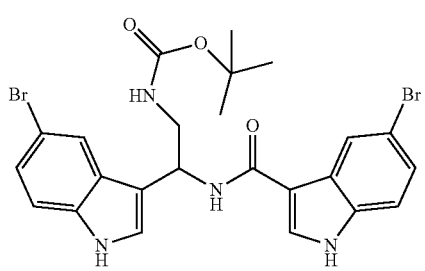

Compound 3f

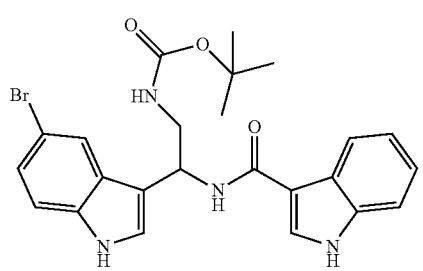

Compound 3b

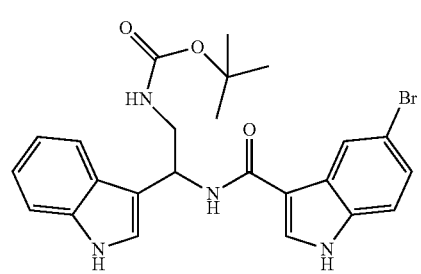

Compound 3c

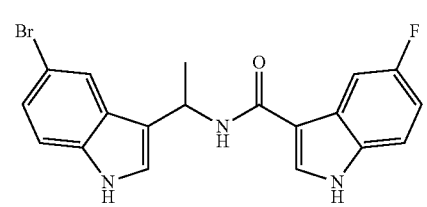

Compound 5

-continued

Compound 6a
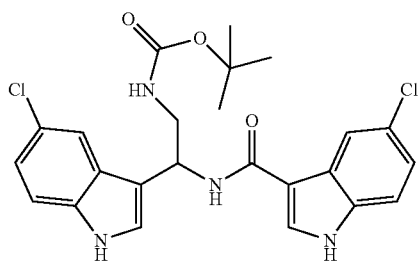

Compound 4
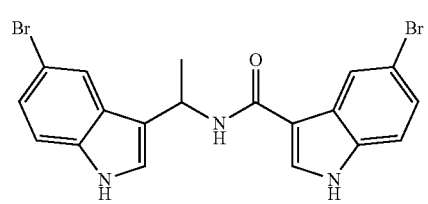

Compound 12
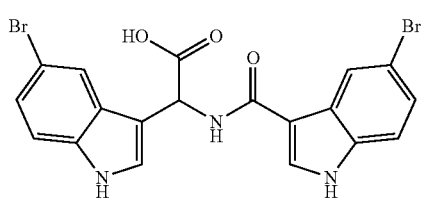

Compound 11
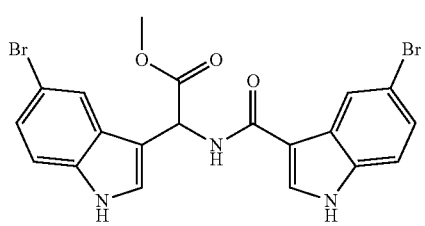

Compound 13
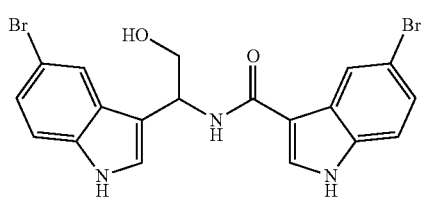

Compound 14
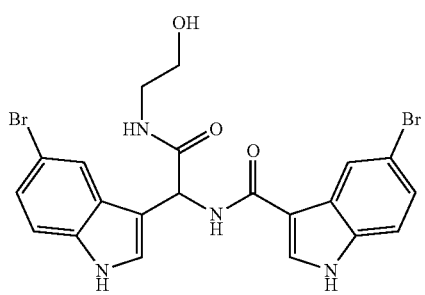

-continued

Compound 15
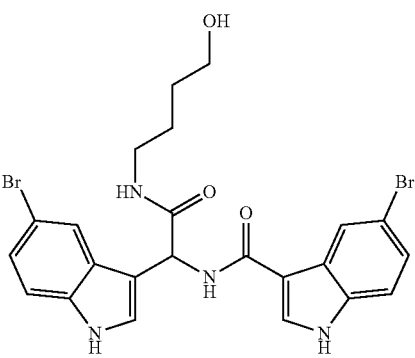

Compound 16
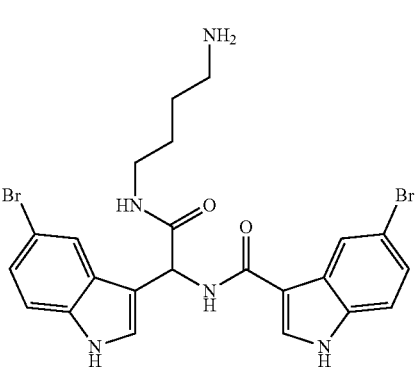

Said compounds present an antibacterial activity but also for compounds bearing an hydrophilic part in position R present a better solubility.

In an advantageous embodiment, the present invention relates to compounds of one of the formula I to V defined above, having the following general formula VII:

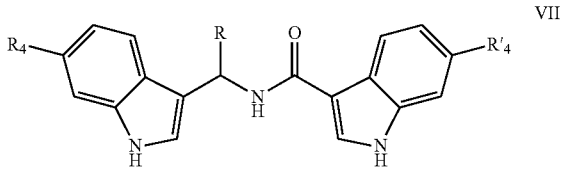

wherein:

$R_4$ and $R'_4$ represent independently from each other H, F, Cl, Br, I,

R represents a $(C_1-C_7)$-alkyl, $CH_2NHCO_2(C_1-C_7)$-alkyl, $(CH_2)_nOH$, $CH_2NH(CH_2)_n$—OH, $CH_2NH(CH_2)_n$—$NR_aR_b$, $CO_2H$, $CO_2$—$(C_1-C_7)$-alkyl, CONH—$(CH_2)_nOH$, CONH—$(CH_2)_nNR_aR_b$.

In an advantageous embodiment, the present invention relates to compounds of the formula VII defined above, wherein at least one of $R_4$ and $R'_4$ represents F, Cl, Br, I, R represents a $(C_1-C_7)$-alkyl, $CH_2NHCO_2(C_1-C_7)$-alkyl, $(CH_2)_nOH$, $CH_2NH(CH_2)_n$—OH, $CH_2NH(CH_2)_n$—$NR_aR_b$, $CO_2H$, $CO_2$—$(C_1-C_7)$-alkyl, CONH—$(CH_2)_nOH$, CONH—$(CH_2)_nNR_aR_b$.

In an advantageous embodiment, the present invention relates to compounds of the formula VII defined above, having the following general formula VII-1:

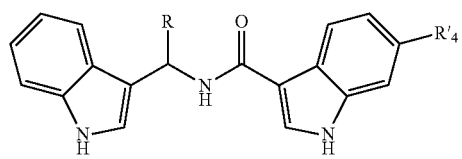

VII-1 wherein R'$_4$ represents F, Cl, Br, I,

R represents a (C$_1$-C$_7$)-alkyl, CH$_2$NHCO$_2$(C$_1$-C$_7$)-alkyl, (CH$_2$)$_n$OH, CH$_2$NH(CH$_2$)$_n$—OH, CH$_2$NH(CH$_2$)$_n$—NR$_a$R$_b$, CO$_2$H, CO$_2$—(C$_1$-C$_7$)-alkyl, CONH—(CH$_2$)$_n$OH, CONH—(CH$_2$)$_n$NR$_a$R$_b$.

In an advantageous embodiment, the present invention relates to compounds of the formula VII defined above, having the following general formula VII-2:

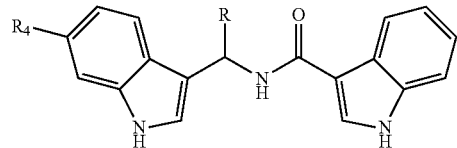

VII-2 wherein R$_4$ represents F, Cl, Br, I,

R represents a (C$_1$-C$_7$)-alkyl, CH$_2$NHCO$_2$(C$_1$-C$_7$)-alkyl, (CH$_2$)$_n$OH, CH$_2$NH(CH$_2$)$_n$—OH, CH$_2$NH(CH$_2$)$_n$—NR$_a$R$_b$, CO$_2$H, CO$_2$—(C$_1$-C$_7$)-alkyl, CONH—(CH$_2$)$_n$OH, CONH—(CH$_2$)$_n$NR$_a$R$_b$.

In an advantageous embodiment, the present invention relates to compounds of the formula VII defined above, wherein the compound of formula VII is selected from the group consisting of:

Compound 3i

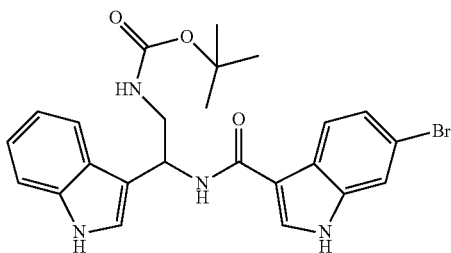

Compound 3d

Compound 3e

In an advantageous embodiment, the present invention relates to compounds of one of the formula I to V defined above, having the following general formula VIII:

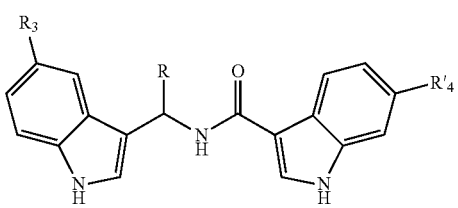

VIII wherein:
R$_3$ and R'$_4$ represent independently from each other F, Cl, Br, I,
R represents a (C$_1$-C$_7$)-alkyl, CH$_2$NHCO$_2$(C$_1$-C$_7$)-alkyl, CO$_2$H, (CH$_2$)$_n$OH, CH$_2$NH(CH$_2$)$_n$—OH, CH$_2$NH(CH$_2$)$_n$—NR$_a$R$_b$, CO$_2$—(C$_1$-C$_7$)-alkyl, CONH—(CH$_2$)$_n$OH, CONH—(CH$_2$)$_n$NR$_a$R$_b$.

In an advantageous embodiment, the present invention relates to compounds of the formula VIII defined above, having the following structure:

Compound 3g

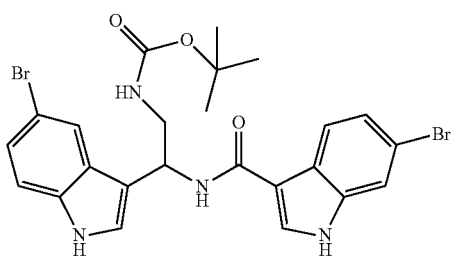

Compound 6b

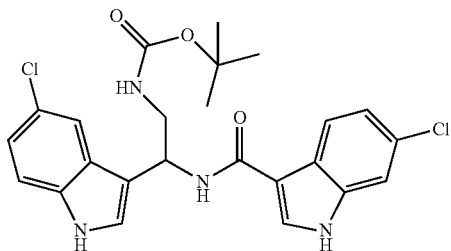

In an advantageous embodiment, the present invention relates to compounds of one of the formula I to V defined above, having the following general formula IX:

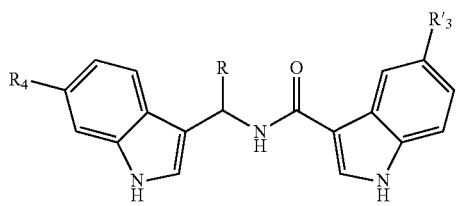

IX wherein:
$R_4$ and $R'_3$ represent independently from each other F, Cl, Br, I,
R represents a $(C_1-C_7)$-alkyl, $CH_2NHCO_2(C_1-C_7)$-alkyl, $CO_2H$, $(CH_2)_nOH$, $CH_2NH(CH_2)_n$—OH, $CH_2NH(CH_2)_n$—$NR_aR_b$, $CO_2$—$(C_1-C_7)$-alkyl, CONH—$(CH_2)_nOH$, CONH—$(CH_2)_nNR_aR_b$.

In an advantageous embodiment, the present invention relates to compounds of formula IX defined above, having the following structure:

Compound 3h

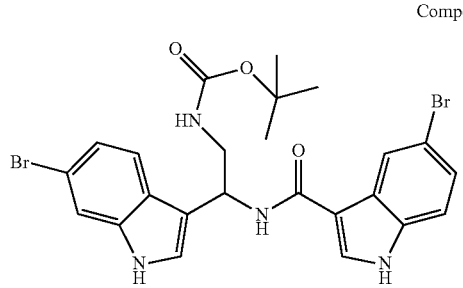

In an advantageous embodiment, the present invention relates to compounds of one of the formula I to V defined above, having the following general formula X:

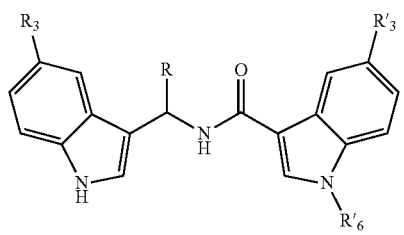

X wherein:
$R_3$ and $R'_3$ represent independently from each other F, Cl, Br, I,
R represents a $(C_1-C_7)$-alkyl, $CH_2NHCO_2(C_1-C_7)$-alkyl, $(CH_2)_nOH$, $CH_2NH(CH_2)_n$—OH, $CH_2NH(CH_2)_n$—$NR_aR_b$, $CO_2H$, $CO_2$—$(C_1-C_7)$-alkyl, CONH—$(CH_2)_nOH$, CONH—$(CH_2)_nNR_aR_b$.
$R'_6$ represents a $(C_1-C_7)$-alkyl.

The inventors have found that the substitution of the nitrogen of the indole moiety borne by the carbonyl group, in particular by an alkyl group gives compounds that are only NorA efflux pump inhibitors without any antibacterial activity.

Thus compounds of the invention are either only antibacterials or only NorA efflux pump inhibitors or present both activities.

In an advantageous embodiment, the present invention relates to compounds formula X defined above, having the following structure:

Compound 7

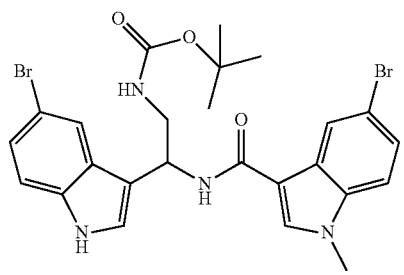

In an advantageous embodiment, the present invention relates to compounds of one of the formula I to IV defined above, the following formula XI:

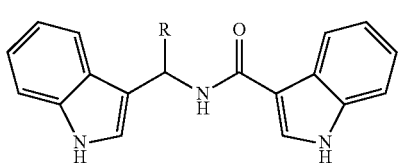

XI wherein:
R represents H, a $(C_1-C_7)$-alkyl, $CH_2NHCO_2$—$(C_1-C_7)$-alkyl, $CH_2NHCO_2$—$(C_3-C_7)$-cycloalkyl, $CO_2H$, $CO_2$—$(C_1-C_7)$-alkyl, $CO_2$—$(C_3-C_7)$-cycloalkyl, $(CH_2)_nOH$, $CH_2NH(CH_2)_n$—OH, $CH_2NH(CH_2)_n$—$NR_aR_b$, CONH—$(C_1-C_7)$-alkyl, CONH—$(C_3-C_7)$-cycloalkyl, CONH-aryl, CONH—$(CH_2)_nOH$, CONH—$(CH_2)_nNR_aR_b$, wherein n=2 to 12 and $R_a$, $R_b$, aryl and alkyl being as defined above.

In an advantageous embodiment, the present invention relates to compounds of formula XI defined above, having the following structure:

Compound 3a

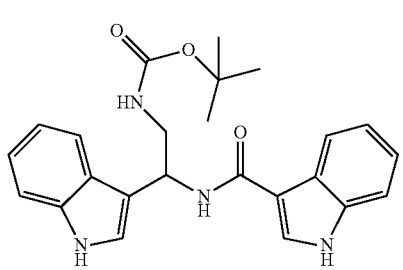

In another aspect, the present invention relates to products having the general formula I to XI defined above.

The compounds having said general formula I to XI are new compounds as such.

In an advantageous embodiment, the present invention relates to products of formula I to XI defined above, selected from the group consisting of:

Compound 3f
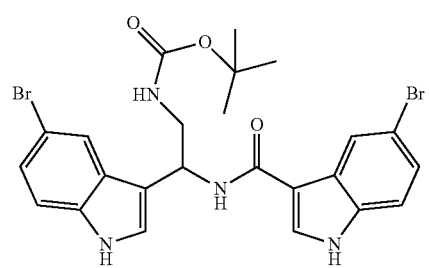
Compound 4
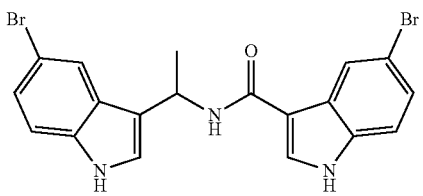
Compound 3b
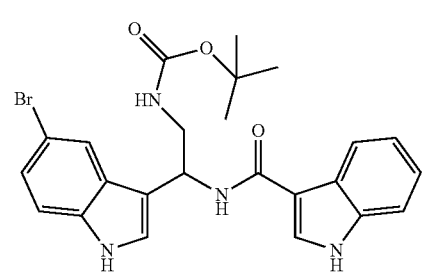
Compound 12
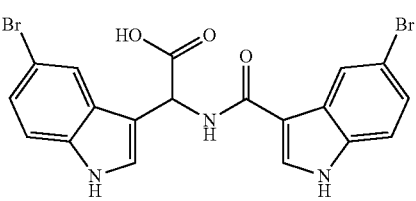
Compound 3c
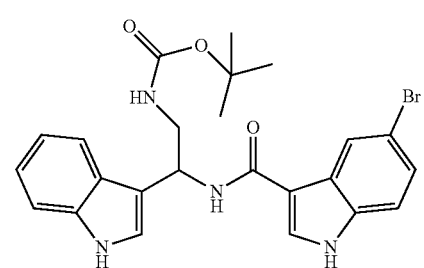
Compound 11
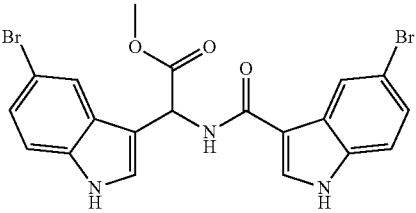
Compound 5
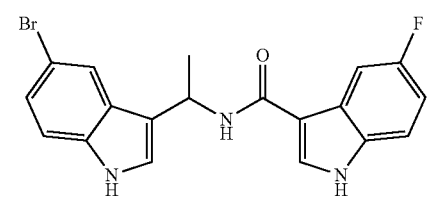
Compound 13
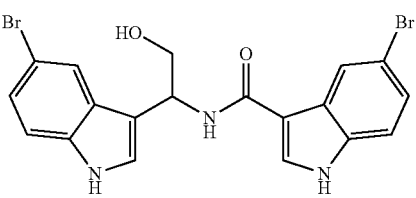
Compound 6a
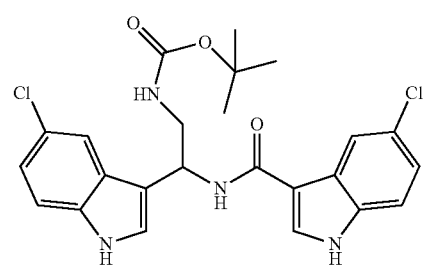
Compound 14
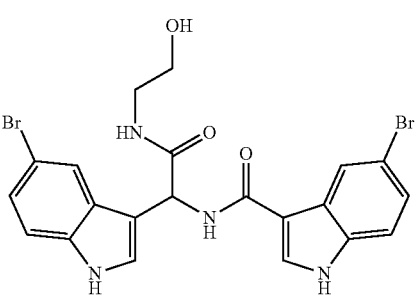
Compound 6b
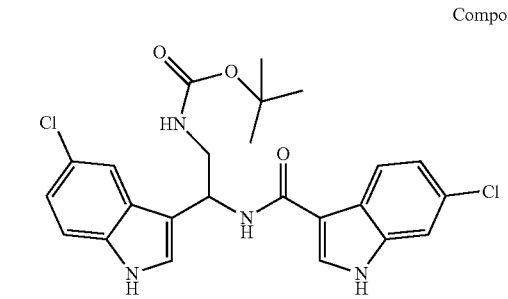
Compound 15
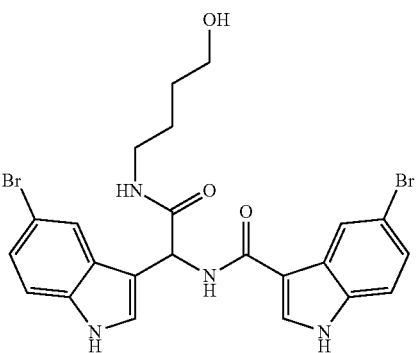

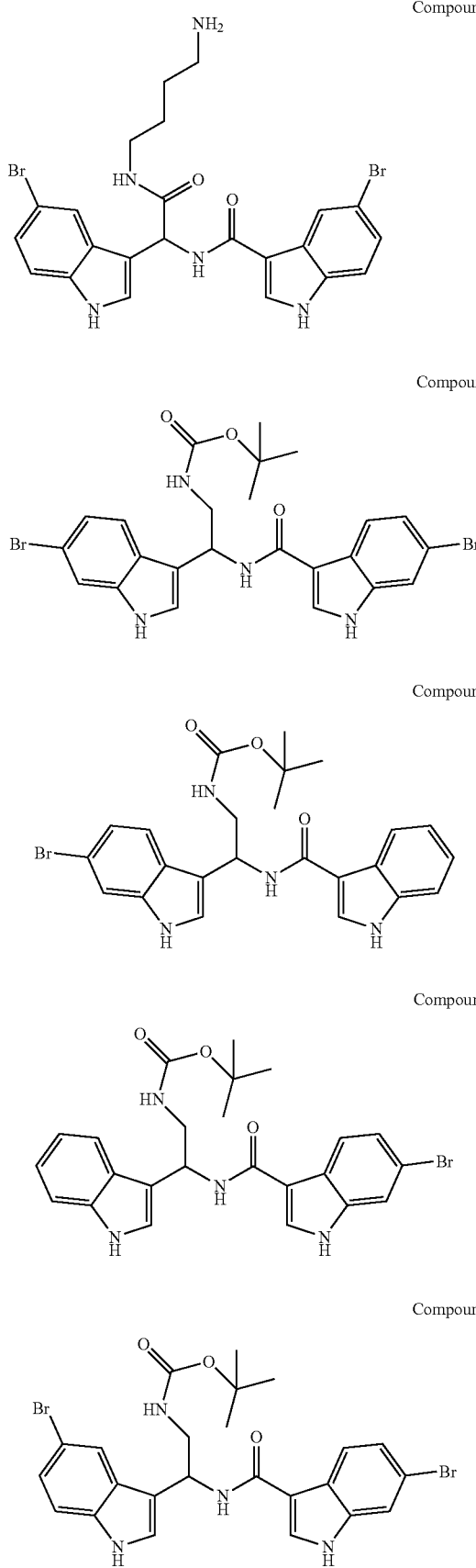
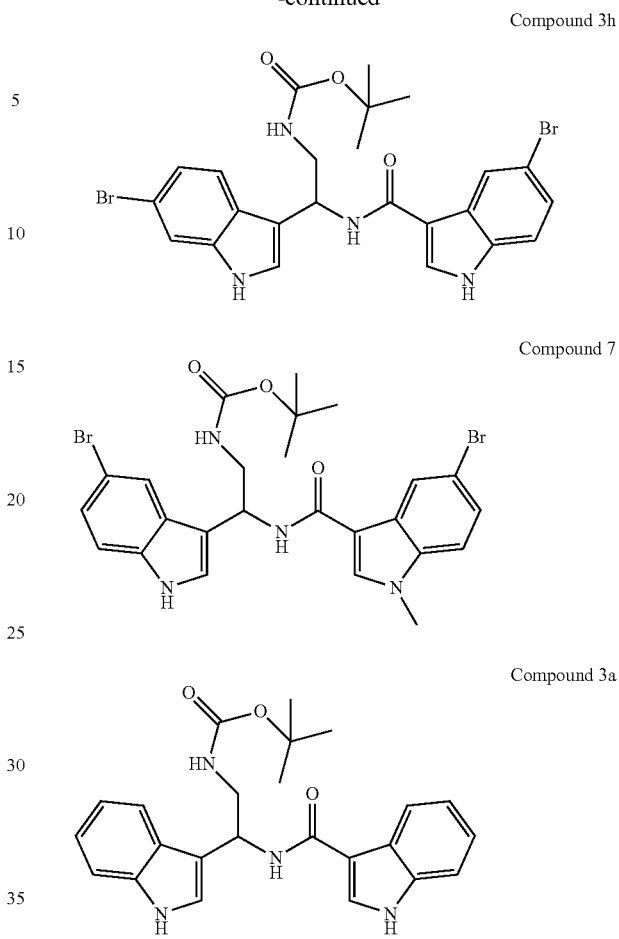

In another aspect, the present invention relates to a pharmaceutical composition comprising a compound of formula I, in association with a pharmaceutically acceptable vehicle.

The expression "pharmaceutically acceptable vehicle" denotes in particular cellulose, starch, benzyl alcohol, polyethylene glycol, gelatin, lactose, polysorbate, magnesium or calcium stearate, xanthan gum, guar, alginate, colloidal silica.

The compositions according to the invention can be used by oral, parenteral, topic, or rectal route or in aerosols.

As solid compositions for oral administration, tablets, pills, gelatin capsules, powders or granules can be used. In these compositions, the active ingredient according to the invention is mixed with one or more inert diluents or adjuvants, such as saccharose, lactose or starch. These compositions can comprise substances other than the diluents, for example a lubricant such as magnesium stearate or a coating intended for controlled release.

As liquid compositions for oral administration, pharmaceutically acceptable solutions, suspensions, emulsions, syrups and elixirs containing inert diluents such as water or paraffin oil can be used. These compositions can also comprise substances other than the diluents, for example wetting products, sweeteners or flavourings.

The compositions for parenteral administration can be sterile solutions or emulsions. As solvent or vehicle, water, propylene glycol, a polyethylene glycol, vegetable oils, in particular olive oil, injectable organic esters, for example ethyl oleate can be used. These compositions can also contain adjuvants, in particular wetting agents, isotoning agents, emulsifiers, dispersants and stabilizers.

The sterilization can be carried out in several ways, for example using a bacteriological filter, by irradiation or by heating. They can also be prepared in the form of sterile solid compositions which can be dissolved at the moment of use in sterile water or any other injectable sterile medium.

The compositions for topical administration can be for example creams, ointments, lotions or aerosols.

The compositions for rectal administration are suppositories or rectal capsules, which, in addition to the active ingredient, contain excipients such as cocoa butter, semi-synthetic glycerides or polyethylene glycols.

The compositions can also be aerosols.

For use in the form of liquid aerosols, the compositions can be stable sterile solutions or solid compositions dissolved at the moment of use in pyrogen-free sterile water, in serum or any other pharmaceutically acceptable vehicle. For use in the form of dry aerosols intended to be directly inhaled, the active ingredient is finely divided and combined with a diluent or hydrosoluble solid vehicle, for example dextran, mannitol or lactose.

In an advantageous embodiment, the present invention relates to a pharmaceutical composition defined above, administrable by oral route at a dose comprised from about 10 mg/kg to about 200 mg/kg.

In an advantageous embodiment, the present invention relates to a pharmaceutical composition defined above, under a form liable to be administrable by oral route at a dose comprised from 100 mg to 1,500 mg, in particular from 100 mg to 1,000 mg, in particular from 100 to 500 mg.

Said pharmaceutical composition can be administered 2 or 3 times per day.

In an advantageous embodiment, the present invention relates to a pharmaceutical composition defined above, administrable by intraveinous route at a dose comprised from about 5 µg/kg to about 50 mg/kg.

In an advantageous embodiment, the present invention relates to a pharmaceutical composition defined above, under a form liable to be administrable by intraveinous route at a dose comprised from 0.1 mg to 1000 mg, in particular from 10 mg to 1,000 mg, in particular from 10 to 500 mg, in particular from 10 to 100 mg.

Said pharmaceutical composition can be administered 2 or 3 times per day.

In an advantageous embodiment, the present invention relates to a pharmaceutical composition defined above, comprising a compound selected from the group consisting of: compound 3b, 3c, 3f, 4, 5, 6a, and 11-16.

In an advantageous embodiment, the present invention relates to a pharmaceutical composition defined above, comprising a compound selected from the group consisting of: compounds 3d, 3e and 3i.

In an advantageous embodiment, the present invention relates to a pharmaceutical composition defined above, comprising the compounds 3g and 6b.

In an advantageous embodiment, the present invention relates to a pharmaceutical composition defined above, comprising the compound 3h.

In an advantageous embodiment, the present invention relates to a pharmaceutical composition defined above, comprising the compound 7.

In an advantageous embodiment, the present invention relates to a pharmaceutical composition defined above, comprising the compound 3a.

In another aspect, the present invention relates to a pharmaceutical composition comprising,
in combination with a pharmaceutically acceptable vehicle:
  at least one compound of formula I as defined above, and
  at least one antibiotic compound, in particular from the family of the fluoroquinolones, such as ciprofloxacin, norfloxacin, pefloxacin, enofloxacin, ofloxacin, levofloxacin and moxifloxacin,
said pharmaceutical composition being used for simultaneous or separate use or use spread over time intended for the treatment of pathologies associated with bacterial infections presenting a resistance to an antibacterial compound, in particular from the family of the fluoroquinolones.

Said antibiotic compound must be from a different family of the one of the compound of the invention.

In this embodiment, if a compound of the invention is a NorA efflux pump inhibitor, administration of said compound with an antibiotic for which the bacteria is resistant allows restoring the antibiotic activity against bacteria that became resistant to said antibiotic.

If the compound of the invention presents only an antibacterial activity, administration of said compound with another antibiotic allows having a broader spectrum or increased activity.

The pharmaceutical composition of the invention as defined above comprises approximately 350 to approximately 2,000 mg, preferably approximately 1,000 to approximately 1,500 mg, of compound of formula (I) according to the invention in 1 to 4 administrations per day and approximately 350 to approximately 2,000 mg, preferably approximately 1,000 to approximately 1,500 mg, of antibiotic compound, in particular of the family of the fluoroquinolones, such as ciprofloxacin in 1 to 4 administrations per day, preferably in 2 administrations per day.

DESCRIPTION OF THE FIGURES

FIG. 1A: compound 3f.

The horizontal full line indicates the bacterial load at the beginning of the experiment (i.e., primary bacterial load).

Figure 1A:
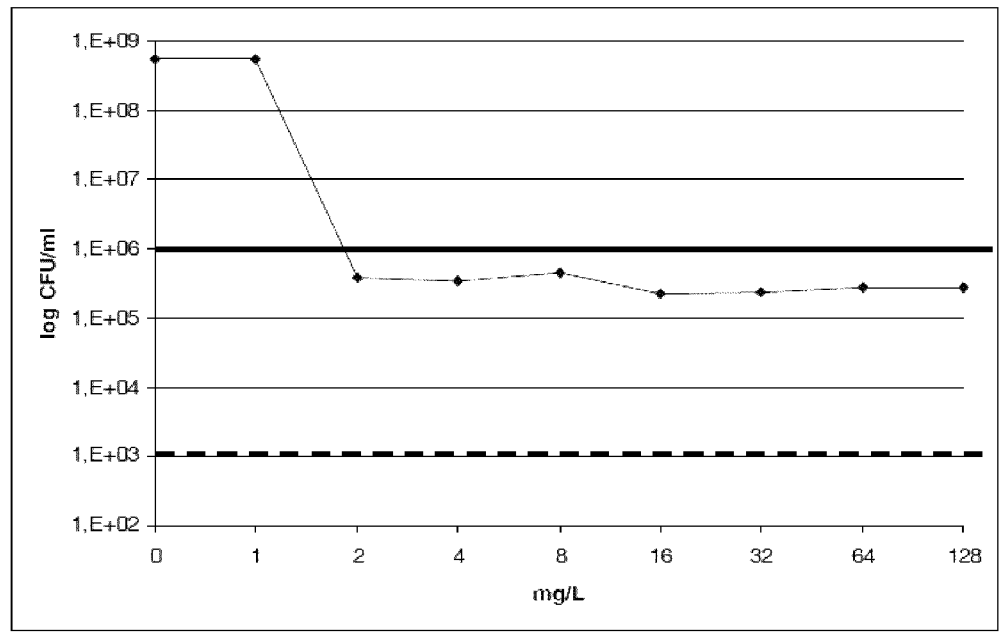
FIGS. 1A and 1B present concentration-killing curves for the indolic compounds 3f and 4 against *S. aureus* ATCC 25923. The activity is evaluated after 18 h incubation of *S. aureus* cultures in the presence of the tested compound.
Figure 1B:
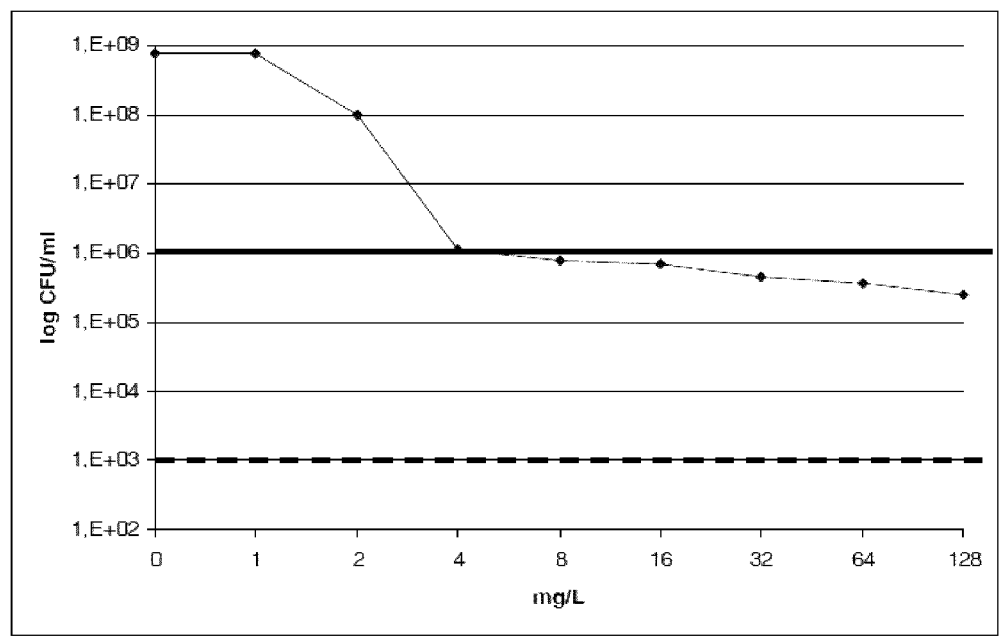

The area between the horizontal full line and the dashed line corresponds to a bacteriostatic effect and the area below the dashed line corresponds to a bactericidal effect (i.e., ≥3 log reduction of the primary bacterial inoculum after 18 h incubation of cultures in the presence of the tested compound).

x-axis: concentration of compound 3f (mg/L)
y-axis: bacterial density (log CFU/mL)
FIG. 1B: compound 4
As above, the area between the horizontal full line and the dashed line corresponds to a bacteriostatic effect and the area below the dashed line corresponds to a bactericidal effect.

x-axis: concentration of compound 4 (mg/L)
y-axis: bacterial density (log CFU/mL)
FIGS. 1A and 1B show that the indolic compounds 3f and 4 have no detectable bactericidal activity against *S. aureus* ATCC 25923 at concentrations up to 128 mg/L, as evaluated after 18 h of incubation of cultures.

Figure 2:
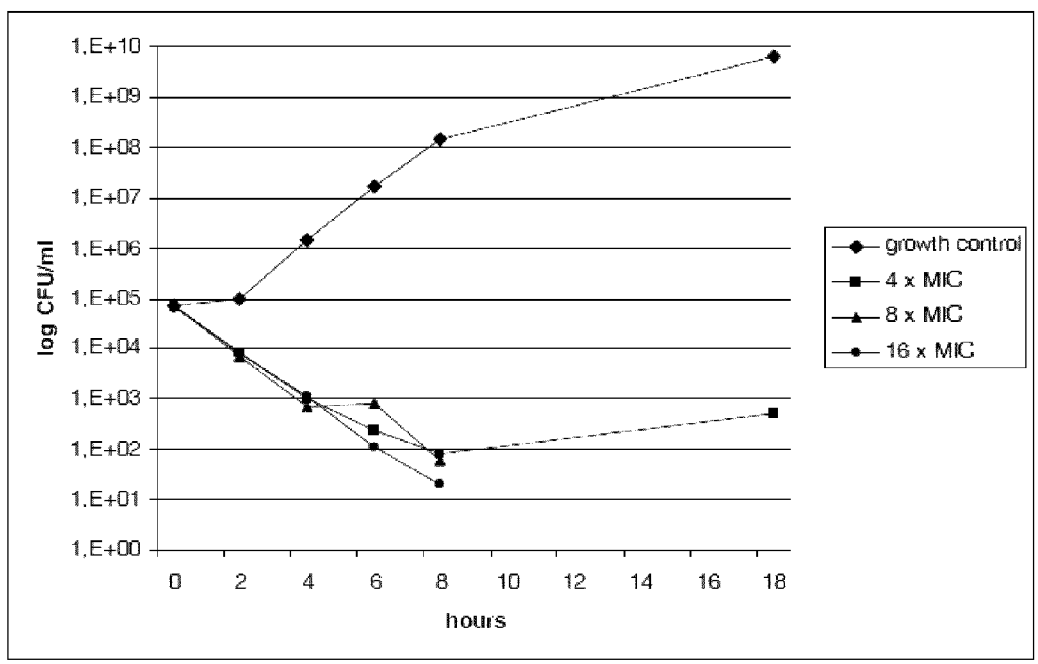

FIG. 2 presents the time-kill curve of compound 3f (tested at MIC×4, 8 or 16) obtained with *S. aureus* ATCC 25923.

Full line, black diamonds: drug-free control

Full line, black squares: compound 3f (MIC×4); black triangles: 3f at MIC×8; black circles: 3f at MIC×16.

x-axis: time (h)

y-axis: log CFU/mL

The figure shows that compound 3f has a significant bactericidal activity against *S. aureus* ATCC 25923 after 8 h incubation, at 4×, 8× and 16× the MIC for this strain. The incubation period is prolonged to 18 h for 3f at 4×MIC, and a progressive bacterial regrowth is observed. This may explain that no bactericidal activity was found after 18 h incubation for concentration-killing curves experiments (see FIG. 1A).

Altogether, this results show that the indolic compounds display an early but significant bactericidal effect against *S. aureus* strains. The rapid bacterial regrowth could impose more frequent administration of the indolic compound in clinical practice to maintain a significant bactericidal activity.

EXAMPLES

Experimental Part—Chemistry

The following examples describe the synthesis of 16 compounds of the invention (compounds 3 to 7 and 11 to 16) and the intermediates.

Example 1: Synthesis of Compounds (2)

These compounds have been prepared in two steps according to A. S. Katner, <<Improved synthesis of indole-3-carboxylic acids>>, *Organic Preparations and Procedures* 1970, 2, 297-303 (scheme I).

1.1: First Step: Acylation of Indoles by Trifluoroacetic Anhydride 1-(5-Bromo-1H-indol-3-yl)-2,2,2-trifluoroethanone (hb)

Commercially available, for example:
ASW MedChem, Inc. 100 Jersey Ave Box C-10 New Brunswick, N.J. 08901 USA Its synthesis from 5-bromoindole (ab) was described in the following article: D. Kumar, N. M. Kumar, K.-H. Chang, K. Shah *Eur. J. Med. Chem.* 2010, 45, 4664-4668. The used experimental conditions (($CF_3CO)_2O$, DMF, 0° C., 3 h) were previously described in: C. J. Swain, R. Baker, C. Kneen, J. Moseley, J. Saunders, E. M. Seward, G. Stevenson, M. Beer, J. Stanton, K. Watling *J. Med. Chem.* 1991, 34, 140-151. These experimental conditions are also reported in the following articles: C. M. Park, S. Y. Kim, W. K. Park, N. S. Park, C. M. Seong, *Bioorg. Med. Chem. Lett.* 2008, 18, 3844-3847 and C. R. Hopkins, M. Czekaj, S. S. Kaye, Z. Gao, J. Pribish, H. Pauls, G. Liang, K. Sides, D. Cramer, J. Caims, Y. Luo, H. Lim, R. Vaz, S. Rebello, S. Maignan, A. Dupuy, M. Mathieu, J. Levell *Bioorg. Med. Chem. Lett.* 2005, 15, 2734-2737.

In a dry flask under argon, 5-bromoindole (ab) (3.0 g, 15.31 mmol) was dissolved in dry DMF (15 mL). This solution was cooled to 0° C. and trifluoroacetic anhydride (3.19 mL, 22.96 mmol) was added dropwise. The mixture was stirred at 0° C. for 2 h30 then quenched with water. The crude mixture was filtered to afford a solid. This solid was washed twice with water and dissolved in ethyl acetate. The organic layer was washed with an aqueous solution of $NaHCO_3$ and brine, dried over anhydrous $MgSO_4$ and evaporated under vacuum. The desired product (hb) was obtained as a solid (4.381 g, 15.0 mmol) without further purification. Yield: 98%.

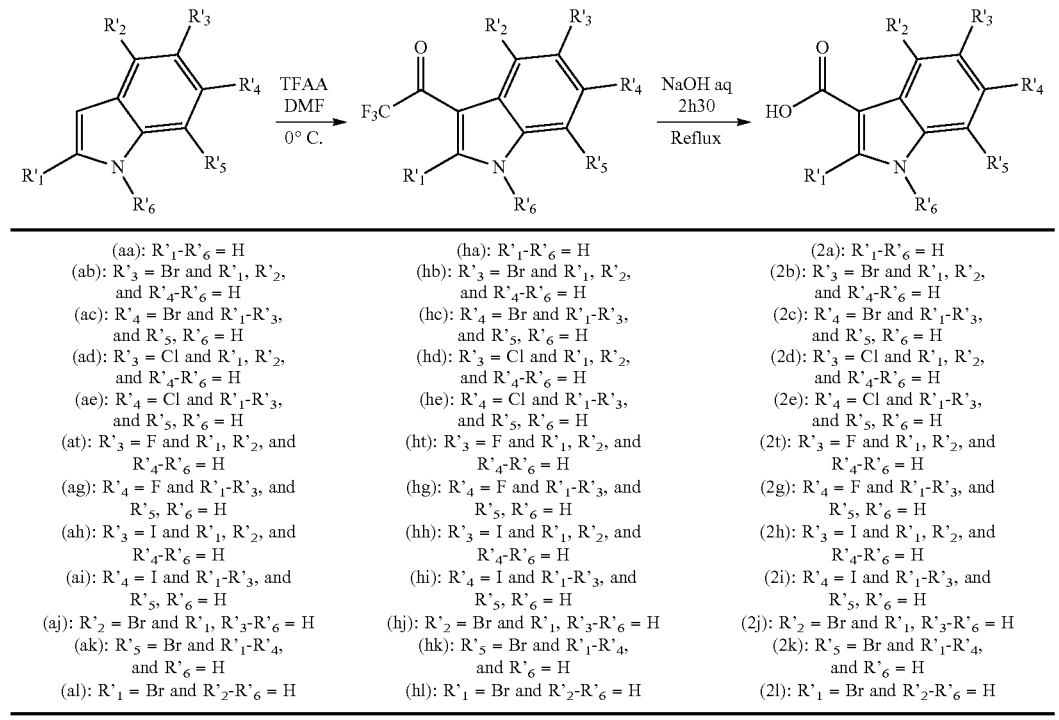

SCHEME I (aa): R'$_1$-R'$_6$ = H
(ab): R'$_3$ = Br and R'$_1$, R'$_2$, and R'$_4$-R'$_6$ = H
(ac): R'$_4$ = Br and R'$_1$-R'$_3$, and R'$_5$, R'$_6$ = H
(ad): R'$_3$ = Cl and R'$_1$, R'$_2$, and R'$_4$-R'$_6$ = H
(ae): R'$_4$ = Cl and R'$_1$-R'$_3$, and R'$_5$, R'$_6$ = H
(af): R'$_3$ = F and R'$_1$, R'$_2$, and R'$_4$-R'$_6$ = H
(ag): R'$_4$ = F and R'$_1$-R'$_3$, and R'$_5$, R'$_6$ = H
(ah): R'$_3$ = I and R'$_1$, R'$_2$, and R'$_4$-R'$_6$ = H
(ai): R'$_4$ = I and R'$_1$-R'$_3$, and R'$_5$, R'$_6$ = H
(aj): R'$_2$ = Br and R'$_1$, R'$_3$-R'$_6$ = H
(ak): R'$_5$ = Br and R'$_1$-R'$_4$, and R'$_6$ = H
(al): R'$_1$ = Br and R'$_2$-R'$_6$ = H (ha): R'$_1$-R'$_6$ = H
(hb): R'$_3$ = Br and R'$_1$, R'$_2$, and R'$_4$-R'$_6$ = H
(hc): R'$_4$ = Br and R'$_1$-R'$_3$, and R'$_5$, R'$_6$ = H
(hd): R'$_3$ = Cl and R'$_1$, R'$_2$, and R'$_4$-R'$_6$ = H
(he): R'$_4$ = Cl and R'$_1$-R'$_3$, and R'$_5$, R'$_6$ = H
(hf): R'$_3$ = F and R'$_1$, R'$_2$, and R'$_4$-R'$_6$ = H
(hg): R'$_4$ = F and R'$_1$-R'$_3$, and R'$_5$, R'$_6$ = H
(hh): R'$_3$ = I and R'$_1$, R'$_2$, and R'$_4$-R'$_6$ = H
(hi): R'$_4$ = I and R'$_1$-R'$_3$, and R'$_5$, R'$_6$ = H
(hj): R'$_2$ = Br and R'$_1$, R'$_3$-R'$_6$ = H
(hk): R'$_5$ = Br and R'$_1$-R'$_4$, and R'$_6$ = H
(hl): R'$_1$ = Br and R'$_2$-R'$_6$ = H (2a): R'$_1$-R'$_6$ = H
(2b): R'$_3$ = Br and R'$_1$, R'$_2$, and R'$_4$-R'$_6$ = H
(2c): R'$_4$ = Br and R'$_1$-R'$_3$, and R'$_5$, R'$_6$ = H
(2d): R'$_3$ = Cl and R'$_1$, R'$_2$, and R'$_4$-R'$_6$ = H
(2e): R'$_4$ = Cl and R'$_1$-R'$_3$, and R'$_5$, R'$_6$ = H
(2f): R'$_3$ = F and R'$_1$, R'$_2$, and R'$_4$-R'$_6$ = H
(2g): R'$_4$ = F and R'$_1$-R'$_3$, and R'$_5$, R'$_6$ = H
(2h): R'$_3$ = I and R'$_1$, R'$_2$, and R'$_4$-R'$_6$ = H
(2i): R'$_4$ = I and R'$_1$-R'$_3$, and R'$_5$, R'$_6$ = H
(2j): R'$_2$ = Br and R'$_1$, R'$_3$-R'$_6$ = H
(2k): R'$_5$ = Br and R'$_1$-R'$_4$, and R'$_6$ = H
(2l): R'$_1$ = Br and R'$_2$-R'$_6$ = H $^1$H NMR (300 MHz, CDCl$_3$): δ=7.35 (d, J=8.4 Hz, 1H, CH), 7.48 (dd, J=2.4 and 8.4 Hz, 1H, CH), 8.06 (d, J=1.8 Hz, 1H, CH), 8.58 (d, J=2.1 Hz, 1H, CH), 8.90 (br s, 1H, NH) ppm. LRMS (ESI): m/z=290 and 292 [(M−H)$^-$].

1-(6-Bromo-1H-indol-3-yl)-2,2,2-trifluoroethanone (hc)

Commercially available, for example:
ASW MedChem, Inc. 100 Jersey Ave Box C-10 New Brunswick, N.J. 08901 USA In a dry flask under argon, 6-bromoindole (ac) (196 mg, 1.0 mmol) was dissolved in dry DMF (3 mL). This solution was cooled to 0° C. and trifluoroacetic anhydride (0.166 mL, 1.2 mmol) was added dropwise. The mixture was stirred at 0° C. during 1 hour then quenched with water. The resulting suspension was stirred for 15 minutes and the product was extracted with diethyl ether (3×30 mL). The combined organic layers were washed with an aqueous solution of NaHCO$_3$ and brine, dried over anhydrous MgSO$_4$ and evaporated under vacuum. The desired product (hc) was obtained as a yellow solid (277 mg, 0.95 mmol) without further purification. Yield: 95%.

$^1$H NMR (300 MHz, CD$_3$OD): δ=7.26 (dd, J=1.8 and 8.5 Hz, 1H), 7.59 (dd, J=0.5 and 1.8 Hz, 1H), 7.94 (s, 1H), 7.96 (dd, J=0.5 and 8.5 Hz, 1H) ppm. $^{13}$C NMR (75.5 MHz, CD$_3$OD): δ=109.1 (C), 115.9 (CH), 117.0 (C), 123.4 (CH), 125.6 (CH), 126.5 (C), 134.1 (CH), 138.9 (C), 168.7 (CO) ppm.

1-(5-Chloro-1H-indol-3-yl)-2,2,2-trifluoroethanone (hd)

To a stirred solution of 5-chloroindole (ad) (455 mg, 3.0 mmol) in 10 mL of dry DMF, trifluoroacetic anhydride (0.459 mL, 3.3 mmol) was added at 0° C. The resulting mixture was stirred at room temperature during 1 hour. A saturated aqueous solution of NaHCO$_3$ was then added. The mixture was extracted with EtOAc (3×20 mL) and the collected organic layers were washed with brine, dried over anhydrous MgSO$_4$, filtered, and concentrated under vacuum. The product (hd) was obtained as a white solid (705 mg, 2.37 mmol) without further purification. Yield: 95%.

$^1$H NMR (300 MHz, (CD$_3$)$_2$CO): δ=7.36 (dd, J=2.1 and 8.7 Hz, 1H), 7.65 (dd, J=0.6 and 8.7 Hz, 1H), 8.28 (dd, J=0.6 and 2.1 Hz, 1H), 8.45-8.47 (m, 1H), 11.78 (br s, 1H, NH) ppm. $^{13}$C NMR (75.5 MHz, (CD$_3$)$_2$CO): δ=116.1 (CH), 116.5 (C), 122.8 (CH), 125.6 (C), 126.6 (CH), 127.0 (C), 135.1 (CH), 138.2 (C), 180.3 (CO) ppm.

1-(6-Chloro-1H-indol-3-yl)-2,2,2-trifluoroethanone (he)

Commercially available:
ASW MedChem, Inc. 100 Jersey Ave Box C-1 New Brunswick, N.J. 08901 USA and Beta Pharma Scientific, Inc. 31 Business Park Dr. Branford, Conn. 06405 USA Its synthesis from 6-chloroindole (ae) was described in the following patents: C. Bissantz, et al., PCT Int. Appl., 2007009906, 25 Jan. 2007; C. Bissantz et al., U.S. Pat. Appl. Publ., 20080161332, 3 Jul. 2008.

To a stirred solution of 6-chloroindole (ae) (455 mg, 3.0 mmol) in 10 mL of dry DMF, trifluoroacetic anhydride (0.459 mL, 3.3 mmol) was added at 0° C. The resulting mixture was stirred at room temperature during 1 hour. A saturated aqueous solution of NaHCO$_3$ was then added. The mixture was extracted with EtOAc (3×20 mL) and the collected organic layers were washed with brine, dried over anhydrous MgSO$_4$, filtered and concentrated under vacuum. The product (he) was obtained as a white solid (725 mg, 2.44 mmol) without further purification. Yield: 98%.

$^1$H NMR (300 MHz, (CD$_3$)$_2$CO): δ=7.35 (dd, J=1.1 and 8.5 Hz, 1H), 7.67 (s, 1H), 8.26 (d, J=8.5 Hz, 1H), 8.44 (s, 1H), 11.70 (br s, 1H, NH) ppm. $^{13}$C NMR (75.5 MHz, (CD$_3$)$_2$CO): δ=114.5 (CH), 116.1 (C), 122.8 (C), 124.6 (CH), 125.7 (CH), 128.2 (C), 136.1 (CH), 136.5 (C), 179.5 (CO) ppm.

1-(5-Fluoro-1H-indol-3-yl)-2,2,2-trifluoroethanone (hf)

Commercially available:
ASW MedChem, Inc. 100 Jersey Ave Box C-1 New Brunswick, N.J. 08901 USA Its synthesis from 5-fluoroindole is described in the following patent: T. C. Hancox et al., PCT Int. Appl., 2009053715, 30 Apr. 2009.

To a stirred solution of 5-fluoroindole (af) (405 mg, 3.0 mmol) in 10 mL of dry DMF, trifluoroacetic anhydride (0.459 mL, 693 mg, 3.3 mmol) was added at 0° C. The resulting mixture was stirred at room temperature during 1 hour. A saturated aqueous solution of NaHCO$_3$ was then added. The mixture was extracted with EtOAc (3×20 mL) and the collected organic layers were washed with brine, dried over anhydrous MgSO$_4$, filtered, and concentrated under vacuum. The product (ht) was obtained as a white solid (660 mg, 2.86 mmol) without further purification. Yield: 95%.

1-(6-Fluoro-1H-indol-3-yl)-2,2,2-trifluoroethanone (hg)

Its synthesis from 6-fluoro-1H-indole (ag) is described in the patent: A. J. Ratcliffe et al., PCT Int. Appl., 2006038001, 13 Apr. 2006.

The compound (hg) can be prepared by the method described in the invention.

1-(5-Iodo-1H-indol-3-yl)-2,2,2-trifluoroethanone (hh)

Its synthesis from 5-iodo-1H-indole (ah) is described in the patent: C. Seong et al., Eur. Pat. Appl., 2108649, 14 Oct. 2009. Experimental conditions: trifluoroacetic anhydride, DMF, 1 h, rt.

The compound (hh) can be prepared by the method described in the invention.

1-(6-iIodo-1H-indol-3-yl)-2,2,2-trifluoroethanone (hi)

The compound (hi) can be prepared by the method described in the invention.

1-(4-Bromo-1H-indol-3-yl)-2,2,2-trifluoroethanone (hj)

Commercially available:
ASW MedChem, Inc. 100 Jersey Ave Box C-10 New Brunswick, N.J. 08901 USA Synthesis:
Esaki, Tohru; Nishimura, Yoshikazu; Isshiki, Yoshiaki; Okamoto, Naoki; Furuta, Yoshiyuki; Mizutani, Akemi;

Ohta, Masateru; Lai, Wayne Wen; Kotake, Tomoy, PCT Int. Appl. (2010), WO 2010126030 A1 20101104.

The compound (hj) can be prepared by the method described in the invention.

1-(7-Bromo-1H-indol-3-yl)-2,2,2-trifluoroethanone (hk)

1-(2-Bromo-1H-indol-3-yl)-2,2,2-trifluoroethanone (hl)

The compounds (hk) and (hl) can be prepared by the method described in the invention.

1.2 Second Step: Synthesis of Compounds (2a-l)

1H-Indole-3-carboxylic acid (2a)

Commercially available, for example:
Acros Organics, part of Thermo Fisher Scientific Janssens Pharmaceuticalaan 3A Geel, 2440 Belgium 5-Bromo-1H-indole-3-carboxylic acid (2b)

Its synthesis from 1-(5-bromo-1H-indol-3-yl)-2,2,2-trifluoroethanone (hb) was described in the following article: D. Kumar, N. M. Kumar, K.-H. Chang, K. Shah Eur. *J. Med. Chem.* 2010, 45, 4664-4668. The used experimental conditions (20% aqueous NaOH, reflux) were previously described in: C. J. Swain, R. Baker, C. Kneen, J. Moseley, J. Saunders, E. M. Seward, G. Stevenson, M. Beer, J. Stanton, K. Watling *J. Med. Chem.* 1991, 34, 140-151. These experimental conditions are also reported in the following articles: C. M. Park, S. Y. Kim, W. K. Park, N. S. Park, C. M. Seong *Bioorg. Med. Chem. Lett.* 2008, 18, 3844-3847 and C. R. Hopkins, M. Czekaj, S. S. Kaye, Z. Gao, J. Pribish, H. Pauls, G. Liang, K. Sides, D. Cramer, J. Caims, Y. Luo, H. Lim, R. Vaz, S. Rebello, S. Maignan, A. Dupuy, M. Mathieu, J. Levell *Bioorg. Med. Chem. Lett.* 2005, 15, 2734-2737.

A flask was charged with 1-(5-bromo-1H-indol-3-yl)-2,2,2-trifluoroethanone (hb) (4.30 g, 14.72 mmol) and an aqueous solution of sodium hydroxide (180 mL, 20% wt.) was added. This mixture was refluxed for 2 h30 then carefully acidified to pH=1 with an aqueous solution of 6M HCl. During this acidification, the carboxylic acid precipitated. The resulting suspension was filtered. The solid was washed with water and dissolved in a mixture of ethyl acetate/methanol (about 9/1). The organic layer was dried over anhydrous $MgSO_4$ and evaporated under vacuum. The desired product (2b) (3.528 g, 14.7 mmol) was obtained as a beige solid. Yield: quant.
$^1$H NMR (300 MHz, DMSO-$d_6$): δ=7.30 (dd, J=2.1 and 8.7 Hz, 1H, CH), 7.45 (d, J=8.7 Hz, 1H, CH), 8.04 (d, J=3.0 Hz, 1H, CH), 8.12 (d, J=2.1 Hz, 1H, CH), 12.09 (br s, 1H, NH) ppm. $^{13}$C NMR (75.5 MHz, DMSO-$d_6$): δ=107.0 (C), 113.8 (CH), 114.4 (C), 122.6 (CH), 124.6 (CH), 127.8 (C), 133.4 (CH), 135.2 (C), 165.6 (CO) ppm.

6-Bromo-1H-indole-3-carboxylic acid (2c)

A flask was charged with 1-(6-bromo-1H-indol-3-yl)-2,2,2-trifluoroethanone (hc) (292 mg, 1.0 mmol) and an aqueous solution of sodium hydroxide (180 mL, 20% wt.) was added. This mixture was refluxed for 5 hours. The resulting mixture was cooled and washed with diethyl ether (2×20 mL) The aqueous phase was then carefully acidified to pH=1 with an aqueous solution of 6M HCl. The product was extracted with diethyl ether (3×30 mL). The combined organic layers were washed with water, dried over anhydrous $MgSO_4$, filtered and evaporated under vacuum. The desired product (2c) (192 mg, 0.8 mmol) was obtained as a grey solid. Yield: 80%.

5-Chloro-1H-indole-3-carboxylic acid (2d)

Solid 1-(5-chloro-1H-indol-3-yl)-2,2,2-trifluoroethanone (hd) (743 mg, 3.0 mmol) was suspended in 10 mL of a 4M aqueous solution of sodium hydroxide. The resulting mixture was stirred at reflux during 1 hour. The solution was extracted with diethyl ether (2×25 mL) and then the aqueous phase was acidified with an aqueous solution of 5M HCl to pH 1. The precipitate was filtered off, washed with water and dried in the presence of $P_2O_5$ under reduced pressure. Pure 5-chloroindolic acid (2d) (480 mg, 2.45 mmol) was obtained as a beige solid. Yield: 82%.
$^1$H NMR (300 MHz, $(CD_3)_2CO$): δ=7.20 (dd, J=2.0 and 8.7 Hz, 1H), 7.53 (d, J=8.7 Hz, 1H), 8.10-8.15 (m, 2H), 11.07 (br s, 1H, NH) ppm. $^{13}$C NMR (75.5 MHz, $(CD_3)_2CO$): δ=110.5 (C), 115.3 (CH), 120.6 (C), 122.2 (CH), 124.5 (CH), 128.2 (C), 135.2 (CH), 138.1 (C), 167.3 (CO) ppm.

6-Chloro-1H-indole-3-carboxylic acid (2e)

Commercially available, for example:
American Custom Chemicals Corp. P O Box 262527 San Diego, Calif. 92196-2527 USA Its synthesis from 1-(6-chloro-1H-indol-3-yl)-2,2,2-trifluoroethanone (he) was described in the following patents: C. Bissantz et al, PCT Int. Appl., 2007009906, 25 Jan. 2007 (synthesis from 6-chloroindole according to *J. Med. Chem.* 1991, 34, 140); C. Bissantz et al., U.S. Pat. Appl. Publ., 20080161332, 3 Jul. 2008.

1-(6-Chloro-1H-indol-3-yl)-2,2,2-trifluoroethanone (he) (743 mg, 3.0 mmol) was suspended in 10 mL of a 4M aqueous solution of sodium hydroxide. The resulting mixture was stirred at reflux during 1 hour. The solution was extracted with diethyl ether (2×25 mL) and then aqueous phase was acidified with an aqueous solution of 5M HCl to pH 1. The precipitate was filtered off, washed with water and dried in the presence of $P_2O_5$. Pure 6-chloroindolic acid (2e) (475 mg, 2.43 mmol) was obtained as a beige solid. Yield: 81%.
$^1$H NMR (300 MHz, $(CD_3)_2CO$): δ=7.20 (dd, J=1.8 and 8.6 Hz, 1H), 7.56 (d, J=1.8 Hz, 1H), 8.01-8.13 (m, 2H), 11.02 (br s, 1H), 11.02 (br s, 1H, NH) ppm. $^{13}$C NMR (75.5 MHz, $(CD_3)_2CO$): δ=110.6 (C), 113.7 (CH), 123.6 (CH), 124.1 (CH), 125.4 (C), 128.2 (C), 134.8 (CH), 136.9 (C), 167.0 (CO) ppm.

5-Fluoro-1H-indole-3-carboxylic acid (2f)

Commercially available, for example:
American Custom Chemicals Corp. P O Box 262527 San Diego, Calif. 92196-2527 USA Its synthesis from 1-(5-fluoro-1H-indol-3-yl)-2,2,2-trifluoroethanone (hf) was described in the following patent: T. C. Hancox et al., PCT Int. Appl., 2009053715, 30 Apr. 2009.

1-(5-Fluoro-1H-indol-3-yl)-2,2,2-trifluoroethanone (hf) (693 mg, 3.0 mmol) was suspended in 10 mL of a 4M aqueous solution of sodium hydroxide. The resulting mixture was stirred at reflux during 1 hour. The solution was extracted with diethyl ether (2×25 mL) and then aqueous the phase was acidified with an aqueous solution of 5M HCl to pH 1. The precipitate was filtered off, washed with water and dried in the presence of $P_2O_5$ under reduced pressure. Pure 5-fluoroindolic acid (2e) (451 mg, 2.52 mmol) was obtained as a beige solid. Yield: 84%.

$^1$H NMR (300 MHz, $CD_3OD$): δ=6.96 (td, J=2.6 and 9.3 Hz, 1H), 7.40 (dd, J=4.4 and 8.9 Hz, 1H), 7.71 (dd, J=2.6 and 9.9 Hz, 1H), 7.98 (s, 1H), 11.41 (br s, 1H, NH) ppm. $^{13}$C NMR (75.5 MHz, $CD_3OD$): δ=106.9 (d, J=25.1 Hz, (CH)), 111.9 (d, J=26.6 Hz, CH)), 114.0 (d, J=9.8 Hz, (CH), 126.2 (C), 134.7 (C), 134.9 (CH), 160.0 (d, J=235.1 Hz, C), 168.8 (C), 175.5 (CO) ppm.

6-Fluoro-1H-indole-3-carboxylic acid (2g)

Commercially available, for example:
American Custom Chemicals Corp. P O Box 262527 San Diego, Calif. 92196-2527 USA Its synthesis from 1-(6-fluoro-1H-indol-3-yl)-2,2,2-trifluoroethanone (hg) was described in the patent: A. J. Ratcliffe et al. PCT Int. Appl., 2006038001, 13 Apr. 2006.

The compound (2g) can be prepared by the method described in the invention.

5-Iodo-1H-indole-3-carboxylic acid (2h)

Commercially available, for example:
American Custom Chemicals Corp. P O Box 262527 San Diego, Calif. 92196-252 USA Its synthesis from 1-(5-iodo-1H-indol-3-yl)-2,2,2-trifluoroethanone (hh) was described in the patent: C. Seong et al., Eur. Pat. Appl., 2108649, 14 Oct. 2009. Experimental conditions: NaOH, $H_2O$, 3 h, 60° C.

This compound (2h) can be prepared by the method described in the invention.

6-Iodo-1H-indole-3-carboxylic acid (2i)

The compound (2i) can be prepared by the method described in the invention.

4-Bromo-1H-indole-3-carboxylic acid (2j)

Commercially available for example:
Best PharmaTech, Inc. P O Box 59394 Schaumburg, Ill. 60159 USA The compound (2j) can be prepared by the method described in the invention.

7-bromo-1H-indole-3-carboxylic acid (2k)

Commercially available for examples:
American Custom Chemicals Corp. P O Box 262527 San Diego, Calif. 92196-2527 USA or Alchem Pharmtech, Inc. 160 Liberty Street, Bldg 4A Metuchen, N.J. 08840 USA The compound (2k) can be prepared by the method described in the invention.

Example 2: Preparation of Monoprotected Indolic 1,2-Diamines

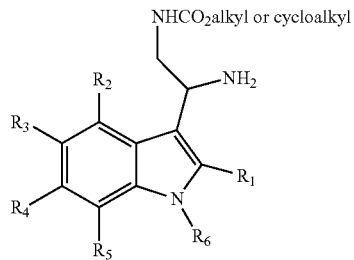

2.1 Synthesis of Indolic N-Hydroxylamines (Xa-l)

Indolic N-hydroxylamines (1) were prepared according the procedures described in the following articles: J.-N. Denis, H. Mauger, Y. Vallée Tetrahedron Lett. 1997, 38, 8515-8518; H. Chalaye-Mauger, J.-N. Denis, M.-T. Averbuch-Pouchot, Y. Vallée Tetrahedron 2000, 56, 791-804; X. Guinchard, Y. Vallée, J.-N. Denis, <<Total synthesis of marine sponge bis(indole) alkaloids of the topsentin class>>, J. Org. Chem. 2007, 72, 3972-3975; X. Guinchard, Y. Vallée, J.-N. Denis, <<Total syntheses of brominated marine sponge alkaloids>>, Org. Lett. 2007, 9, 3761-3764; 0. N. Burchak, E. Le Pihive, L. Maigre, X. Guinchard, P. Bouhours, C. Jolivalt, D. Schneider, M. Maurin, J.-M. Paris, J.-N. Denis, <<Synthesis and evaluation of 1-(1H-indole-3-yl)ethanamine derivatives as new antibacterial agents>>, Bioorg. Med. Chem. 2011, 19, 3204-3215 and in the patent: J.-N. Denis, X. Guinchard, N. Moreau, L. Neuville, Y. Vallée. <<Synthesis of new indole derivatives, their preparation processes, and their antibacterial uses>>, FR 2912133 A1; WO 2008110690 A2.

The procedure used for the NHBoc protected compound is representative of the other NH protected compounds.

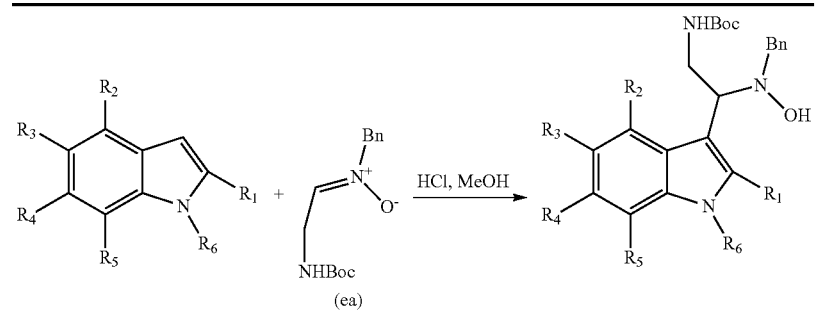

(aa): $R_1$-$R_6$ = H, alkyl = t-Bu
(ab): $R_3$ = Br and $R_1$, $R_2$, and $R_4$-$R_6$ = H, alkyl = t-Bu
(ac): $R_4$ = Br and $R_1$-$R_3$, and $R_5$, $R_6$ = H, alkyl = t-Bu (Xa): $R_1$-$R_6$ = H, alkyl = t-Bu
(Xb): $R_3$ = Br and $R_1$, $R_2$, and $R_4$-$R_6$ = H, alkyl = t-Bu
(Xc): $R_4$ = Br and $R_1$-$R_3$, and $R_5$, $R_6$ = H, alkyl = t-Bu

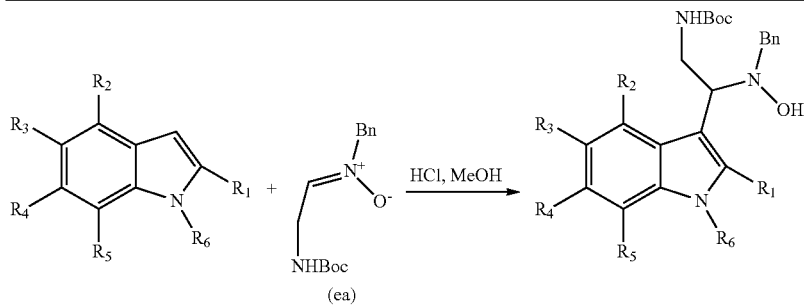

| | |
|---|---|
| (ad): $R_3$ = Cl and $R_1$, $R_2$, and $R_4$-$R_6$ = H, alkyl = tBu | (Xd): $R_3$ = Cl and $R_1$, $R_2$, and $R_4$-$R_6$ = H, alkyl = tBu |
| (ae): $R_4$ = Cl and $R_1$-$R_3$, and $R_5$, $R_6$ = H, alkyl = t-Bu | (Xe): $R_4$ = Cl and $R_1$-$R_3$, and $R_5$, $R_6$ = H, alkyl = t-Bu |
| (af): $R_3$ = F and $R_1$, $R_2$, and $R_4$-$R_6$ = H, alkyl = t-Bu | (Xf): $R_3$ = F and $R_1$, $R_2$, and $R_4$-$R_6$ = H, alkyl = t-Bu |
| (ag): $R_4$ = F and $R_1$-$R_3$, and $R_5$, $R_6$ = H, alkyl = t-Bu | (Xg): $R_4$ = F and $R_1$-$R_3$, and $R_5$, $R_6$ = H, alkyl = t-Bu |
| (ah): $R_3$ = I and $R_1$, $R_2$, and $R_4$-$R_6$ = H, alkyl = t-Bu | (Xh): $R_3$ = I and $R_1$, $R_2$, and $R_4$-$R_6$ = H, alkyl = t-Bu |
| (ai): $R_4$ = I and $R_1$-$R_3$, and $R_5$, $R_6$ = H, alkyl = t-Bu | (Xi): $R_4$ = I and $R_1$-$R_3$, and $R_5$, $R_6$ = H, alkyl = t-Bu |
| (aj): $R_2$ = Br and $R_1$ and $R_3$-$R_6$ = H, alkyl = t-Bu | (Xj): $R_2$ = Br and $R_1$ and $R_3$-$R_6$ = H, alkyl = t-Bu |
| (ak): $R_5$ = Br and $R_1$-$R_4$ and $R_6$ = H, alkyl = t-Bu | (Xk): $R_5$ = Br and $R_1$-$R_4$ and $R_6$ = H, alkyl = t-Bu |
| (al): $R_1$ = Br and $R_2$-$R_6$ = H, alkyl = t-Bu | (Xl): $R_1$ = Br and $R_2$-$R_6$ = H, alkyl = t-Bu | tert-Butyl 2-(benzyl(hydroxy)amino)-2-(1H-indol-3-yl)ethylcarbamate (Xa)

A cold solution of hydrochloric acid was prepared by reaction of 1.12 mL (1.25 g, 15.91 mmol) of freshly distilled acetyl chloride with 40 mL of dry methanol. This solution was stirred at 0° C. during 15 min and then was added a mixture of both indole (aa) (0.93 g, 7.95 mmol) and nitrone (ea) (2.1 g, 7.95 mmol) in 20 mL of methanol. The reaction was stirred at 0° C. during 1 hour to completion. A saturated aqueous solution of $NaHCO_3$ was then added. The mixture was extracted 3 times with $CH_2Cl_2$ and the collected organic layers were washed with brine and dried over anhydrous $MgSO_4$. The solvent was removed under vacuum. The crude product was purified by trituration with pentane. The product (1a) was obtained as a white solid (3.0 g, 7.87 mmol). Yield: 99%.

Mp: 145-146° C. IR (neat): 3416, 3341, 3329, 3090, 3060, 3031, 2978, 2932, 2875, 2839, 1693, 1680, 1514, 1505, 1497, 1455, 1434, 1393, 1367, 1280, 1167, 1100 $cm^{-1}$. $^1H$ NMR ($CDCl_3$, 200 MHz): δ=1.51 (s, 9H, C($CH_3$)$_3$), 3.50-3.70 (m, 2H, $CH_2N$), 3.75 (ABq, $J_{AB}$=14.4 Hz, $δ_A$-$δ_B$=38.9 Hz, 2H, $CH_2Ph$), 4.14 (t, J=5.4 Hz, 1H, CHN), 4.88 (t, J=6.5 Hz, 1H, NHBoc), 6.56 (s, 1H, OH), 7.08-7.39 (m, 9H, H arom), 7.66 (d, J=7.5 Hz, 1H, H arom), 8.36 (s, 1H, NH indole). $^{13}C$ NMR ($CDCl_3$, 75.5 MHz): δ=28.5 (C($CH_3$)$_3$), 43.7 ($CH_2$), 60.6 ($CH_2$), 63.8 (CHN), 79.7 (C($CH_3$)$_3$), 111.2 (CH arom), 112.3 (C arom), 119.6 (CH arom), 119.7 (CH arom), 122.2 (CH arom), 123.4 (CH arom), 126.7 (CH arom), 127.2 (C arom), 128.0 (CH arom), 128.6 (CH arom), 136.0 (C arom), 139.0 (C arom), 157.7 (C=O). LRMS (DCI, $NH_3$+isobutane): m/z=382 [(M+H)$^+$]. Anal. calcd for $C_{22}H_{27}N_3O_3$: C, 69.27; H, 7.13; N, 11.02. Found: C, 69.23; H, 7.36; N, 10.77.

2.2. Synthesis of Halo-Indolic N-Hydroxylamines (Xb-l)

General Procedure

A cold solution of hydrochloric acid was prepared by reaction of 0.143 mL (157 mg, 2.0 mmol) of freshly distilled acetyl chloride with 5 mL of dry methanol. This solution was stirred at 0° C. during 15 min and was added to a mixture of both nitrone (ea) (1.0 mmol) and indole (aa-l) (1.0 mmol) in 5 mL of dry methanol. The reaction mixture was stirred at 0° C. during 2 hours to completion. A saturated aqueous solution of $NaHCO_3$ was then added. The mixture was extracted with $CH_2Cl_2$ (3×10 mL) and the collected organic layers were washed with brine, dried over anhydrous $Na_2SO_4$, filtered and concentrated under vacuum. Column chromatography using EtOAc-pentane (from 1/99 to 40/60) yielded pure products (Xb-l).

tert-Butyl 2-(benzyl(hydroxy)amino)-2-(5-bromo-1H-indol-3-yl)ethylcarbamate (Xb)

The compound (Xb) (385 mg, 0.837 mmol) was obtained from nitrone (ea) (264 mg, 1.0 mmol) and 5-bromoindole (ab) (196 mg, 1.0 mmol) as a white solid. Yield: 84%.

Mp: 170-171° C. IR (neat): 3420, 3339, 2980, 2931, 1690, 1518, 1453, 1363, 1167 $cm^{-1}$. $^1H$ NMR ($CDCl_3$, 300 MHz): δ=1.53 (s, 9H, C($CH_3$)$_3$), 3.5-3.7 (m, 2H, $CH_2N$), 3.7 (ABq, $J_{AB}$=13.7 Hz, $δ_A$-$δ_B$=45.3 Hz, 2H, $CH_2Ph$), 4.03 (t, J=5.5 Hz, 1H, CHN), 4.87 (t, J=6.9 Hz, 1H, NHBoc), 6.72 (s, 1H, OH), 7.15-7.35 (m, 8H, H arom), 7.84 (s, 1H, H arom), 8.37 (s, 1H, NH indole) ppm. $^{13}C$ NMR ($CDCl_3$, 75.5 MHz): δ=28.4 (C($\underline{C}H_3$)$_3$), 44.0 ($CH_2$), 60.5 ($CH_2Ph$), 63.9 (CHN), 80.0 ($\underline{C}(CH_3)_3$), 112.7 (CH arom), 113.1 (C arom), 122.6 (CH arom), 123.2 (C arom), 124.6 (CH arom), 125.1 (CH arom), 126.8 (CH arom), 128.1 (CH arom), 128.6 (CH arom), 128.8 (C arom), 134.6 (C arom), 138.7 (C arom), 157.8 (C=O)

ppm. LRMS (DCI, NH₃+isobutane): m/z=460 and 462 [(M+H)⁺]. Anal. calcd for $C_{22}H_{26}N_3O_3Br$: C, 57.40, H, 5.69, N, 9.13. Found: C, 57.07, H, 5.65, N, 9.22.

tert-Butyl 2-(benzyl(hydroxy)amino)-2-(6-bromo-1H-indol-3-yl)ethylcarbamate (Xc)

The compound (Xc) (400 mg, 0.87 mmol) was obtained from nitrone (ea) (264 mg, 1.0 mmol) and 6-bromoindole (ac) (196 mg, 1.0 mmol) as a white solid. Yield: 87%.

Mp: 150° C. IR (neat): 3418, 3328, 3031, 2980, 2932, 1687, 1615, 1516, 1455, 1395, 1366, 1336, 1288, 1251, 1166, 1050, 1029, 897, 866, 846, 803, 738, 701 cm⁻¹. ¹H NMR (CDCl₃, 300 MHz): δ=1.50 (s, 9H, C(CH₃)₃), 3.55-3.70 (m, 2H, CHN), 3.72 (ABq, $J_{AB}$=14.0 Hz, $δ_A$-$δ_B$=57.8 Hz, 2H, CH₂Ph), 4.07 (t, J=5.7 Hz, 1H, CHN), 4.78-4.91 (def t, 1H, NHBoc), 6.52 (s, 1H, OH), 7.18-7.35 (m, 7H, H arom), 7.51-7.55 (m, 2H, H arom), 8.22 (s, 1H, NH indole) ppm. ¹³C NMR (CDCl₃, 75.5 MHz): δ=28.4 (C(CH₃)₃), 43.9 (CH₂), 60.5 (CH₂), 63.2 (CHN), 79.9 (C(CH₃)₃), 112.2 (C arom), 114.2 (CH arom), 115.8 (CH arom), 120.9 (CH arom), 122.9 (CH arom), 124.1 (CH arom), 126.0 (C arom), 126.8 (CH arom), 128.1 (CH arom), 128.5 (CH arom), 136.7 (C arom), 138.8 (C arom), 157.7 (C=O) ppm. LRMS (DCI, NH₃+isobutane): m/z=460 and 462 [M+H]⁺]. Anal. calcd for $C_{22}H_{26}N_3O_3Br$: C, 57.40; H, 5.69; N, 9.13. Found: C, 57.09; H, 5.87; N, 9.05.

tert-Butyl 2-(benzyl(hydroxy)amino)-2-(5-chloro-1H-indol-3-yl)ethylcarbamate (Xd)

The compound (Xd) (360 mg, 0.867 mmol) was obtained from nitrone (ea) (264 mg, 1.0 mmol) and 5-chloroindole (ad) (152 mg, 1.0 mmol) as a white solid. Yield: 87%.

IR (neat): 3315, 2970, 1655, 1520, 1295, 1165, 910, 895, 790, 735, 695 cm⁻¹. ¹H NMR (300 MHz, CDCl₃-CD₃OD): δ=1.48 (s, 9H), 3.58-3.63 (m, 2H), 3.60 (d, J=13.7 Hz, 1H), 3.81 (d, J=13.7 Hz, 1H), 4.07 (t, J=5.4 Hz, 1H), 5.37 (t, J=6.2 Hz, 1H), 7.11 (dd, J=2.0 and 8.6 Hz, 1H), 7.20-7.37 (m, 8H), 7.68 (br s, 1H) ppm. ¹³C NMR (75.5 MHz, CDCl₃-CD₃OD): δ=29.8 (3C), 45.3, 59.0, 63.7, 81.3, 113.9 (2C), 120.7, 123.5 (2C), 126.4 (2C), 126.8, 128.4, 129.5 (2C), 130.3, 136.4, 139.7, 158.0 ppm. LRMS (ESI): m/z (%)=438 (22) [(M+Na)⁺], 416 (100) [(M+H)⁺], 293 (18), 237 (89), 193 (16).

tert-Butyl 2-(benzyl(hydroxy)amino)-2-(6-chloro-1H-indol-3-yl)ethylcarbamate (Xe)

The compound (Xe) (340 mg, 0.819 mmol) was obtained from nitrone (ea) (264 mg, 1.0 mmol) and 6-chloroindole (ae) (152 mg, 1.0 mmol) as a white solid. Yield: 82%.

IR (neat): 3405, 3360, 2975, 2850, 1655, 1520, 1455, 1365, 1290, 1160, 1105, 905, 800, 735, 695 cm⁻¹. ¹H NMR (300 MHz, CDCl₃): δ=1.50 (s, 9H), 3.54-3.63 (m, 2H), 3.62 (d, J=14.0 Hz, 1H), 3.80 (d, J=14.0 Hz, 1H), 4.07 (t, J=5.6 Hz, 1H), 4.92 (t, J=6.2 Hz, 1H), 6.52 (br s, 1H), 7.08 (dd, J=1.7 and 8.5 Hz, 1H), 7.18-7.26 (m, 6H), 7.33 (d, J=1.4 Hz, 1H), 7.55 (d, J=8.6 Hz, 1H), 8.45 (br s, 1H) ppm. ¹³C NMR (75 MHz, CDCl₃): δ=28.5 (3C), 43.7, 60.6, 64.7, 79.9, 111.2 (2C), 120.4 (2C), 120.5, 124.2, 125.7, 126.8, 128.1 (2C), 128.6, 136.3, 138.7, 157.7 ppm. LRMS (ESI): m/z (%)=438 (17) [(M+Na)⁺], 416 (97) [(M+H)⁺], 293 (17), 237 (100), 193 (9).

tert-Butyl 2-(benzyl(hydroxy)amino)-2-(5-fluoro-1H-indol-3-yl)ethylcarbamate (Xf)

The compound (Xf) (390 mg, 0.977 mmol) was obtained from nitrone (ea) (264 mg, 1.0 mmol) and 5-fluoroindole (at) (135 mg, 1.0 mmol) as a white solid. Yield: 98%.

IR (neat): 3410, 3300, 2975, 2890, 1655, 1540, 1490, 1455, 1290, 1165, 935, 845, 745, 695 cm⁻¹. ¹H NMR (300 MHz, CD₃OD): δ=1.43 (s, 9H), 3.49-3.81 (m, 4H), 4.13 (t, J=5.4 Hz, 1H), 6.90 (dt, J=2.4 and 9.1 Hz, 1H), 7.20-7.40 (m, 8H) ppm. ¹³C NMR (75.5 MHz, CD₃OD): δ=28.8 (3C), 44.2, 60.9, 62.4, 78.2 (C), 103.2 (d, J=24.8 Hz), 110.6 (d, J=26.4 Hz), 113.0 (d, J=9.4 Hz), 124.3, 127.3, 127.8, 129.0 (2C), 130.2 (2C), 132.9, 136.7, 140.3, 156.7, 159.3 (d, J=236.1 Hz). ¹⁹F NMR (282 MHz, CD₃OD): δ=−124.2 (dt, J=4.8 and 9.8 Hz, 1F) ppm. LRMS (ESI): m/z (%)=422 (21) [(M+Na)⁺], 400 (97) [(M+H)⁺], 277 (17), 221 (100), 177 (20).

tert-Butyl 2-(benzyl(hydroxy)amino)-2-(6-fluoro-1H-indol-3-yl)ethylcarbamate (Xg)

The compound (Xg) (340 mg, 0.85 mmol) was obtained from nitrone (ea) (264 mg, 1.0 mmol) and 6-fluoroindole (ag) (135 mg, 1.0 mmol) as a white solid. Yield: 85%.

IR (neat): 3410, 3365, 2975, 2875, 1655, 1625, 1520, 1290, 1165, 1140, 1095, 910, 830, 800, 735, 695 cm⁻¹. ¹H NMR (300 MHz, CDCl₃): δ=1.50 (s, 9H), 3.54-3.63 (m, 2H), 3.62 (d, J=14.0 Hz, 1H), 3.83 (d, J=14.0 Hz, 1H), 4.08 (t, J=5.7 Hz, 1H), 4.92 (t, J=6.8 Hz, 1H), 6.50 (br s, 1H), 6.88 (dt, J=2.3 and 9.4 Hz, 1H), 7.02 (dd, J=2.0 and 9.6 Hz, 1H), 7.18-7.27 (m, 6H), 7.56 (dd, J=5.3 and 8.7 Hz, 1H), 8.42 (br s, 1H) ppm. ¹³C NMR (75.5 MHz, CDCl₃): δ=28.7 (3C), 44.0, 60.9, 64.0, 80.1 (C), 97.7 (d, J=26.2 Hz), 108.7 (d, J=24.4 Hz), 120.7 (d, J=10.4 Hz), 123.9, 124.0, 127.1, 128.3 (2C), 128.8 (2C), 132.3, 136.3, 138.9, 158.7, 160.3 (d, J=238.1 Hz) ppm. ¹⁹F NMR (282 MHz, CDCl₃): δ=−125.0 (dt, J=4.7 and 9.6 Hz, 1F) ppm. LRMS (ESI): m/z (%)=422 (58) [(M+Na)⁺], 400 (94) [(M+H)⁺], 277 (20), 221 (100), 173 (12).

tert-Butyl 2-(benzyl(hydroxy)amino)-2-(5-iodo-1H-indol-3-yl)ethylcarbamate (Xh)

The compound (Xh) (420 mg, 0.828 mmol) was obtained from nitrone (ea) (264 mg, 1.0 mmol) and 5-iodoindole (ah) (243 mg, 1.0 mmol) as a white solid. Yield: 83%.

IR (neat): 3315, 2960, 1660, 1525, 1455, 1365, 1295, 1165, 910, 880, 790, 740, 695 cm⁻¹. ¹H NMR (300 MHz, CDCl₃-CD₃OD): δ=1.48 (s, 9H), 3.57-3.61 (m, 2H), 3.59 (d, J=14.0 Hz, 1H), 3.83 (d, J=14.0 Hz, 1H), 4.07 (t, J=5.8 Hz, 1H), 5.47 (br s, 1H), 7.18-7.30 (m, 7H), 7.41 (dd, J=1.6 and 8.5 Hz, 1H), 8.03 (s, 1H) ppm. ¹³C NMR (75.5 MHz, CDCl₃-CD₃OD): δ=29.9 (3C), 44.3, 59.1, 63.6, 84.2 (C), 97.8, 115.1 (2C), 123.7, 124.5, 126.4, 126.8, 128.2, 129.6 (2C), 130.4, 131.5, 132.4, 134.9, 138.2, 157.5 ppm. LRMS (ESI): m/z (%)=530 (33) [(M+Na)⁺], 508 (100) [(M+H)⁺], 329 (63).

tert-Butyl 2-(benzyl(hydroxy)amino)-2-(6-iodo-1H-indol-3-yl)ethylcarbamate (Xi)

The compound (Xi) can be obtained from nitrone (ea) and 6-iodoindole (ai) according the procedure described in the invention.

tert-Butyl 2-(benzyl(hydroxy)amino)-2-(4-bromo-1H-indol-3-yl)ethylcarbamate (Xj)

The compound (Xj) (370 mg, 0.806 mmol) was obtained from nitrone (ea) (264 mg, 1.0 mmol) and 4-bromoindole (aj) (196 mg, 1.0 mmol) as a white solid. Yield: 81%.

IR (neat): 3375, 3290, 2980, 2830, 1655, 1560, 1455, 1330, 1290, 1165, 1120, 910, 730, 695 cm$^{-1}$. $^1$H NMR (300 MHz, CD$_3$OD): δ=1.43 (s, 9H), 3.51-3.69 (m, 2H), 3.69 (d, J=14.3 Hz, 1H), 3.88 (d, J=14.3 Hz, 1H), 5.29 (t, J=6.0 Hz, 1H), 7.00 (t, J=7.8 Hz, 1H), 7.19-7.31 (m, 6H), 7.42 (d, J=8.1 Hz, 1H), 7.60 (s, 1H) ppm. $^{13}$C NMR (75.5 MHz, CD$_3$OD): δ=28.9 (3C), 42.7, 62.2, 64.1, 80.2 (C), 112.1, 114.3, 123.0, 125.1, 125.7, 126.6, 126.9, 127.3, 129.0 (2C), 130.0, 132.8, 135.8, 138.9, 156.4 ppm. LRMS (ESI): m/z (%)=482 (26) [(M+Na)$^+$], 460 (100) [(M+H)$^+$], 281 (37).

tert-Butyl 2-(benzyl(hydroxy)amino)-2-(7-bromo-1H-indol-3-yl)ethylcarbamate (Xk)

The compound (Xk) can be obtained from nitrone (ea) and 6-iodoindole (ak) according the procedure described in this description.

tert-Butyl 2-(benzyl(hydroxy)amino)-2-(2-bromo-1H-indol-3-yl)ethylcarbamate (Xl)

The compound (Xl) can be obtained from nitrone (ea) and 6-iodoindole (al) according the procedure described in the invention.

2.3 Synthesis of Indolic Amines (1a-l)

Path A: $R_1$-$R_6$=H, alkyl=t-Bu

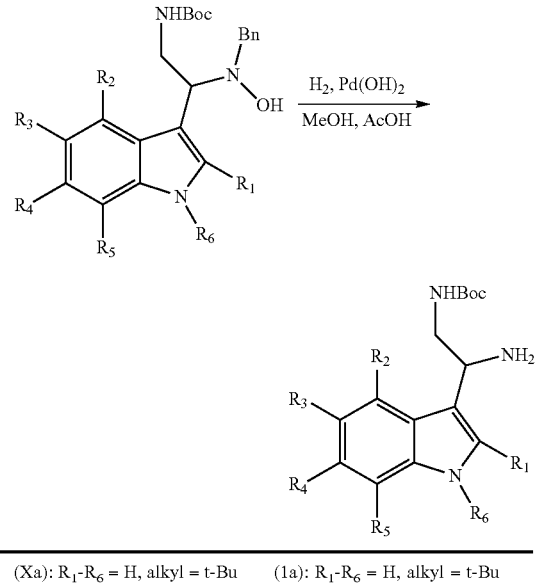

(Xa): $R_1$-$R_6$ = H, alkyl = t-Bu          (1a): $R_1$-$R_6$ = H, alkyl = t-Bu

2.3.1 Synthesis of Indolic Nitrones (Ya-l)

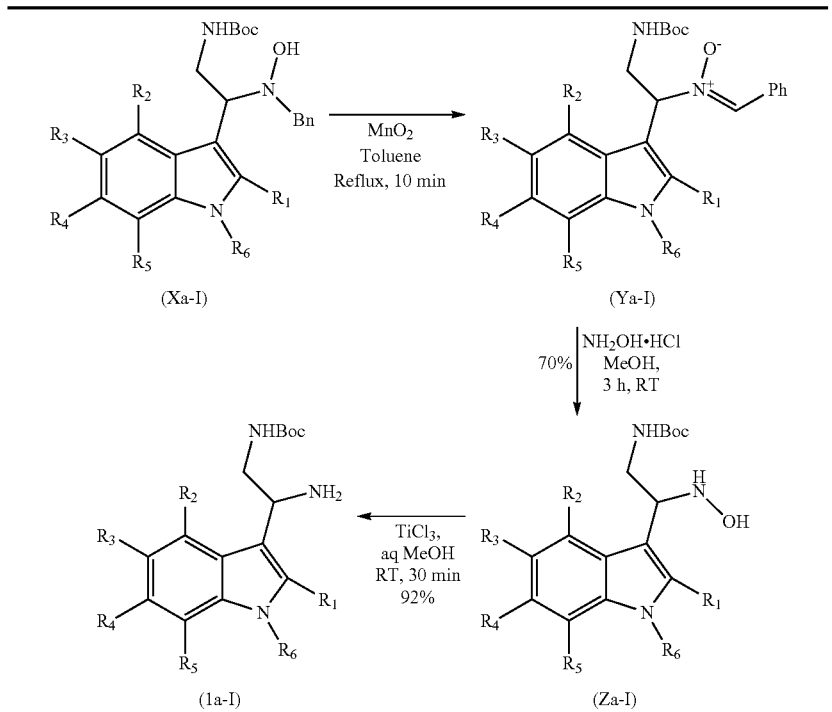

| (Xa): $R_1$-$R_6$ = H, alkyl = t-Bu | (Ya): $R_1$-$R_6$ = H, alkyl = t-Bu | (Za): $R_1$-$R_6$ = H, alkyl = t-Bu | (1a): $R_1$-$R_6$ = H, alkyl = t-Bu |
|---|---|---|---|
| (Xb): $R_3$ = Br and $R_1$, $R_2$, and $R_4$-$R_6$ = H, alkyl = t-Bu | (Yb): $R_3$ = Br and $R_1$, $R_2$, and $R_4$-$R_6$ = H, alkyl = t-Bu | (Zb): $R_3$ = Br and $R_1$, $R_2$, and $R_4$-$R_6$ = H, alkyl = t-Bu | (1b): $R_3$ = Br and $R_1$, $R_2$, and $R_4$-$R_6$ = H, alkyl = t-Bu |
| (Xc): $R_4$ = Br and $R_1$-$R_3$, and $R_5$, $R_6$ = H, alkyl = t-Bu | (Yc): $R_4$ = Br and $R_1$-$R_3$, and $R_5$, $R_6$ = H, alkyl = t-Bu | (Zc): $R_4$ = Br and $R_1$-$R_3$, and $R_5$, $R_6$ = H, alkyl = t-Bu | (1c): $R_4$ = Br and $R_1$-$R_3$, and $R_5$, $R_6$ = H, alkyl = t-Bu |

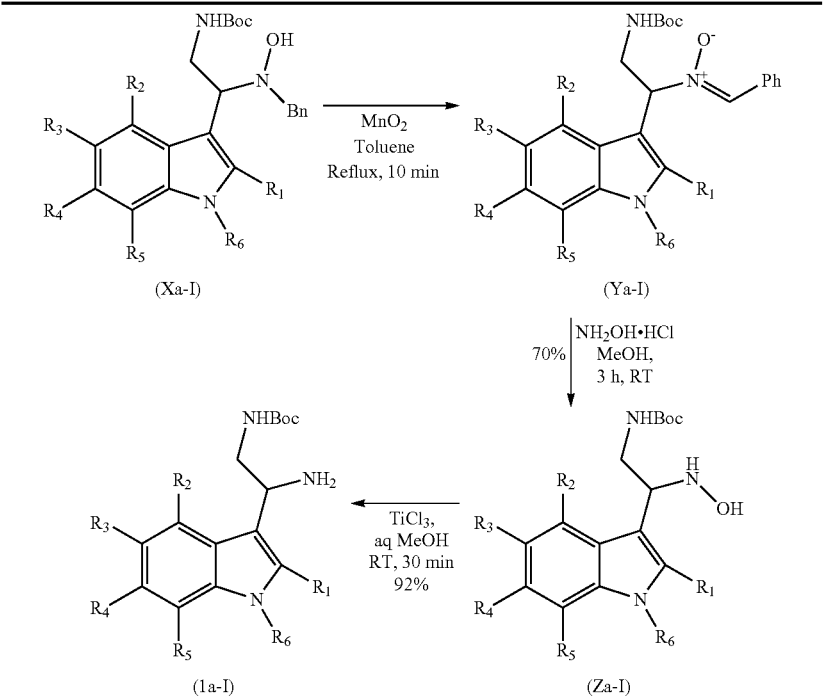

(Xd): $R_3$ = Cl and $R_1$, $R_2$, and $R_4$-$R_6$ = H, alkyl = t-Bu
(Yd): $R_3$ = Cl and $R_1$, $R_2$, and $R_4$-$R_6$ = H, alkyl = t-Bu
(Zd): $R_3$ = Cl and $R_1$, $R_2$, and $R_4$-$R_6$ = H, alkyl = t-Bu
(1d): $R_3$ = Cl and $R_1$, $R_2$, and $R_4$-$R_6$ = H, alkyl = t-Bu (Xe): $R_4$ = Cl and $R_1$-$R_3$, and $R_5$, $R_6$ = H, alkyl = t-Bu
(Ye): $R_4$ = Cl and $R_1$-$R_3$, and $R_5$, $R_6$ = H, alkyl = t-Bu
(Ze): $R_4$ = Cl and $R_1$-$R_3$, and $R_5$, $R_6$ = H, alkyl = t-Bu
(1e): $R_4$ = Cl and $R_1$-$R_3$, and $R_5$, $R_6$ = H, alkyl = t-Bu (Xf): $R_3$ = F and $R_1$, $R_2$, and $R_4$-$R_6$ = H, alkyl = t-Bu
(Yf): $R_3$ = F and $R_1$, $R_2$, and $R_4$-$R_6$ = H, alkyl = t-Bu
(Zf): $R_3$ = F and $R_1$, $R_2$, and $R_4$-$R_6$ = H, alkyl = t-Bu
(1f): $R_3$ = F and $R_1$, $R_2$, and $R_4$-$R_6$ = H, alkyl = t-Bu (Xg): $R_4$ = F and $R_1$-$R_3$, and $R_5$, $R_6$ = H, alkyl = t-Bu
(Yg): $R_4$ = F and $R_1$-$R_3$, and $R_5$, $R_6$ = H, alkyl = t-Bu
(Zg): $R_4$ = F and $R_1$-$R_3$, and $R_5$, $R_6$ = H, alkyl = t-Bu
(1g): $R_4$ = F and $R_1$-$R_3$, and $R_5$, $R_6$ = H, alkyl = t-Bu (Xh): $R_3$ = I and $R_1$, $R_2$, and $R_4$-$R_6$ = H, alkyl = t-Bu
(Yh): $R_3$ = I and $R_1$, $R_2$, and $R_4$-$R_6$ = H, alkyl = t-Bu
(Zh): $R_3$ = I and $R_1$, $R_2$, and $R_4$-$R_6$ = H, alkyl = t-Bu
(1h): $R_3$ = I and $R_1$, $R_2$, and $R_4$-$R_6$ = H, alkyl = t-Bu (Xi): $R_4$ = I and $R_1$-$R_3$, and $R_5$, $R_6$ = H, alkyl = t-Bu
(Yi): $R_4$ = I and $R_1$-$R_3$, and $R_5$, $R_6$ = H, alkyl = t-Bu
(Zi): $R_4$ = I and $R_1$-$R_3$, and $R_5$, $R_6$ = H, alkyl = t-Bu
(1i): $R_4$ = I and $R_1$-$R_3$, and $R_5$, $R_6$ = H, alkyl = t-Bu (Xj): $R_2$ = Br and $R_1$ and $R_3$-$R_6$ = H, alkyl = t-Bu
(Yj): $R_2$ = Br and $R_1$ and $R_3$-$R_6$ = H, alkyl = t-Bu
(Zj): $R_2$ = Br and $R_1$ and $R_3$-$R_6$ = H, alkyl = t-Bu
(1j): $R_2$ = Br and $R_1$ and $R_3$-$R_6$ = H, alkyl = t-Bu (Xk): $R_5$ = Br and $R_1$-$R_4$ and $R_6$ = H, alkyl = t-Bu
(Yk): $R_5$ = Br and $R_1$-$R_4$ and $R_6$ = H, alkyl = t-Bu
(Zk): $R_5$ = Br and $R_1$-$R_4$ and $R_6$ = H, alkyl = t-Bu
(1k): $R_5$ = Br and $R_1$-$R_4$ and $R_6$ = H, alkyl = t-Bu (Xl): $R_1$ = Br and $R_2$-$R_6$ = H, alkyl = t-Bu
(Yl): $R_1$ = Br and $R_2$-$R_6$ = H, alkyl = t-Bu
(Zl): $R_1$ = Br and $R_2$-$R_6$ = H, alkyl = t-Bu
(1l): $R_1$ = Br and $R_2$-$R_6$ = H, alkyl = t-Bu

2.3.2. Synthesis of Indolic Nitrones (Ya-l)

General Procedure

A stirred solution of indolic N-hydroxylamine (Xa-l) (1 equivalent) in toluene was warmed to 100° C. Five equivalents of manganese dioxide were then added. The resulting heterogeneous mixture was stirred at this temperature during 10 min. It was then cooled at room temperature and filtered on celite. Resulted heterogeneous solution was concentrated under vacuum. The obtained crude extract was purified by column chromatography on silica gel (previously treated by 2.5% of triethylamine) using EtOAc-pentane (from 5/95 to 90/10) affording pure product (Ya-l).

(Z)—N-Benzylidene-2-(tert-butoxycarbonylamino)-1-(1H-indol-3-yl)ethanamine N-oxide (Ya)

The compound (Ya) (560 mg, 1.48 mmol) was obtained from N-hydroxylamine (Xa) (724 mg, 1.9 mmol) and $MnO_2$ (827 mg, 9.5 mmol) as a beige foam. Yield: 78%.

Mp: 150° C. IR (neat): 3302, 3056, 2979, 2927, 1699, 1686, 1505, 1460, 1369, 1253, 1176 $cm^{-1}$. $^1$H NMR (300 MHz, $CDCl_3$): δ=1.43 (s, 9H, $C(CH_3)_3$), 3.78-3.95 (m, 1H, 1H of $CH_2$), 3.95-4.10 (m, 1H, 1H of $CH_2$), 5.49 (t, J=5.9 Hz, 1H, CHN), 5.6-5.7 (m, 1H, NHBoc), 7.11 (quint., J=7.1 Hz, 2H, H arom), 7.22 (d, J=2.0 Hz, 1H, H arom), 7.28 (d, J=4.8 Hz, 1H, H arom), 7.33-7.40 (m, 3H, H arom), 7.57 (s, 1H, H arom), 7.70 (d, J=7.0 Hz, 1H, H arom), 8.17-8.24 (m, 2H, H ortho of Ph), 8.92 (s, 1H, NH) ppm. $^{13}$C NMR (75.5 MHz, $CDCl_3$): δ=28.3 ($C(\underline{C}H_3)_3$), 42.9 ($CH_2$), 71.9 (CHN), 79.7 (C(CH$_3$)$_3$), 109.8 (C arom), 111.6 (CH arom), 118.6 (CH arom), 120.1 (CH arom), 122.3 (CH arom), 124.1 (CH arom), 125.9 (C arom), 128.4 (CH arom), 128.8 (CH arom), 130.3 (C arom), 130.5 (CH arom), 134.9 (CH=N), 136.1 (C arom), 156.3 (C=O) ppm. LRMS (DCI, NH$_3$+isobutane): m/z=380 [(M+H)$^+$], 279, 259, 258. HRMS (ESI) calcd for C$_{22}$H$_{25}$N$_3$O$_3$Na: 402.1794. Found: 402.1797 [(M+Na)$^+$].

(Z)—N-Benzylidene-2-(tert-butoxycarbonylamino)-1-(5-bromo-1H-indol-3-yl)ethanamine N-oxide (Yb)

The compound (Yb) (365 mg, 0.797 mmol) was obtained from N-hydroxylamine (Xb) (575 mg, 1.25 mmol) and MnO$_2$ (544 mg, 6.25 mmol) as a beige foam. Yield: 64%.
Mp: 128° C. IR (KBr): 3419, 3299, 3075, 2977, 2929, 1696, 1513, 1453, 1363, 1254, 1164, 887, 801 cm$^{-1}$. $^1$H NMR (300 MHz, CDCl$_3$): δ=1.42 (s, 9H, C(CH$_3$)$_3$), 3.72-3.83 (m, 1H, 1H of CH$_2$N), 3.93-4.10 (m, 1H, 1H of CH$_2$N), 5.39 (br s, 1H, NHBoc), 5.54 (br s, 1H, CHN), 6.99 (d, J=8.6 Hz, 1H, H arom), 7.12 (dd, J=1.7 and 8.6 Hz, 1H, H arom), 7.16 (d, J=2.4 Hz, 1H, H arom), 7.30-7.45 (m, 3H, H arom), 7.61 (s, 1H, CH=N), 7.77 (d, J=1.6 Hz, 1H, H arom), 8.15-8.30 (m, 2H, H arom), 9.57 (s, 1H, NH) ppm. $^{13}$C NMR (75.5 MHz, CDCl$_3$): δ=28.5 ((CH$_3$)$_3$C), 43.0 (CH$_2$N), 71.6 (CHN), 80.0 ((CH$_3$)$_3$C), 109.3 (C arom), 113.3 (CH arom), 113.5 (C arom), 121.1 (CH arom), 125.3 (CH arom), 125.7 (CH arom), 127.8 (C arom), 128.7 (CH arom), 129.1 (CH arom), 130.2 (C arom), 131.0 (CH arom), 134.9 (C arom), 135.5 (CH=N), 156.5 (C=O) ppm. LRMS (DCI, NH$_3$+ isobutane): m/z=458 and 460 [(M+H)$^+$], 298 and 300, 281 and 283. HRMS (ESI) calcd for C$_{22}$H$_{24}$N$_3$O$_3$$^{79}$BrNa: 380.0899. Found: 380.0901 [(M+Na)$^+$].

(Z)—N-Benzylidene-2-(tert-butoxycarbonylamino)-1-(6-bromo-1H-indol-3-yl)ethanamine N-oxide (Yc)

The compound (Yc) (430 mg, 0.94 mmol) was obtained from N-hydroxylamine (Xc) (598 mg, 1.30 mmol) and MnO$_2$ (566 mg, 6.50 mmol) as a beige foam. Yield: 72%.
Mp: 186° C. IR (neat): 3276, 2979, 2934, 1699, 1505, 1460, 1369, 1253, 1169, 807, 691 cm$^{-1}$. $^1$H NMR (300 MHz, CDCl$_3$): δ=1.43 (s, 9H, C(CH$_3$)$_3$), 3.70-3.80 (m, 1H, 1H of CH$_2$), 3.80-4.10 (m, 1H, 1H of CH$_2$), 5.40 (br s, 1H, CHN), 5.50-5.55 (m, 1H, NHBoc), 7.11-7.18 (m, 2H, H arom), 7.31 (d, J=1.4 Hz, 1H, H arom), 7.37-7.43 (m, 3H, Ph), 7.53 (d, J=8.4 Hz, 1H, H arom), 7.60 (s, 1H, H arom), 8.15-8.25 (m, 2H, 2H ortho Ph), 9.37 (s, 1H, NH indole) ppm. $^{13}$C NMR (75.5 MHz, CDCl$_3$): δ=28.3 (C(CH$_3$)$_3$), 42.7 (CH$_2$), 71.6 (CHN), 79.9 (C(CH$_3$)$_3$), 109.8 (C arom), 114.6 (CH arom), 115.8 (C arom), 119.8 (CH arom), 123.3 (CH arom), 128.6 (CH arom), 128.9 (CH arom), 130.0 (C arom), 130.9 (C arom), 135.5 (CH=N), 136.9 (C arom), 156.4 (C=O) ppm. LRMS (ESI): m/z=480 and 482 [(M+Na)$^+$], 458 and 460 [(M+H)$^+$], 281 and 283. HRMS (ESI) calcd for C$_{22}$H$_{24}$N$_3$O$_3$Na$^{79}$Br: 480.0899. Found: 480.0891 [(M+Na)$^+$].

(Z)—N-Benzylidene-2-(tert-butoxycarbonylamino)-1-(5-chloro-1H-indol-3-yl)ethanamine N-oxide (Yd)

The compound (Yd) (190 mg, 0.459 mmol) was obtained from N-hydroxylamine (Xd) (290 mg, 0.70 mmol) and MnO$_2$ (305 mg, 3.50 mmol) as a beige foam. Yield: 66%.
IR (neat): 3265, 2980, 1695, 1505, 1450, 1365, 1250, 1160, 1130, 895, 795, 750, 690 cm$^{-1}$. $^1$H NMR (300 MHz, CDCl$_3$): δ=1.41 (s, 9H), 3.71-3.76 (m, 1H), 3.95-4.03 (m, 1H), 5.39-5.55 (m, 2H), 6.90-6.98 (m, 2H), 7.02-7.10 (m, 1H), 7.30-7.39 (m, 3H), 7.59-7.62 (m, 2H), 8.20-8.24 (m, 2H), 9.70 (br s, 1H) ppm. $^{13}$C NMR (75 MHz, CDCl$_3$): δ=28.2 (3C), 42.7, 71.5, 79.8 (C), 108.9, 112.7, 117.8, 122.4, 125.6, 125.7, 126.9, 128.5 (2C), 128.9 (2C), 129.9, 130.8, 134.4, 135.3, 156.2 ppm. LRMS (ESI): m/z (%)=436 (40) [(M+Na)$^+$], 414 (34) [(M+H)$^+$], 293 (12), 237 (100), 193 (12).

(Z)—N-Benzylidene-2-(tert-butoxycarbonylamino)-1-(6-chloro-1H-indol-3-yl)ethanamine N-oxide (Ye)

The compound (Ye) (205 mg, 0.496 mmol) was obtained from N-hydroxylamine (Xe) (290 mg, 0.70 mmol) and MnO$_2$ (305 mg, 3.50 mmol) as a beige foam. Yield: 71%.
IR (neat): 3275, 2970, 1685, 1505, 1450, 1365, 1250, 1160, 1130, 905, 800, 750, 690 cm$^{-1}$. $^1$H NMR (300 MHz, CDCl$_3$): δ=1.41 (s, 9H), 3.67-3.80 (m, 1H), 3.94-4.06 (m, 1H), 5.43-5.58 (m, 2H), 6.93-7.07 (m, 3H), 7.33-7.38 (m, 3H), 7.48-7.53 (m, 1H), 7.61 (s, 1H), 8.20-8.24 (m, 2H), 9.65 (br s, 1H) ppm. $^{13}$C NMR (75 MHz, CDCl$_3$): δ=28.2 (3C), 42.6, 71.7, 79.8 (C), 109.3, 111.6, 119.2, 120.5, 124.4, 124.9, 127.9, 128.5 (2C), 128.9 (2C), 129.9, 130.8, 135.4, 136.4, 156.3 ppm. LRMS (ESI): m/z (%)=436 (81) [(M+Na)$^+$], 414 (33) [(M+H)$^+$], 293 (16), 237 (100), 193 (14).

(Z)—N-Benzylidene-2-(tert-butoxycarbonylamino)-1-(5-fluoro-1H-indol-3-yl)ethanamine N-oxide (Yf)

Compound (Yf) (210 mg, 0.529 mmol) was obtained from N-hydroxylamine (Xf) (320 mg, 0.80 mmol) and MnO$_2$ (348 mg, 4.00 mmol) as a beige foam. Yield: 66%.
IR (neat): 3465, 3295, 3060, 2970, 1685, 1505, 1455, 1370, 1240, 1175, 1150, 1130, 940, 785, 695, 670 cm$^{-1}$. $^1$H NMR (300 MHz, CDCl$_3$): δ=1.44 (s, 9H), 3.78-3.87 (m, 1H), 3.98-4.07 (m, 1H), 5.22-5.29 (m, 1H), 5.52-5.57 (m, 1H), 6.88 (dt, J=2.5 and 9.1 Hz, 1H), 7.18 (dd, J=4.4 and 9.0 Hz, 1H), 7.34-7.42 (m, 5H), 8.22-8.25 (m, 2H), 8.86 (br s, 1H, NH) ppm. $^{13}$C NMR (75.5 MHz, CDCl$_3$-CD$_3$OD): δ=27.9 (3C), 42.2, 71.4, 79.6 (C), 103.0 (d, J=23.1 Hz), 110.2 (d, J=26.3 Hz), 112.1 (d, J=9.6 Hz), 125.7, 128.2 (2C), 128.9 (2C), 129.6, 130.8, 132.4, 136.2, 156.7, 157.7 (d, J=234.7 Hz) ppm. $^{19}$F NMR (282 MHz, CDCl$_3$): δ=−123.3 (dt, J=4.3 and 9.3 Hz, 1F) ppm. LRMS (ESI): m/z (%)=420 (47) [(M+Na)$^+$], 398 (28) [(M+H)$^+$], 277 (15), 221 (100), 177 (15).

(Z)—N-Benzylidene-2-(tert-butoxycarbonylamino)-1-(6-fluoro-1H-indol-3-yl)ethanamine N-oxide (Yg)

Compound (Yg) (200 mg, 0.504 mmol) was obtained from indolic N-hydroxylamine (Xg) (280 mg, 0.70 mmol) and MnO$_2$ (305 mg, 3.50 mmol) as a beige foam. Yield: 72%.
IR (neat): 3370, 3160, 2985, 2910, 1685, 1530, 1455, 1320, 1270, 1135, 950, 835, 685, 675 cm$^{-1}$. $^1$H NMR (300 MHz, CDCl$_3$): δ=1.44 (s, 9H), 3.80-3.88 (m, 1H), 3.98-4.07 (m, 1H), 5.22-5.29 (m, 1H), 5.56-5.60 (m, 1H), 6.87 (dt, J=2.3 and 9.4 Hz, 1H), 6.95 (dd, J=2.1 and 9.4 Hz, 1H), 7.28 (d, J=2.3 Hz, 1H), 7.39-7.42 (m, 3H), 7.57 (s, 1H), 7.62-7.67 (m, 1H), 8.21-8.25 (m, 2H), 8.80 (br s, 1H, NH) ppm. $^{13}$C NMR (75.5 MHz, CDCl$_3$-CD$_3$OD): δ=27.6 (3C), 42.0, 71.4, 79.3 (C), 97.3 (d, J=23.8 Hz), 108.0 (d, J=25.0 Hz), 108.7, 118.7 (d, J=8.7 Hz), 122.3, 124.2 (d, J=3.4 Hz), 128.1 (2C), 128.9 (2C), 129.5, 130.6, 135.9 (d, J=12.6 Hz), 136.4, 156.6, 159.5 (d, J=237.2 Hz) ppm. $^{19}$F NMR (282 MHz, CDCl$_3$):

δ=−120.4 (m, 1F) ppm. LRMS (ESI): m/z (%)=420 (100) [(M+Na)$^+$], 398 (12) [(M+H)$^+$], 331 (8), 277 (6), 221 (36), 177 (5).

(Z)—N-Benzylidene-2-(tert-butoxycarbonylamino)-1-(5-iodo-1H-indol-3-yl)ethanamine N-oxide (Yh)

Compound (Yh) (240 mg, 0.475 mmol) was obtained from indolic N-hydroxylamine (Xh) (355 mg, 0.70 mmol) and MnO$_2$ (305 mg, 3.50 mmol) as a beige foam. Yield: 68%.

IR (neat): 3275, 2970, 2930, 1695, 1505, 1450, 1365, 1250, 1160, 880, 795, 750, 690 cm$^{-1}$. $^1$H NMR (300 MHz, CDCl$_3$): δ=1.42 (s, 9H), 3.71-3.81 (m, 1H), 3.94-4.05 (m, 1H), 5.29-5.40 (m, 1H), 5.48-5.55 (m, 1H), 6.87 (d, J=9.5 Hz, 1H), 7.10 (d, J=2.3 Hz, 1H), 7.28 (dd, J=1.4 and 8.6 Hz, 1H), 7.36-7.41 (m, 3H), 7.61 (s, 1H), 7.97 (s, 1H), 8.21-8.25 (m, 2H), 9.50 (br s, 1H) ppm. $^{13}$C NMR (75.5 MHz, CDCl$_3$): δ=28.3 (3C), 42.8, 71.3, 80.0 (C), 83.7, 108.7, 113.6, 125.1, 127.1, 128.4, 128.6 (2C), 128.9 (2C), 130.0, 130.6, 130.8, 135.1, 135.3, 156.2 ppm. LRMS (ESI): m/z (%)=528 (100) [(M+Na)$^+$], 506 (40) [(M+H)$^+$], 439 (6), 329 (86).

(Z)—N-Benzylidene-2-(tert-butoxycarbonylamino)-1-(6-iodo-1H-indol-3-yl)ethanamine N-oxide (Yi)

(Z)—N-Benzylidene-2-(tert-butoxycarbonylamino)-1-(4-bromo-1H-indol-3-yl)ethanamine N-oxide (Yj)

(Z)—N-Benzylidene-2-(tert-butoxycarbonylamino)-1-(7-bromo-1H-indol-3-yl)ethanamine N-oxide (Yk)

(Z)—N-Benzylidene-2-(tert-butoxycarbonylamino)-1-(2-bromo-1H-indol-3-yl)ethanamine N-oxide (Yl)

The compounds (Yi), (Yj), (Yk) and (Yl) can be obtained from indolic N-hydroxylamines (Xi), (Xj), (Xk) and (Xl) respectively according to the procedure described in this patent.

2.4 Synthesis of Indolic N-Hydroxylamines (Za-l)

General Procedure

To a stirred solution of one equivalent of indolic nitrone (Ya-l) in methanol, three equivalents of hydroxylamine hydrochloride were added. The resulting mixture was stirred during 1 hour at room temperature and then the solution was concentrated under vacuum. A saturated aqueous solution of NaHCO$_3$ was added. The mixture was then extracted with diethyl ether (3×10 mL) and the collected organic layers were washed with brine, dried over anhydrous Na$_2$SO$_4$, filtered, and concentrated under vacuum. The resulting crude mixture was purified by column chromatography using EtOAc-pentane (from 10/90 to 99/1) to afford the corresponding pure product (Za-l).

tert-Butyl 2-(1H-indol-3-yl)-2-(hydroxyamino)ethylcarbamate (Za)

Compound (Za) (265 mg, 0.91 mmol) was obtained from indolic nitrone (Ya) (531 mg, 1.40 mmol) and NH$_2$OH.HCl (292 mg, 4.20 mmol) as a beige foam. Yield: 65%. $^1$H NMR (300 MHz, CDCl$_3$): δ=1.43 (s, 9H, C(CH$_3$)$_3$), 3.4-3.6 (m, 1H, H of CH$_2$), 3.6-3.8 (m, 1H, H of CH$_2$), 4.37 (t, J=5.2 Hz, 1H, CHN), 5.04 (br s, 1H, NHBoc), 7.00 (s, 1H, H indole), 7.09 (t, J=7.0 Hz, 1H, H indole), 7.15 (t, J=7.0 Hz, 1H, H indole), 7.29 (d, J=7.9 Hz, 1H, H indole), 7.58 (d, J=7.9 Hz, 1H, H indole), 8.66 (s, 1H, NH indole) ppm. $^{13}$C NMR (75.5 MHz, CDCl$_3$): δ=28.4 (C(CH$_3$)$_3$), 42.5 (CH$_2$N), 58.5 (CHN), 79.7 (C(CH$_3$)$_3$), 111.4 (CH indole), 112.5 (C indole), 118.9 (CH indole), 119.6 (CH indole), 122.2 (CH indole), 122.8 (CH indole), 126.2 (C indole), 136.0 (C indole), 157.0 (C=O) ppm. LRMS (DCI, NH$_3$+isobutane): m/z=314 (M+Na)$^+$], 292 [(M+H)$^+$], 279, 203. HRMS (ESI) calcd for C$_{15}$H$_{22}$N$_3$O$_3$ [(M+H)$^+$]: 292.1661. Found: 292.1661.

tert-Butyl 2-(5-bromo-1H-indol-3-yl)-2-(hydroxyamino)ethylcarbamate (Zb)

Compound (Zb) (145 mg, 0.39 mmol) was obtained from nitrone (Yb) (320 mg, 0.70 mmol) and NH$_2$OH.HCl (146 mg, 2.10 mmol) as a beige foam. Yield: 56%.

Mp: 87° C. IR (KBr): 3419, 3307, 2977, 2936, 1692, 1516, 1456, 1366, 1254, 1172, 805 cm$^{-1}$. $^1$H NMR (300 MHz, CDCl$_3$): δ=1.43 (s, 9H, (CH$_3$)$_3$C), 3.35-3.65 (m, 2H, CH$_2$N), 4.25 (t, J=5.4 Hz, 1H, CHN), 5.11 (br s, 1H, NHBoc), 6.98 (d, J=1.7 Hz, 1H, H indole), 7.12 (d, J=8.7 Hz, 1H, H indole), 7.19 (dd, J=1.7 and 8.7 Hz, 1H, H indole), 7.72 (s, 1H, H indole), 9.05 (s, 1H, NH indole) ppm. $^{13}$C NMR (75.5 MHz, CDCl$_3$): δ=28.3 ((CH$_3$)$_3$C), 42.5 (CH$_2$N), 58.6 (CHN), 79.9 ((CH$_3$)$_3$C), 112.4 (C indole), 112.8 (C indole), 112.9 (CH indole), 121.7 (CH indole), 124.0 (CH indole), 124.9 (CH indole), 128.0 (C indole), 134.7 (C indole), 157.1 (C=O) ppm. LRMS (DCI, NH$_3$+ isobutane): m/z=370 and 372 [(M+H)$^+$], 298 and 300, 281 and 283. HRMS (ESI) calcd for C$_{15}$H$_{20}$N$_3$O$_3$$^{79}$BrNa [(M+Na)$^+$]: 392.0586. Found: 392.0591.

tert-Butyl 2-(6-bromo-1H-indol-3-yl)-2-(hydroxyamino)ethylcarbamate (Zc)

Compound (Zc) (170 mg, 0.46 mmol) was obtained from nitrone (Yc) (366 mg, 0.80 mmol) and NH$_2$OH.HCl (167 mg, 2.40 mmol) as a beige foam. Yield: 57%.

Mp: 80° C. IR (KBr): 3419, 3302, 2979, 2934, 1693, 1518, 1454, 1369, 1253, 911, 807, 736 cm$^{-1}$. $^1$H NMR (300 MHz, CDCl$_3$): δ=1.44 (s, 9H, C(CH$_3$)$_3$), 3.35-3.55 (m, 1H, H of CH$_2$N), 3.55-3.75 (m, 1H, H of CH$_2$N), 4.35 (t, J=5.1 Hz, 1H, CHN), 4.96 (br s, 1H, NHBoc), 7.06 (s, 1H, OH), 7.17 (dd, J=1.4 and 8.6 Hz, 1H, H indole), 7.46 (s, 1H, H indole), 7.47 (d, J=7.4 Hz, 1H, H indole), 8.66 (br s, 1H, NH indole) ppm. $^{13}$C NMR (75.5 MHz, CDCl$_3$): δ=28.4 (C(CH$_3$)$_3$), 42.4 (CH$_2$N), 58.5 (CHN), 80.0 (C(CH$_3$)$_3$), 112.9 (C indole), 114.4 (CH indole), 115.7 (C indole), 120.3 (CH indole), 123.0 (CH indole), 123.4 (CH indole), 125.2 (C indole), 136.9 (C indole), 157.1 (C=O) ppm. LRMS (ESI): m/z=370 and 372 [(M+H)$^+$], 281 and 283. HRMS (ESI) calcd for C$_{15}$H$_{21}$N$_3$O$_3$$^{79}$Br [(M+H)$^+$]: 370.0766. Found: 370.0768 and 372.0747.

tert-Butyl 2-(5-chloro-1H-indol-3-yl)-2-(hydroxyamino)ethylcarbamate (Zd)

Compound (Zd) (80 mg, 0.246 mmol) was obtained from indolic nitrone (Yd) (165 mg, 0.40 mmol) and NH$_2$OH.HCl (83 mg, 1.20 mmol) as a beige foam. Yield: 62%.

IR (neat): 3410, 3290, 2975, 2925, 1685, 1515, 1455, 1365, 1250, 1160, 895, 860, 795 cm$^{-1}$. $^1$H NMR (300 MHz, CDCl$_3$): δ=1.44 (s, 9H), 3.40-3.45 (m, 1H), 3.56-3.70 (m, 1H), 4.29 (t, J=5.3 Hz, 1H), 5.03 (br s, 1H), 7.05-7.10 (m, 2H), 7.20 (d, J=9.0 Hz, 1H), 7.59 (s, 1H), 8.84 (br s, 1H) ppm. $^{13}$C NMR (75.5 MHz, CDCl$_3$): δ=28.3 (3C), 42.5, 58.7, 79.9 (C), 112.4, 118.7, 122.5, 124.1, 125.3, 127.3, 134.5 (2C), 157.1 ppm. LRMS (ESI): m/z (%)=348 (14) [(M+Na)⁺], 326 (16) [(M+H)⁺], 237 (100), 193 (12).

tert-Butyl 2-(6-chloro-1H-indol-3-yl)-2-(hydroxyamino)ethylcarbamate (Ze)

Compound (Ze) (100 mg, 0.308 mmol) was obtained from nitrone (Ye) (165 mg, 0.40 mmol) and NH₂OH.HCl (83 mg, 1.20 mmol) as a beige foam. Yield: 77%.

IR (neat): 3415, 3280, 2975, 2925, 1685, 1510, 1455, 1365, 1250, 1160, 905, 800 cm⁻¹. ¹H NMR (300 MHz, CDCl₃): δ=1.43 (s, 9H), 3.40-3.62 (m, 2H), 4.30 (t, J=5.4 Hz, 1H), 5.06 (br s, 1H), 6.98-7.03 (m, 2H), 7.24-7.26 (m, 1H), 7.45 (d, J=9.0 Hz, 1H), 8.87 (br s, 1H, NH indole) ppm. ¹³C NMR (75.5 MHz, CDCl₃): δ=28.3 (3C), 42.4, 58.5, 79.9, 111.3, 119.8, 120.3, 123.3, 124.8, 128.0, 136.4 (2C), 157.1 ppm. LRMS (ESI): m/z (%)=348 (18) [(M+Na)⁺], 326 (14) [(M+H)⁺], 301 (12), 237 (100), 193 (11).

tert-Butyl 2-(5-fluoro-1H-indol-3-yl)-2-(hydroxyamino)ethylcarbamate (Zf)

Compound (Zf) (80 mg, 0.259 mmol) was obtained from indolic nitrone (Yf) (179 mg, 0.45 mmol) and NH₂OH.HCl (94 mg, 1.35 mmol) as a beige foam. Yield: 58%.

IR (neat): 3415, 3300, 2975, 2925, 1685, 1510, 1490, 1455, 1365, 1250, 1160, 935, 850, 795 cm⁻¹. ¹H NMR (300 MHz, CDCl₃): δ=1.42 (s, 9H), 3.43-3.50 (m, 1H), 3.55-3.48 (m, 1H), 4.28 (t, J=5.3 Hz, 1H), 5.04 (br s, 1H), 6.88 (dt, J=2.4 and 9.0 Hz, 1H), 7.07 (s, 1H), 7.19 (dd, J=4.4 and 8.8 Hz, 1H), 7.21-7.30 (m, 1H), 8.79 (br s, 1H, NH indole) ppm. ¹³C NMR (75.5 MHz, CDCl₃): δ=28.3 (3C), 42.4, 58.7, 79.9 (C), 104.1 (d, J=23.2 Hz), 110.6 (d, J=26.5 Hz), 112.0 (d, J=9.2 Hz), 124.4, 126.6 (d, J=10.2 Hz), 132.6 (2C), 157.2, 157.8 (d, J=236.7 Hz) ppm. ¹⁹F NMR (282 MHz, CDCl₃): δ=−124.1 (m, 1F) ppm. LRMS (ESI): m/z (%)=332 (49) [(M+Na)⁺], 310 (7) [(M+H)⁺], 239 (44), 221 (100).

tert-Butyl 2-(6-fluoro-1H-indol-3-yl)-2-(hydroxyamino)ethylcarbamate (Zg)

Compound (Zg) (50 mg, 0.162 mmol) was obtained from indolic nitrone (Yg) (159 mg, 0.40 mmol) and NH₂OH.HCl (83 mg, 1.20 mmol) as a beige foam. Yield: 40%.

IR (neat): 3415, 3290, 2975, 2920, 1685, 1500, 1455, 1365, 1250, 1160, 1140, 950, 800 cm⁻¹. ¹H NMR (300 MHz, CDCl₃): δ=1.43 (s, 9H), 3.45-3.51 (m, 1H), 3.60-3.65 (m, 1H), 4.34 (t, J=5.3 Hz, 1H), 5.02 (br s, 1H), 6.83 (dt, J=2.3 and 9.6 Hz, 1H), 6.97 (dd, J=2.3 and 9.6 Hz, 1H), 7.03 (s, 1H), 7.49 (dd, J=5.3 and 8.7 Hz, 1H), 8.74 (br s, 1H, NH indole) ppm. ¹³C NMR (75.5 MHz, CDCl₃): δ=28.4 (3C), 42.4, 58.6, 79.9, 97.6 (d, J=26.2 Hz), 108.4 (d, J=24.5 Hz), 122.8, 122.9, 128.8 (d, J=12.2 Hz), 136.0, 136.1, 158.4, 160.0 (d, J=238.5 Hz) ppm. ¹⁹F NMR (282 MHz, CDCl₃): δ=−120.7 (m, 1F) ppm. LRMS (ESI): m/z (%)=332 (43) [(M+Na)⁺], 310 (6) [(M+H)⁺], 239 (100), 221 (75).

tert-Butyl 2-(5-iodo-1H-indol-3-yl)-2-(hydroxyamino)-ethylcarbamate (Zh)

Compound (Zh) (125 mg, 0.30 mmol) was obtained from nitrone (Yh) (202 mg, 0.40 mmol) and NH₂OH.HCl (83 mg, 1.20 mmol) as beige foam. Yield: 75%.

IR (neat): 3410, 3280, 2975, 2925, 1685, 1510, 1455, 1365, 1250, 1160, 795, 750 cm⁻¹. ¹H NMR (300 MHz, CDCl₃): δ=1.44 (s, 9H), 3.40-3.49 (m, 2H), 3.50-3.61 (m, 1H), 4.26 (t, J=5.2 Hz, 1H), 5.08 (br s, 1H), 6.95 (s, 1H), 7.04 (d, J=8.5 Hz, 1H), 7.35 (dd, J=1.4 and 8.5 Hz, 1H), 7.94 (s, 1H), 8.96 (br s, 1H, NH indole) ppm. ¹³C NMR (75.5 MHz, CDCl₃): δ=28.3 (3C), 42.5, 58.5, 79.9 (C), 83.0, 112.1, 113.4, 123.5, 127.9, 128.8, 130.3, 135.1, 157.0 ppm. LRMS (ESI): m/z (%)=440 (18) [(M+Na)⁺], 418 (56) [(M+H)⁺], 376 (100).

tert-Butyl 2-(6-iodo-1H-indol-3-yl)-2-(hydroxyamino)-ethylcarbamate (Zi)

The compound (Zi) can be obtained from indolic N-hydroxylamine (Yi) according to the procedure described in this patent.

tert-Butyl 2-(4-bromo-1H-indol-3-yl)-2-(hydroxyamino)ethylcarbamate (Zj)

Compound (Zj) (75 mg, 0.202 mmol) was obtained from nitrone (Yj) (137 mg, 0.30 mmol) and NH₂OH.HCl (63 mg, 0.90 mmol) as a beige foam. Yield: 68%.

IR (neat): 3415, 3275, 2975, 2925, 1685, 1510, 1365, 1335, 1250, 1160, 775, 735 cm⁻¹. ¹H NMR (300 MHz, CDCl₃): δ=1.43 (s, 9H), 3.57-3.75 (m, 2H), 5.06-5.16 (m, 2H), 6.93 (t, J=7.8 Hz, 1H), 7.18-7.25 (m, 3H), 9.18 (br s, 1H, NH indole) ppm. ¹³C NMR (75.5 MHz, CDCl₃): δ=28.3 (3C), 42.2, 57.2, 79.8 (C), 110.9, 112.9, 113.3, 122.8, 124.2, 124.4, 124.5, 137.5, 157.4 ppm. LRMS (ESI): m/z (%)=384 (28) [(M+Na)⁺], 372 (14) [(M+H)⁺], 360 (11), 328 (100), 293 (23).

tert-Butyl 2-(7-bromo-1H-indol-3-yl)-2-(hydroxyamino)ethylcarbamate (Zk)

tert-Butyl 2-(2-bromo-1H-indol-3-yl)-2-(hydroxyamino)ethylcarbamate (Zl)

The compounds (Zk) and (Zl) can be obtained from indolic N-hydroxylamines (Yk) and (Yl) respectively according to the procedure described in this patent.

2.5 Synthesis of Indolic Amines (1a-l)

tert-Butyl 2-amino-2-(1H-indol-3-yl)ethylcarbamate (1a)

a. Synthesis from Primary Hydroxylamine (Za)

To a stirred solution of primary hydroxylamine (Za) (70 mg, 0.24 mmol) in 1 mL of methanol was added 0.51 mL of a 15% aqueous solution of titanium trichloride (74 mg, 0.48 mmol). The resulting mixture was stirred at room temperature during 30 min. A large excess of a 20% aqueous solution of sodium hydroxide saturated with sodium chloride was added. Methanol was removed under vacuum and the crude mixture was extracted three times with EtOAc. The combined organic layers were washed with water and brine, dried over anhydrous MgSO₄ and evaporated. The residue was purified by column chromatography on silica gel (Eluent: EtOAc). The product (1a) was obtained as a white solid (64 mg, 0.23 mmol). Yield: 97%.

b. Synthesis from Indolic N-Hydroxylamine (Xa)

For this procedure, see: Xavier Guinchard, thèse de l'Université Joseph Fourier, Grenoble 1, 2006.

To a stirred solution of indolic N-hydroxylamine (Xa) (2.0 g, 5.25 mmol) in 93 mL of methanol and 3.5 mL of acetic acid was added 0.8 g of Pearlman's catalyst (Pd(OH)₂). Argon was replaced by hydrogen. The resulting mixture was then stirred at room temperature during 40 h. It was then filtered through celite. The resulting filtrate was treated by a 6N aqueous solution of NaOH. Methanol was then evaporated under vacuum. The resulting aqueous phase was extracted three times with EtOAc. Combined organics layers were washed with brine and dried over anhydrous $MgSO_4$. After the removal of the solvent, the residue was purified by column chromatography on silica gel (Eluent: EtOAc). The product (Za) was obtained as a white solid (1.31 g, 4.75 mmol). Yield: 90%.

Mp: 145-146° C. IR (neat): 3404, 3339, 3308, 3053, 2977, 2930, 1703, 1693, 1682, 1537, 1531, 1519, 1514, 1504, 1455, 1393, 1367, 1337, 1251, 1170 $cm^{-1}$. $^1$H NMR (300 MHz, $CDCl_3$): δ=1.44 (s, 9H, $C(CH_3)_3$), 1.76 (br s, 2H, $NH_2$), 3.39 (ddd, J=6.5, 7.0 and 13.0 Hz, 1H, 1H of $CH_2N$), 3.57 (ddd, J=5.5, 6.5 and 13.0 Hz, 1H, 1H of $CH_2N$), 4.41 (dd, J=5.5 and 7.0 Hz, 1H, CHN), 4.90 (br s, 1H, NHBoc), 7.12 (ddd, J=1.0, 7.5 and 7.5 Hz, 1H, H indole), 7.13 (s, 1H, H indole), 7.20 (ddd, J=1.0, 7.5 and 7.5 Hz, 1H, H indole), 7.37 (d, J=8.0 Hz, 1H, H indole), 7.71 (d, J=8.0 Hz, 1H, H indole), 8.30 (br s, 1H, NH) ppm. $^{13}$C NMR (75.5 MHz, $CDCl_3$): δ=28.4 ($C(\underline{C}H_3)_3$), 47.5 ($CH_2$), 48.7 (CHN), 79.3 ($\underline{C}(CH_3)_3$), 111.3 (CH indole), 118.6 (C indole), 119.3 (CH indole), 119.6 (CH indole), 121.0 (CH indole), 122.3 (CH indole), 125.9 (C indole), 136.6 (C indole), 156.2 (C=O) ppm. LRMS (DCI, $NH_3$+isobutane): m/z=276 [(M+H)$^+$]. Anal. calcd for $C_{15}H_{21}N_3O_2$: C, 65.43; H, 7.69; N, 15.26. Found: C, 65.22; H, 7.69; N, 15.19.

tert-Butyl 2-amino-2-(5-bromo-1H-indol-3-yl)ethylcarbamate (1b)

To a stirred solution of primary hydroxylamine (Zb) (556 mg, 1.50 mmol) in 5 mL of methanol was added 3.53 mL of a 15% aqueous solution of titanium trichloride (509 mg, 3.3 mmol). The resulting mixture was stirred at room temperature during 30 min. A large excess of a 20% aqueous solution of sodium hydroxide saturated with sodium chloride was added. Methanol was removed under vacuum and the crude mixture was extracted three times with EtOAc. The combined organic layers were washed with water and brine, dried over anhydrous $MgSO_4$ and evaporated. The residue was purified by column chromatography on silica gel (Eluent: EtOAc). The product (Zb) was obtained as a white solid (438 mg, 1.24 mmol). Yield: 83%.

Mp: 151° C. IR (film): 3423, 3296, 2977, 2925, 1692, 1508, 1456, 1363, 1280, 1250, 1164 $cm^{-1}$. $^1$H NMR (300 MHz, MeOD): δ=1.41 (s, 9H, $C(CH_3)_3$), 3.20-3.50 (m, 2H, $CH_2N$), 4.28 (dd, J=5.9 and 7.3 Hz, 1H, CHN), 7.18 (dd, J=1.8 and 8.6 Hz, 1H, H indole), 7.26 (d, J=8.5 Hz, 1H, H indole), 7.26 (s, 1H, H indole), 7.81 (d, J=1.5 Hz, 1H, H indole) ppm. $^{13}$C NMR (75.5 MHz, MeOD): δ=28.7 ($C(\underline{C}H_3)_3$), 48.9 ($CH_2$), 49.4 (CHN), 80.1 ($\underline{C}(CH_3)_3$), 113.1 (C indole), 114.0 (CH indole), 117.6 (C indole), 122.3 (CH indole), 124.2 (CH indole), 125.3 (CH indole), 129.2 (C indole), 136.7 (C indole), 158.5 (C=O) ppm. LRMS (ESI): m/z=354 and 356 [(M+H)$^+$]. HRMS (ESI) Calcd for $C_{15}H_{21}N_3O_2{}^{79}Br$: 354.0817. Found: 354.0837 [(M+H)$^+$].

tert-Butyl 2-amino-2-(6-bromo-1H-indol-3-yl)ethylcarbamate (1c)

To a stirred solution of 280 mg (0.756 mmol) of primary hydroxylamine (Zc) in 3 mL of methanol was added 1.78 mL of a 15% aqueous solution of titanium trichloride (257 mg, 1.66 mmol). The resulting mixture was stirred at room temperature during 30 min. A large excess of a 20% aqueous solution of NaOH saturated with sodium chloride was added. Methanol was removed under vacuum and the crude mixture was extracted three times with EtOAc. The combined organic layers were washed with water and brine, dried over anhydrous $MgSO_4$ and evaporated. The resulting residue was purified by column chromatography on silica gel (Eluent: EtOAc) to afford the product (1c) as a white solid (248 mg, 0.70 mmol). Yield: 92%.

Mp: 80° C. IR (neat): 3287, 2977, 2931, 1692, 1505, 1458, 1364, 1171, 803 $cm^{-1}$. $^1$H NMR (300 MHz, MeOD): δ=1.42 (s, 9H, $C(CH_3)_3$), 3.20-3.30 (m, 1H, CH of $CH_2$), 3.42-3.50 (m, 1H, H of $CH_2$), 4.31 (dd, J=5.5 and 7.9 Hz, 1H, CHN), 7.13 (dd, J=1.8 and 8.5 Hz, 1H, H indole), 7.24 (s, 1H, H indole), 7.51 (d, J=1.7 Hz, 1H, H indole), 7.58 (d, J=8.2 Hz, 1H, H indole) ppm. $^{13}$C NMR (75.5 MHz, MeOD): δ=28.7 ($C(\underline{C}H_3)_3$), 48.8 ($CH_2$), 49.6 (CHN), 80.2 ($\underline{C}(CH_3)_3$), 115.2 (CH indole), 114.0 (C indole), 118.0 (C indole), 121.1 (CH indole), 123.0 (CH indole), 123.6 (CH indole), 126.4 (C indole), 139.0 (C indole), 158.5 (C=O) ppm. LRMS (ESI): m/z=354 and 356 [(M+H)$^+$]. HRMS (ESI) Calcd for $C_{15}H_{21}N_3O_2{}^{79}Br$: 354.0817. Found: 354.0812 [(M+H)$^+$].

tert-Butyl 2-amino-2-(5-chloro-1H-indol-3-yl)ethylcarbamate (1d)

To a stirred solution of indolic N-hydroxylamine (Zd) (326 mg, 1.0 mmol) in 5 mL of methanol was added 1.7 mL of a 15% aqueous solution of titanium trichloride (339 mg, 2.2 mmol). The resulting mixture was stirred at room temperature during 30 min. A large excess of a 20% aqueous solution of NaOH saturated with NaCl was added. Methanol was then removed under vacuum and the crude mixture was extracted with EtOAc (3×20 mL). Combined organic layers were washed with $H_2O$ and brine, dried over anhydrous $Na_2SO_4$, filtered and concentrated under vacuum. Pure amine (1d) was obtained as a white solid (288 mg, 0.932 mmol). Yield: 93%.

$^1$H NMR (300 MHz, $CD_3OD$): δ=1.41 (s, 9H), 3.39-3.45 (m, 2H), 4.30-4.34 (m, 1H), 7.06 (d, J=7.8 Hz, 1H), 7.28-7.33 (m, 2H), 7.66 (s, 1H) ppm. $^{13}$C NMR (75.5 MHz, $CD_3OD$): δ=28.8 (3C), 48.7, 49.3, 80.2 (C), 113.6, 117.2, 119.2, 122.8, 124.5, 125.7, 128.6, 136.5, 156.5 ppm. LRMS (ESI): m/z (%)=310 (13) [(M+H)$^+$], 237 (100) [(M-$C_4H_9O$+H)$^+$].

2.6. Synthesis of Amines (1e-l)

These compounds can be prepared according the method described in this patent.

tert-Butyl 2-amino-2-(6-chloro-1H-indol-3-yl)ethylcarbamate (1e)

tert-Butyl 2-amino-2-(5-fluoro-1H-indol-3-yl)ethylcarbamate (1f)

tert-Butyl 2-amino-2-(6-fluoro-1H-indol-3-yl)ethylcarbamate (1g)

tert-Butyl 2-amino-2-(5-iodo-1H-indol-3-yl)ethylcarbamate (1h)

tert-Butyl 2-amino-2-(6-iodo-1H-indol-3-yl)ethylcarbamate (1i)

tert-Butyl 2-amino-2-(4-bromo-1H-indol-3-yl)ethylcarbamate (1j)

tert-Butyl 2-amino-2-(7-bromo-1H-indol-3-yl)ethyl-carbamate (1k)

tert-Butyl 2-amino-2-(2-bromo-1H-indol-3-yl)ethyl-carbamate (1l)

Example 3: Preparation of Indolic Derivatives Wherein R is $CH_2NHCO_2(C_1-C_7)$-Alkyl or $CH_2NHCO_2(C_3-C_7)$-Cycloalkyl The procedure is presented in scheme II:

SCHEME II

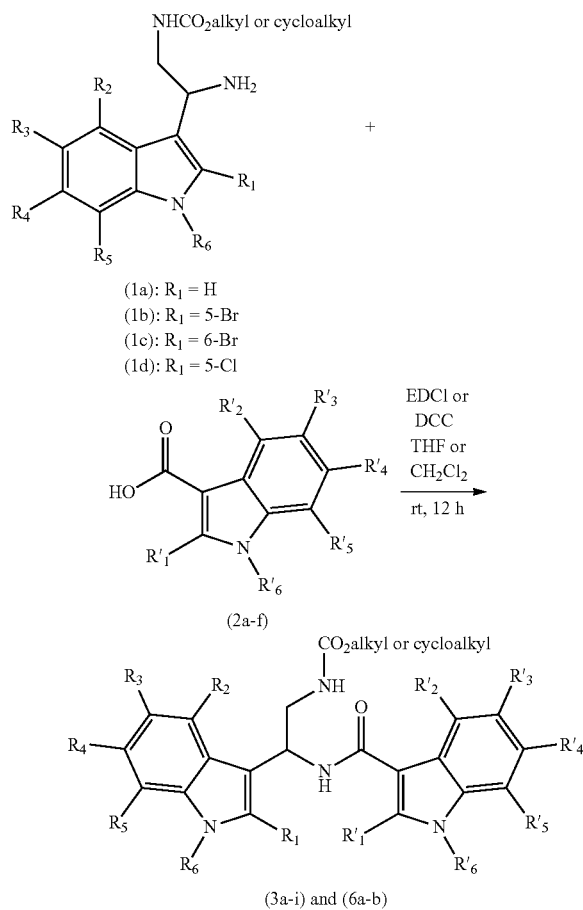

(1a): $R_1$ = H
(1b): $R_1$ = 5-Br
(1c): $R_1$ = 6-Br
(1d): $R_1$ = 5-Cl (2a-f)

(3a-i) and (6a-b)

Yields obtained for alkyl=tert-butyl (3a-i and 6a-b) are summarized in the following table I.

TABLE I

| References | $R_3$ | $R_4$ | $R'_3$ | $R'_4$ | Yields |
|---|---|---|---|---|---|
| 3a | H | H | H | H | 40% |
| 3b | 5-Br | H | H | H | 73% |
| 3c | H | H | 5'-Br | H | 72% |
| 3d | H | 6-Br | H | H | 65% |
| 3e | H | H | H | 6'-Br | 76% |
| 3f | 5-Br | H | 5'-Br | H | 68% |
| 3g | 5-Br | H | H | 6'-Br | 65% |
| 3h | H | 6-Br | 5'-Br | H | 52% |
| 3i | H | 6-Br | H | 6'-Br | 47% |
| 6a | Cl | H | Cl | H | 75% |
| 6b | Cl | H | H | Cl | 62% | tert-Butyl (2-(1H-indol-3-yl)-2-(1H-indole-3-carboxamido)ethyl)carbamate 3a

In a flask, the [2-amino-2-(1H-indol-3-yl)ethyl]carbamic acid tert-butyl ester (1a) (100 mg, 0.364 mmol) was dissolved in 5 mL of THF. To this solution, 1H-indole-3-carboxylic acid (2a) (59 mg, 0.366 mmol) and 1-ethyl-3-(3-dimethylaminopropyl) carbodiimide (EDCI, 71 µL, 0.400 mmol) were added. The reacting mixture was stirred for 20 hours at room temperature. The homogeneous crude material was then diluted in a large amount of ethyl acetate (30 mL). The organic layer was washed twice with 1N aqueous HCl and once with brine. The organic layer was dried over anhydrous $MgSO_4$ and concentrated. The crude material was purified by flash chromatography (EtOAc/pentane, 3/7) to afford the desired product 3a (60 mg, 0.143 mmol) as a white solid. Yield: 40%.

$^1$H NMR (300 MHz, $(CD_3)_2CO$): δ=1.36 (s, 9H, $C(CH_3)_3$), 3.70-3.75 (m, 2H, $CH_2$), 5.72 (m, 1H, CHN), 6.28 (s, 1H, NHBoc), 7.01 (t, J=7.5 Hz, 1H, H indole), 7.08-7.18 (m, 3H, H indole), 7.35-7.45 (m, 4H, H indole+NH), 7.79 (d, J=8.0 Hz, 1H, H indole), 7.98 (s, 1H, H indole), 8.29 (d, J=7.4 Hz, 1H, H indole), 10.13 (s, 1H, NH), 10.64 (s large, 1H, NH). $^{13}$C NMR (75.5 MHz, DMSO-$d_6$): δ=28.2 (C($\underline{C}H_3$)$_3$), 44.5 ($CH_2$), 45.2 (CHN), 77.7 ($\underline{C}(CH_3)_3$), 110.7, 111.3, 111.7, 115.1, 118.4, 118.9, 120.2, 121.0, 121.7, 122.3, 126.2, 126.4, 127.8, 136.1, 136.2, 156.0, 164.1 (C=O), 163.0 (C=O). LRMS (ESI): m/z=441 [(M+Na)$^+$].

tert-Butyl (2-(5-bromo-1H-indol-3-yl)-2-(1H-indole-3-carboxamido)ethyl)carbamate (3b)

In a flask, the [2-amino-2-(5-bromo-1H-indol-3-yl)ethyl]carbamic acid tert-butyl ester (1b) (60 mg, 0.169 mmol) was dissolved in 5 mL of $CH_2Cl_2$. To this solution, 1H-indole-3-carboxylic acid (2a) (27 mg, 0.169 mmol) and dicyclohexylcarbodiimide (DCC, 38 mg, 0.186 mmol) were added. The reacting mixture was stirred during 20 hours at room temperature. The heterogeneous mixture was evaporated under vacuum and the resulting solid was directly purified by flash chromatography (EtOAc/pentane, 1/1 then 2/8) to afford the desired product 3b (62 mg, 0.125 mmol) as a white solid. Yield: 73%.

Mp: 198° C. decomposition (EtOAc/cyclohexane). IR: 3411, 3392, 3370, 3328, 3289, 1657, 1619, 1536, 1489, 1458, 1169, 732 cm$^{-1}$. $^1$H NMR (400 MHz, MeOD): δ=1.35 (s, 9H), 3.58-3.70 (m, 2H), 5.56-5.60 (m, 1H), 7.12-7.19 (m, 3H), 7.27 (d, J=8.6 Hz, 1H), 7.32 (s, 1H), 7.40 (d, J=7.4 Hz, 1H), 7.90-7.92 (m, 2H), 8.11 (d, J=7.6 Hz, 1H) ppm. $^{13}$NMR (100 MHz, MeOD): δ=28.7, 45.7, 48.4, 80.3, 111.9, 112.7, 113.3, 114.0, 115.5, 121.9, 121.9, 122.5, 123.4, 124.8, 125.4, 127.1, 129.3, 129.4, 136.8, 138.1, 159.1, 168.2 ppm. LRMS (ESI): m/z=497 and 499 [(M+H)$^+$], 519 and 521 [(M+Na)$^+$].

tert-Butyl [2-(1H-indol-3-yl)-2-(5-bromo-1H-indol-3-yl-carboxamido)ethyl]carbamate 3c In a flask, the 2-amino-2-(1H-indol-3-yl)ethyl]carbamic acid tert-butyl ester (1a) (150 mg, 0.545 mmol) was dissolved in 8 mL of THF. To this solution, 5-bromo-1H-indole-3-carboxylic acid (2b) (131 mg, 0.545 mmol) and 1-ethyl-3-(3-dimethylaminopropyl)carbodiimide (EDCI, 110 µL, 0.599 mmol) were added. The reacting mixture was stirred during 20 hours at room temperature and then diluted in a large amount of EtOAc (30 mL). The organic layer was washed twice with 1N aqueous HCl then once with brine, dried over anhydrous $MgSO_4$ and then evaporated under vacuum. The resulting crude material was purified by flash chromatography (EtOAc/pentane, 1/1 then 3/7) to afford the desired product 3c (195 mg, 0.392 mmol) as a white solid. Yield: 72%.

Mp: 183° C. (EtOAc/pentane). $^1$H NMR (300 MHz, MeOD): δ=1.35 (s, 9H), 3.60-3.74 (m, 2H), 5.62-5.66 (m, 1H), 6.99-7.05 (m, 1H), 7.08-7.13 (m, 1H), 7.25-7.31 (m, 4H), 7.71-7.74 (m, 1H), 7.91 (s, 1H), 8.32 (s, 1H) ppm. $^{13}$C NMR (75.5 MHz, MeOD): δ=28.7 (C($\underline{C}$H$_3$)$_3$), 45.7 (CH$_2$), 48.6 (CHN), 80.3 ($\underline{C}$(CH$_3$)$_3$), 111.7, 112.4, 114.4, 115.4, 119.9, 120.1, 122.7, 123.2, 124.7, 126.3, 127.7, 129.2, 130.2, 136.7, 138.3, 159.1, 167.6 ppm. IR: 3374, 3309, 1728, 1652, 1626, 1533, 1455, 1371, 1355, 1293, 1256, 1166, 739. cm$^{-1}$. LRMS (ESI): m/z=519 and 521 [(M+Na)$^+$]. HRMS (ESI) calcd for C$_{24}$H$_{25}$N$_4$O$_3$BrNa: 519.1002 and 521.0985. Found: 519.1004 and 521.0982 [(M+Na)$^+$].

tert-Butyl (2-(6-bromo-1H-indol-3-yl)-2-(1H-indolyl-3-carboxamido)ethyl)carbamate 3d In a flask, the [2-amino-2-(6-bromo-1H-indol-3-yl)ethyl] carbamic acid tert-butyl ester (1c) (60 mg, 0.169 mmol) was dissolved in 4 mL of THF. To this solution, 1H-indole-3-carboxylic acid (2a) (28 mg, 0.169 mmol) and 1-ethyl-3-(3-dimethylaminopropyl)carbodiimide (EDCI, 33 μL, 0.186 mmol) were added. The reacting mixture was stirred during 20 hours at room temperature and then diluted in a large amount of EtOAc (30 mL). The organic layer was washed twice with 1N aqueous HCl, once with brine, dried over anhydrous MgSO$_4$ and then evaporated under vacuum. The resulting crude material was purified by flash chromatography (EtOAc/pentane, 1/1 then 2/8) to afford the desired product 3d (55 mg, 0.111 mmol) as a white solid. Yield: 65%.

Mp: 207° C. decomp. (EtOAc/cyclohexane). $^1$H NMR (300 MHz, MeOD): δ=1.34 (s, 9H), 3.63-3.67 (m, 2H), 5.59-5.64 (m, 1H), 7.10-7.19 (m, 3H), 7.29 (s, 1H), 7.39-7.42 (m, 1H), 7.51 (d, J=1.5 Hz, 1H), 7.65 (d, J=8.5 Hz, 1H), 7.89 (s, 1H), 8.08-8.11 (m, 1H) ppm. $^{13}$C NMR (75.5 MHz, MeOD): δ=28.7 (C($\underline{C}$H$_3$)$_3$), 45.6 (CH$_2$), 48.4 (CHN), 80.3 ($\underline{C}$(CH$_3$)$_3$), 111.9, 112.8, 115.3, 116.0, 116.1, 121.4, 121.8, 122.0, 123.1, 123.4, 124.1, 126.6, 127.1, 129.3, 138.1, 139.0, 159.1, 168.2 ppm. IR: 3400, 3367, 3309, 2983, 2936, 1655, 1625, 1536, 1496, 1365, 1289, 1163, 807, 734 cm$^{-1}$. LRMS (ESI): m/z=497 and 499 [(M+H)$^+$], 519 and 521 [(M+Na)$^+$]. HRMS (ESI) calcd for C$_{24}$H$_{25}$N$_4$O$_3$BrNa: 519.1002 and 521.0985. Found: 519.1005 and 521.0983 [(M+Na)$^+$].

tert-Butyl (2-(1H-indol-3-yl)-2-(6-bromo-1H-indolyl-3-carboxamido)ethyl)carbamate 3e In a flask, the [2-amino-2-(1H-indol-3-yl)ethyl]carbamic acid tert-butyl ester (1a) (60 mg, 0.218 mmol) was dissolved in 4 mL of THF. To this solution, 6-bromo-1H-indole-3-carboxylic acid (2c) (53 mg, 0.218 mmol) and 1-ethyl-3-(3-dimethylaminopropyl)carbodiimide (EDCI, 45 μL, 0.248 mmol) were added. The reacting mixture was stirred during 20 hours at room temperature and then diluted in a large amount of EtOAc (30 mL). The organic layer was washed twice with 1N aqueous HCl, once with brine, dried over anhydrous MgSO$_4$ and then evaporated under vacuum. The resulting crude material was purified by flash chromatography (EtOAc/pentane, 1/1 then 3/7) to afford the desired product 3e (83 mg, 0.167 mmol) as a white solid. Yield: 77%.

Mp: 215° C. (EtOAc/pentane). $^1$H NMR (300 MHz, MeOD): δ=1.35 (s, 9H), 3.63-3.72 (m, 2H), 5.62-5.65 (m, 1H), 7.01 (t, J=7.4 Hz, 1H), 7.10 (t, J=7.4 Hz, 1H), 7.24 (d, J=8.6 Hz, 1H), 7.28 (s, 1H), 7.35 (d, J=8 Hz, 1H), 7.58 (br s, 1H), 7.72 (d, J=7.9 Hz, 1H), 7.89 (s, 1H), 8.03 (d, J=8.6 Hz, 1H) ppm. $^{13}$C NMR (75.5 MHz, MeOD): δ=28.7 (C($\underline{C}$H$_3$)$_3$), 45.7 (CH$_2$), 48.6 (CHN), 80.2 ($\underline{C}$(CH$_3$)$_3$), 112.2 (C), 112.4 (CH), 112.5 (C), 115.3 (C), 115.6 (CH), 116.8 (C), 119.9 (CH), 120.0 (CH), 122.7 (CH), 123.1 (CH), 123.4 (CH), 125.0 (CH), 126.3 (C), 126.3 (C), 127.6 (C), 129.8 (CH), 138.3 (C), 138.9 (C), 159.1 (C), 167.6 (C) ppm. IR: 3410, 3392, 3370, 3324, 3292, 2977, 1655, 1626, 1535, 1496, 1160, 737 cm$^{-1}$. LRMS (ESI): m/z=519 and 521 [(M+Na)$^+$]. HRMS (ESI) calcd for C$_{24}$H$_{25}$N$_4$O$_3$BrNa: 519.1002 and 521.0985. Found: 519.1004 and 521.0982 [(M+Na)$^+$].

tert-Butyl(2-(5-bromo-1H-indol-3-yl)-2-(5-bromo-1H-indolyl-3-carboxamido)ethyl)carbamate 3f In a flask, the [2-amino-2-(5-bromo-1H-indol-3-yl)ethyl] carbamic acid tert-butyl ester (1b) (60 mg, 0.169 mmol) was dissolved in 5 mL of THF. To this solution, 5-bromo-1H-indole-3-carboxylic acid (2b) (41 mg, 0.169 mmol) and 1-ethyl-3-(3-dimethylaminopropyl)carbodiimide (EDCI, 33 μL, 0.186 mmol) were added. The reacting mixture was stirred for 20 hours at room temperature. The homogeneous crude material was then diluted in a large amount of ethyl acetate (30 mL). The organic layer was washed twice with 1N aqueous HCl and once with brine. The organic layer was dried over anhydrous MgSO$_4$ and concentrated. The crude material was purified by flash chromatography (EtOAc/pentane, 1/1 then 3/7) to afford the desired product 3f (67 mg, 0.116 mmol) as a white solid. Yield: 68%.

Mp: 225° C. (EtOAc/pentane). $^1$H NMR (300 MHz, MeOD): δ=1.35 (s, 9H), 3.56-3.71 (m, 2H), 5.55-5.59 (m, 1H), 7.18 (dd, J=1.8 and 8.6 Hz, 1H), 7.25-7.34 (m, 4H), 7.89-7.92 (m, 2H), 8.31 (br s, 1H) ppm. $^{13}$C NMR (75.5 MHz, MeOD): δ=28.7 (C($\underline{C}$H$_3$)$_3$), 45.6 (CH$_2$), 48.3 (CHN), 80.3 ($\underline{C}$(CH$_3$)$_3$), 111.6, 113.3, 114.0, 114.3, 115.3, 122.5, 124.6, 124.7, 125.4, 126.3, 129.1, 129.4, 130.1, 136.7, 138.8, 159.0, 167.5 ppm. IR (ATR): 3429, 3376, 3296, 2985, 1729, 1647, 1625, 1525, 1457, 1361, 1254, 1164, 887, 790 cm$^{-1}$. LRMS (ESI): m/z=597, 599 and 601 [(M+Na)$^+$]. HRMS (ESI) calcd for C$_{24}$H$_{24}$N$_4$O$_3$Br$_2$Na: 597.0107, 599.0089 and 601.0073. Found: 597.0114, 599.0091 and 601.0071 [(M+Na)$^+$].

tert-Butyl(2-(5-bromo-1H-indol-3-yl)-2-(6-bromo-1H-indolyl-3-carboxamido)ethyl)carbamate 3g In a flask, the [2-amino-2-(5-bromo-1H-indol-3-yl)ethyl] carbamic acid tert-butyl ester (1b) (80 mg, 0.226 mmol) was dissolved in 5 mL of THF. To this solution, 6-bromo-1H-indole-3-carboxylic acid (2c) (54 mg, 0.226 mmol) and 1-ethyl-3-(3-dimethylaminopropyl)carbodiimide (EDCI, 45 μL, 0.248 mmol) were added. The reacting mixture was stirred for 20 hours at room temperature. The homogeneous crude material was then diluted in a large amount of ethyl acetate (30 mL). The organic layer was washed twice with 1N aqueous HCl and once with brine, dried over anhydrous MgSO$_4$ and concentrated. The crude material was purified by flash chromatography (EtOAc/pentane, 1/1 then 2/8) to afford the desired product 3g (84 mg, 0.146 mmol) as a white solid. Yield: 65%.

Mp: 203° C. (EtOAc/cyclohexane). IR (ATR): 3359, 3293, 2977, 1663, 1626, 1533, 1448, 1277, 1167 cm$^{-1}$. $^1$H NMR (300 MHz, MeOD): δ=1.35 (s, 9H), 3.58-3.69 (m, 2H), 5.55-5.58 (m, 1H), 7.18-7.27 (m, 3H), 7.29 (s, 1H), 7.58 (m, 1H), 7.90 (s, 2H), 8.03 (d, J=8.5 Hz, 1H) ppm. $^{13}$C NMR (75.5 MHz, MeOD): δ=28.7 (C($\underline{C}H_3$)$_3$), 45.6 (CH$_2$), 48.3 (CHN), 80.3 ($\underline{C}$(CH$_3$)$_3$), 112.2, 113.3, 114.0, 115.4, 115.6, 116.8, 122.5, 123.4, 124.7, 125.1, 125.4, 126.5, 129.4, 129.8, 136.8, 138.8, 159.1, 167.6 ppm. LRMS (ESI): m/z=597, 599 and 601 [(M+Na)$^+$]. HRMS (ESI) calcd for C$_{24}$H$_{24}$N$_4$O$_3$Br$_2$Na: 597.0107, 599.0089 and 601.0073. Found: 597.0113, 599.0090 and 601.0071 [(M+Na)$^+$].

tert-Butyl (2-(6-bromo-1H-indol-3-yl)-2-(5-bromo-1H-indolyl-3-carboxamido)ethyl)carbamate 3h In a flask, the [2-amino-2-(6-bromo-1H-indol-3-yl)ethyl] carbamic acid tert-butyl ester (1c) (40 mg, 0.113 mmol) was dissolved in 3 mL of THF. To this solution, 5-bromo-1H-indole-3-carboxylic acid (2b) (27 mg, 0.113 mmol) and 1-ethyl-3-(3-dimethylaminopropyl)carbodiimide (EDCI, 22 µL, 0.124 mmol) were added. The reacting mixture was stirred for 20 hours at room temperature. The homogeneous crude material was then diluted in a large amount of ethyl acetate (30 mL). The organic layer was washed twice with 1N aqueous HCl and once with brine, dried over anhydrous MgSO$_4$ and concentrated. The crude material was purified by flash chromatography (EtOAc/pentane, 1/1 then 3/7) to afford the desired product 3h (34 mg, 0.059 mmol) as a white solid. Yield: 52%.

Mp: 227° C. (EtOAc/pentane). $^1$H NMR (300 MHz, MeOD): δ=1.35 (s, 9H), 3.61-3.71 (m, 2H), 5.59-5.65 (m, 1H), 7.12 (dd, J=1.7 and 8.5 Hz, 1H), 7.24-7.34 (m, 3H), 7.51 (d, J=1.5 Hz, 1H), 7.64 (d, J=8.5 Hz, 1H), 7.92 (s, 1H), 8.32 (br s, 1H) ppm. $^{13}$C NMR (75.5 MHz, MeOD): δ=28.7 (C($\underline{C}H_3$)$_3$), 45.6 (CH$_2$), 48.2 (CHN), 80.3 ($\underline{C}$(CH$_3$)$_3$), 111.6, 114.3, 115.3, 115.3, 115.8, 116.1, 121.4, 123.2, 124.1, 124.6, 126.3, 126.6, 129.1, 130.1, 136.7, 139.0, 159.1, 167.5 ppm. IR (ATR): 3364, 3293, 2978, 2933, 1652, 1628, 1530, 1455, 1290, 1253, 1162, 800, 788 cm$^{-1}$. LRMS (ESI): m/z=597, 599 and 601 [(M+Na)$^+$]. HRMS (ESI) calcd for C$_{24}$H$_{24}$N$_4$O$_3$Br$_2$Na: 597.0107, 599.0089 and 601.0073. Found: 597.0113, 599.0091 and 601.0071 [(M+Na)$^+$].

tert-Butyl (2-(6-bromo-1H-indol-3-yl)-2-(6-bromo-1H-indolyl-3-carboxamido)ethyl)carbamate 3i In a flask, the [2-amino-2-(6-bromo-1H-indol-3-yl)ethyl] carbamic acid tert-butyl ester (1c) (70 mg, 0.198 mmol) was dissolved in 4 mL of THF. To this solution, 6-bromo-1H-indole-3-carboxylic acid (2c) (47 mg, 0.198 mmol) and 1-ethyl-3-(3-dimethylaminopropyl)carbodiimide (EDCI, 38 µL, 0.217 mmol) were added. The reacting mixture was stirred for 20 hours at room temperature. The homogeneous crude material was then diluted in a large amount of ethyl acetate (30 mL). The organic layer was washed twice with 1N aqueous HCl and once with brine, dried over anhydrous MgSO$_4$ and concentrated. The crude material was purified by flash chromatography (EtOAc/pentane: 1/1 then 3/7) to afford the desired product 3i (54 mg, 0.094 mmol) as a white solid. Yield: 47%.

Mp: 231° C. (EtOAc/pentane). IR (ATR): 3436, 3365, 3303, 2982, 2939, 1727, 1650, 1626, 1531, 1451, 1360, 1255, 1161, 840, 802 cm$^{-1}$. $^1$H NMR (300 MHz, MeOD): δ=1.35 (s, 9H), 3.60-3.71 (m, 2H), 5.58-5.63 (m, 1H), 7.12 (dd, J=1.5 and 8.5 Hz, 1H), 7.24 (dd, J=1.5 and 8.6 Hz, 1H), 7.29 (s, 1H), 7.51 (d, J=1.5 Hz, 1H), 7.57 (d, J=1.7 Hz, 1H), 7.63 (d, J=8.5 Hz, 1H), 7.89 (s, 1H), 8.03 (d, J=8.6 Hz, 1H) ppm. $^{13}$C NMR (75.5 MHz, MeOD): δ=28.7 (C($\underline{C}H_3$)$_3$), 45.6 (CH$_2$), 48.4 (CHN), 80.3 ($\underline{C}$(CH$_3$)$_3$), 112.2, 115.3, 115.7, 115.9, 116.1, 116.9, 121.4, 123.2, 123.5, 124.1, 125.1, 126.3, 126.7, 129.8, 138.9, 139.1, 159.1, 167.6 ppm. LRMS (ESI): m/z=597, 599 and 601 [(M+Na)$^+$]. HRMS (ESI) calcd for C$_{24}$H$_{24}$N$_4$O$_3$Br$_2$Na: 597.0107, 599.0089 and 601.0073. Found: 597.0113, 599.0091 and 601.0071 [(M+Na)$^+$].

tert-Butyl 2-(5-chloro-1H-indol-3-yl)-2-(5-chloro-1H-indole-3-carboxamido)ethylcarbamate 6a To a stirred solution of indolic amine (1d) (93 mg, 0.3 mmol) and 5-chloro-1H-indole-3-carboxylic acid (2d) (65 mg, 0.33 mmol) in 5 mL of dry CH$_2$Cl$_2$, 1-ethyl-3-(3-dimethylaminopropyl)carbodiimide (EDCI, 5 mg, 0.33 mmol) was added at room temperature. The resulting mixture was stirred overnight. CH$_2$Cl$_2$ was evaporated then EtOAc (20 mL) and a 1M aqueous solution of hydrochloric acid (20 mL) were added. After extraction, organic phase was washed with hydrochloric acid aqueous solution, 5% Na$_2$CO$_3$ aqueous solution, brine, dried over anhydrous MgSO$_4$, filtered and concentrated under vacuum. Purification of the crude product by column chromatography using EtOAc-pentane (from 10/90 to 80/20) yielded the pure bis-indole 6a (110 mg, 0.226 mmol) as a beige foam. Yield: 75%.

IR (neat): 3410, 3290, 2975, 2930, 1685, 1625, 1535, 1450, 1365, 1160, 895, 795 cm$^{-1}$. $^1$H NMR (300 MHz, CDCl$_3$): δ=1.36 (s, 9H), 3.56-3.60 (m, 2H), 5.22-5.28 (m, 1H), 5.38-5.43 (m, 1H), 6.88-7.20 (m, 6H), 7.46-7.52 (m, 2H), 8.13 (s, 1H), 8.99 (s, 1H), 9.58 (s, 1H) ppm. $^{13}$C NMR (75.5 MHz, CDCl$_3$): δ=28.0 (3C), 44.6, 47.9, 79.8, 110.4, 112.4, 112.6, 113.7, 118.1, 120.1, 122.1, 122.8, 123.5, 124.9, 126.4, 126.7, 126.9, 128.8, 134.7, 134.8, 157.7, 165.8 ppm. LRMS (ESI): m/z (%)=509 (39) [(M+Na)$^+$], 237 (100).

tert-Butyl 2-(5-chloro-1H-indol-3-yl)-2-(6-chloro-1H-indole-3-carboxamido)ethyl carbamate 6b To a stirred solution of indolic amine (1d) (93 mg, 0.3 mmol) and 6-chloro-1H-indole-3-carboxylic acid (2e) (65 mg, 0.33 mmol) in 5 mL of dry CH$_2$Cl$_2$, 1-ethyl-3-(3-dimethylaminopropyl) carbodiimide (EDCI, 5 mg, 0.33 mmol) was added at room temperature. The resulting mixture was stirred overnight. CH$_2$Cl$_2$ was evaporated then EtOAc (20 mL) and a 1M aqueous solution of hydrochloric acid (20 mL) were added. After extraction, the organic phase was washed with a 1M aqueous hydrochloric acid, a 5% aqueous solution of Na$_2$CO$_3$, brine, dried over anhydrous MgSO$_4$, filtered and concentrated under vacuum. Purification of the resulting crude product by column chromatography using EtOAc-pentane (from 10/90 to 80/20) yielded pure bis-indole 6b (90 mg, 0.185 mmol) as a beige foam. Yield: 62%.

IR (neat): 3410, 3270, 2970, 2930, 1685, 1620, 1530, 1445, 1365, 1160, 850, 795 cm$^{-1}$. $^1$H NMR (300 MHz, CDCl$_3$): δ=1.36 (s, 9H), 3.57-3.63 (m, 2H), 5.22-5.28 (m, 1H), 5.40-5.45 (m, 1H), 6.89-7.19 (m, 6H), 7.42-7.54 (m, 2H), 7.96-8.01 (s, 1H), 9.01 (s, 1H), 9.61 (s, 1H) ppm. $^{13}$C NMR (75.5 MHz, CDCl$_3$): δ=27.7 (3C), 44.1, 47.3, 79.4 (C), 110.5, 111.3, 112.2, 113.4, 117.9, 121.2, 121.3, 121.7, 123.3, 123.8, 124.6, 126.7, 128.0, 128.3, 134.8, 136.7, 157.5, 165.8 ppm. LRMS (ESI): m/z (%)=509 (32) [(M+Na)$^+$], 237 (100).

Example 4: Preparation of Indolic Derivatives Wherein R is (C$_1$-C$_7$)-Alkyl or (C$_3$-C$_7$)-Cycloalkyl The following procedure given for R=Me, R$_3$ and R'$_3$=Br, all the other substituents being H, is representative of these compounds (SCHEME III).

SCHEME III

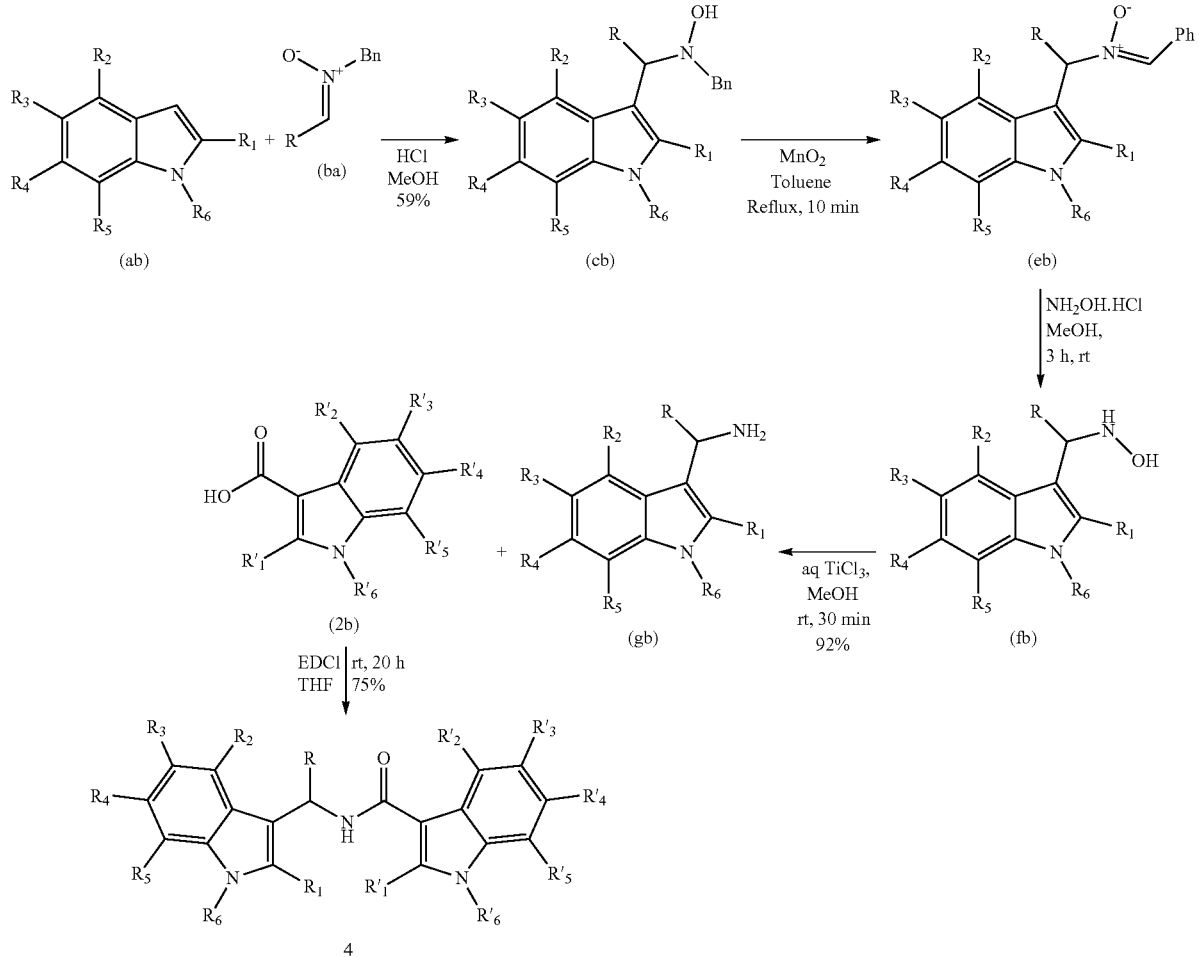

4: R = Me, R₃ and R'₃ = Br, R₁, R₂, R₄-R₆ and R'₁, R'₂, R'₄-R'₆ = H
5: R = Me, R₃ = Br and R'₃ = F, R₁, R₂, R₄-R₆ and R'₁, R'₂, R'₄-R'₆ = H

4.1 Synthesis of Compound 4

4.1.1 Synthesis of Compound (gb)

(Z)—N-Ethylidene-1-phenylmethanamine N-oxide (ba)

The synthesis of this compound was described in literature. See: J.-N. Denis, H. Mauger, Y. Vallée, *Tetrahedron Lett.* 1997, 38, 8515-8518; H. Chalaye-Mauger, J.-N. Denis, M.-T. Averbuch-Pouchot, Y. Vallée, *Tetrahedron* 2000, 56, 791-804. It was prepared according to the procedure described in these publications.

In a dry flask, freshly distilled acetaldehyde (1.39 g, 31.5 mmol) was dissolved in dry dichloromethane (50 mL). To this solution, N-hydroxybenzylamine (3.70 g, 30 mmol) and anhydrous MgSO₄ (15 g) were added. The mixture was stirred for 1 hour at room temperature under argon. The solution was then filtered through a short pad of celite to remove MgSO₄ and concentrated under vacuum. The desired product (ba) was obtained without any further purification as a white solid. Yield: 100%.

¹H NMR (300 MHz, DMSO-d₆): δ=1.82 (d, J=5.7 Hz, 3H, CH₃), 4.87 (s, 2H, CH₂), 7.21 (q, J=5.7 Hz, 1H, CH), 7.29-7.43 (m, 5H, CH) ppm. ¹³C NMR (75.5 MHz, DMSO-d₆): δ=12.2 (CH₃), 67.7 (CH₂), 127.8 (CH), 128.2 (CH), 128.8 (CH), 133.0 (CH), 134.5 (C) ppm. LRMS (ESI): m/z=150 [(M+H)⁺].

N-Benzyl-N-(1-(5-bromo-1H-indol-3-yl)ethyl)hydroxylamine (cb)

The synthesis of this compound was described in literature. See: J.-N. Denis, H. Mauger, Y. Vallée, *Tetrahedron Lett.* 1997, 38, 8515-8518; H. Chalaye-Mauger, J.-N. Denis, M.-T. Averbuch-Pouchot, Y. Vallée, *Tetrahedron* 2000, 56, 791-804. It was prepared according to the procedure described in these references.

In a dry flask cooled at 0° C. under argon, freshly distilled acetyl chloride (2.85 mL, 40 mmol) was slowly added to dry methanol (40 mL). This solution was stirred for 10 minutes at 0° C. in order to obtain a HCl solution in methanol. In another dry flask, 5-bromoindole (ab) (3.92 g, 20 mmol) and nitrone (ba) (3.07 g, 20.6 mmol) were dissolved in dry methanol (50 mL) and this solution was slowly (over 5 minutes) added to the previous one. Temperature was maintained around 0° C. The reaction was stirred for 2 h30 at 0°

C. and for 45 minutes at room temperature before quenching with a saturated aqueous solution of NaHCO$_3$. Methanol was then removed by evaporation under reduced pressure. The crude material was extracted three times with dichloromethane, washed with saturated NaHCO$_3$ and brine, dried over anhydrous MgSO$_4$ and concentrated. After purification by flash chromatography (AcOEt/pentane, 2/8 then 1/1), the desired product (cb) was obtained as a white solid. Yield: 59%.

$^1$H NMR (300 MHz, DMSO-d$_6$): δ=1.49 (d, J=6.6 Hz, 3H, CH$_3$), 3.47-3.64 (m, 2H, CH$_2$), 4.11-4.16 (m, 1H, CH), 7.15-7.33 (m, 8H, CH), 7.67 (s, 1H, OH), 7.95 (s, 1H, CH), 11.11 (br s, 1H, NH) ppm. $^{13}$C NMR (75.5 MHz, DMSO-d$_6$): δ=18.0 (CH$_3$), 59.1 (CH), 59.6 (CH$_2$), 110.8 (C), 113.2 (CH), 122.4 (CH), 123.2 (CH), 124.7 (CH), 126.2 (CH), 127.6 (CH), 128.3 (C), 128.7 (CH), 135.0 (C), 139.7 (C) ppm. LMRS (ESI): m/z=343 and 345 [(M−H)$^-$].

(Z)—N-benzylidene-1-(5-bromo-1H-indol-3-yl)ethanamine N-oxide (eb)

The synthesis of this compound is described in the following publication: O. N. Burchak, E. Le Pihive, L. Maigre, X. Guinchard, P. Bouhours, C. Jolivalt, D. Schneider, M. Maurin, C. Giglione, T. Meinnel, J.-M. Paris, J.-N. Denis, <<Synthesis and evaluation of 1-(1H-indol-3-yl)ethanamine derivatives as new antibacterial agents>>, Bioorg. Med. Chem. 2011, 19, 3204-3215. It was prepared according to the general procedure used for the synthesis of indolic nitrones (Y). Compound (cb) (3.54 g, 10.27 mmol) was dissolved in warm toluene (90 mL). After complete dissolution, MnO$_2$ (4.47 g, 51.37 mmol) was added. The solution was refluxed for 10 minutes and filtered through a short pad of celite. The celite was carefully washed with ethyl acetate. Then, the clear brown solution was concentrated to afford thick brown oil. This crude material was purified by flash chromatography with silica pre-treated with 2.5% of triethylamine (neat Et$_2$O then Et$_2$O with 1% and 2% of methanol) and the desired product (eb) was obtained as a yellowish solid. Yield: 47%.

$^1$H NMR (400 MHz, DMSO-d$_6$): δ=1.80 (d, J=6.8 Hz, 3H, CH$_3$), 5.66 (q, J=6.8 Hz, 1H, CH), 7.19 (dd, J=2.0 and 8.8 Hz, 1H, CH), 7.34-7.42 (m, 4H), 7.59 (d, J=2.4 Hz, 1H, CH), 7.95 (d, J=2.0 Hz, 1H, CH), 8.15 (s, 1H, CH), 8.22 (dd, J=2.4 and 8.0 Hz, J=2.4 Hz, 2H, CH), 11.39 (br s, 1H, NH) ppm. $^{13}$C NMR (100 MHz, DMSO-d$_6$): δ=19.8 (CH$_3$), 68.1 (CH), 112.6 (C), 113.8 (C), 114.6 (CH), 115.1 (CH), 122.2 (CH), 124.3 (CH), 124.7 (CH), 127.4 (CH), 128.7 (C), 128.8 (CH), 129.2 (CH), 130.5 (CH), 131.9 (CH), 132.1 (C), 135.8 (C) ppm. LRMS (ESI): m/z=341 and 343 [(M−H)$^-$].

N-(1-(5-Bromo-1H-indol-3-yl)ethyl)hydroxylamine (fb)

The synthesis of this compound is described in the following publication: O. N. Burchak, E. Le Pihive, L. Maigre, X. Guinchard, P. Bouhours, C. Jolivalt, D. Schneider, M. Maurin, C. Giglione, T. Meinnel, J.-M. Paris, J.-N. Denis, <<Synthesis and evaluation of 1-(1H-indol-3-yl)ethanamine derivatives as new antibacterial agents>>, Bioorg. Med. Chem. 2011, 19, 3204-3215. It was prepared according to the general procedure used for the synthesis of indolic N-hydroxylamines (Z).

Under argon, compound (eb) (1.57 g, 4.57 mmol) was stirred for 3 hours at room temperature with hydroxylamine hydrochloride (1.59 g, 22.88 mmol) in methanol (15 mL). The solution was then concentrated, dissolved in ethyl acetate, washed with a saturated aqueous solution of NaHCO$_3$ and brine. After drying over anhydrous MgSO$_4$, the organic layer was evaporated. The residue was purified by flash chromatography (from AcOEt/pentane, 1/1 to neat EtOAc) to afford the desired product (fb) as a white solid. Yield: 70%.

IR (neat): 3405, 3120, 2805, 1455, 1435, 1375, 1330, 1245, 1225, 1085, 885, 865, 795 cm$^{-1}$. $^1$H NMR (400 MHz, DMSO-d$_6$): δ=1.38 (d, J=6.4 Hz, 3H, CH$_3$), 4.20 (q, J=6.4 Hz, 1H, CH), 5.51 (br s, 1H, OH), 7.15 (dd, J=2.0 and 8.4 Hz, 1H, CH), 7.18 (s, 1H, NH), 7.26 (s, 1H, CH), 7.30 (d, J=8.4 Hz, 1H, CH), 7.82 (d, J=2.0 Hz, 1H, CH), 11.05 (br s, 1H, NH) ppm. $^{13}$C NMR (100 MHz, DMSO-d$_6$): δ=19.2 (CH$_3$), 53.7 (CH), 110.7 (C), 113.2 (CH), 116.6 (C), 121.6 (CH), 123.1 (CH), 124.1 (CH), 128.2 (C), 134.9 (C) ppm. LRMS (ESI): m/z=253 and 255 [(M−H)$^-$].

1-(5-Bromo-1H-indol-3-yl)ethanamine (gb)

In a flask, the hydroxylamine (fb) (780 mg, 3.06 mmol) was dissolved in methanol (10 mL). A 20% wt. aqueous solution of TiCl$_3$ (4.3 mL, 6.73 mmol) was added dropwise at room temperature. When the dark TiCl$_3$ solution was added, the mixture became black but lost rapidly this dark color to become clear (due to the rapid reaction between TiCl$_3$ and the hydroxylamine). After stirring for 30 minutes, the mixture was poured in a 20% wt. aqueous solution of NaOH saturated with NaCl. The resulting solution was extracted three times with ethyl acetate. The combined organic layers were washed with water and brine, dried over anhydrous MgSO$_4$ and concentrated. The desired product (gb) was obtained without any further purification as a brown solid. Yield: 92%.

$^1$H NMR (400 MHz, DMSO-d$_6$): δ=1.38 (d, J=6.8 Hz, 3H, CH$_3$), 2.16 (br s, 2H, NH$_2$), 4.25 (q, J=6.8 Hz, 1H, CH), 7.15 (dd, J=1.6 and 8.6 Hz, 1H, CH), 7.23 (s, 1H, CH), 7.30 (d, J=8.6 Hz, 1H, CH), 7.84 (s, 1H, CH), 11.00 (br s, 1H, NH) ppm. $^{13}$C NMR (100 MHz, DMSO-d$_6$): δ=25.0 (CH$_3$), 43.4 (CH), 110.6 (C), 113.2 (CH), 119.2 (C), 121.4 (CH), 122.6 (CH), 123.1 (CH), 127.5 (C), 135.1 (C) ppm. LRMS (ESI): m/z=237 and 239 [(M−H)$^-$].

4.1.2 Alternative Synthesis of Indolic Amine (gb)

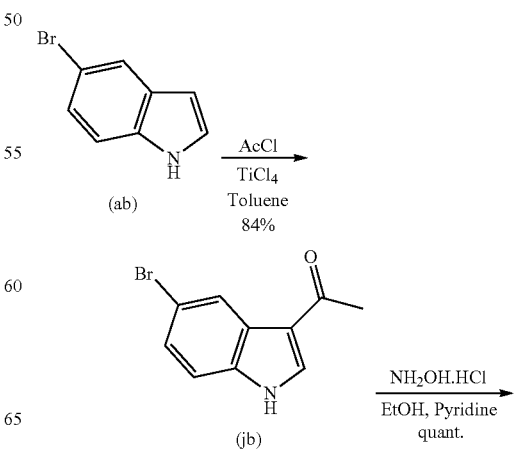

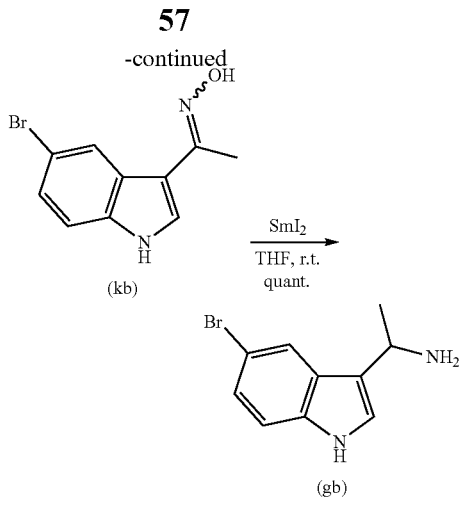

1-(5-bromo-1H-indol-3-yl)ethanone (jb)

A 1M solution of SnCl$_4$ (10 mL, 10.0 mmol) was added to a stirred solution of 5-bromoindole (ab) (980 mg, 5.0 mmol) and acetyl chloride (0.714 mL, 785 mg, 10.0 mmol) in 20 mL of dry toluene at 0° C. The resulting mixture was stirred at room temperature during 4 hours, and then 50 mL of water was added. The mixture was extracted with EtOAc (3×20 mL) and the collected organic layers were washed with water, brine, dried over anhydrous MgSO$_4$, filtered and concentrated under vacuum. Column chromatography using EtOAc-pentane (from 5/95 to 80/20) yielded pure acetylindole (jb) (1.0 g, 4.2 mmol) as a white solid. Yield: 84%.

$^1$H NMR (300 MHz, DMSO-d$_6$): δ=2.44 (s, 3H), 7.33 (dd, J=2.0 and 8.6 Hz, 1H), 7.45 (dd, J=0.4 and 8.6 Hz, 1H), 8.31 (dd, J=0.4 and 2.0 Hz, 1H), 8.34 (s, 1H) ppm. $^{13}$C NMR (75.5 MHz, DMSO-d$_6$): δ=27.1, 114.2, 114.5, 116.2, 123.4, 125.3, 127.0, 135.4, 135.5, 192.8 ppm.

1-(5-bromo-1H-indol-3-yl)ethanone oxime (kb)

NH$_2$OH.HCl (834 mg, 12.0 mmol) was added to a stirred solution of 3-acetyl-5-bromoindole (jb) (952 mg, 4.0 mmol) and pyridine (0.967 mL, 948 mg, 12.0 mmol) in 20 mL of ethanol. The resulting mixture was stirred at reflux for 2 hours and then ethanol was evaporated. Water (50 mL) was added and then the mixture was extracted with EtOAc (3×30 mL). The collected organic layers were washed with water, brine, dried over anhydrous MgSO$_4$, filtered and concentrated under vacuum. Pure oxime (kb) (1.0 g, 3.95 mmol) was obtained as a colourless oil. Yield: 99%.

$^1$H NMR (300 MHz, CD$_3$OD): δ=2.22 (s, 3H), 7.18-7.28 (m, 2H), 7.45 (s, 1H), 8.37 (s, 1H) ppm.

1-(5-bromo-1H-indol-3-yl)ethanamine (gb)

To a stirred and carefully deoxygenated solution of indolic oxime (kb) (633 mg, 2.5 mmol) and H$_2$O (720 mg, 40.0 mmol, 16 equiv.) in 10 mL of THF, a 0.1 M solution of SmI$_2$ (110 mL, 11.0 mmol, 4.4 equiv.) was added at room temperature under argon. After 10 minutes, a saturated solution of Na$_2$S$_2$O$_3$ (20 mL) and NaHCO$_3$ (20 mL) then EtOAc (50 mL) were added. After extraction, the organic phase was washed with brine, dried over anhydrous Na$_2$SO$_4$, filtered, and concentrated. Pure amine (gb) (560 mg, 2.34 mmol) was obtained as a white solid. Yield: 94%.

$^1$H NMR (300 MHz, CDCl$_3$): δ=1.38 (d, J=6.6 Hz, 3H), 2.50 (br s, 2H), 4.26 (q, J=6.6 Hz, 1H), 6.88 (s, 1H), 6.9-7.02 (m, 1H), 7.09-7.12 (m, 1H), 7.66 (s, 1H), 9.00 (br s, 1H) ppm. $^{13}$C NMR (75.5 MHz, CDCl$_3$): δ=24.3, 43.6, 112.3, 112.8, 121.2, 121.4, 121.5, 124.6, 127.5, 135.1 ppm.

4.1.3: Synthesis of Compound 4

5-Bromo-N-(1-(5-bromo-1H-indol-3-yl)ethyl)-1H-indole-3-carboxamide 4

In a flask, the indolic amine (gb) (150 mg, 0.627 mmol) was dissolved in 10 mL of THF. To this solution, 5-bromo-1H-indole-3-carboxylic acid (2b) (150 mg, 0.627 mmol) and 1-ethyl-3-(3-dimethylaminopropyl)carbodiimide (EDCI, 107 mg, 0.690 mmol) were added. The reacting mixture was stirred for 20 hours at room temperature. The crude material was then diluted in a large amount of ethyl acetate. The organic layer was washed twice with a 1N aqueous solution of HCl and once with brine. The organic layer was dried over anhydrous MgSO$_4$ and concentrated. The crude material was purified by flash chromatography (from EtOAc/pentane 3/7 to 1/1) to afford the desired product 4 (220 mg, 0.477 mmol) as a white solid. Yield: 76%.

Mp: 144° C. IR (ATR): 3298, 3160, 2986, 1592, 1537, 1445, 1205 cm$^{-1}$. $^1$H NMR (400 MHz, DMSO-d$_6$): δ=1.61 (d, J=6.8 Hz, 3H, CH$_3$), 5.49-5.56 (m, 1H, CH), 7.17 (dd, J=1.6 and 8.4 Hz, 1H, CH), 7.27 (dd, J=2.0 and 8.8 Hz, 1H, CH), 7.32-7.41 (m, 3H, CH), 7.82 (s, 1H, CH), 8.12 (d, J=2.4 Hz, 1H, NH), 8.16 (d, J=8.4 Hz, 1H, CH), 8.38 (s, 1H, CH), 11.11 (br s, 1H, NH), 11.70 (br s, 1H, NH) ppm. $^{13}$C NMR (100 MHz, DMSO-d$_6$): δ=20.9 (CH$_3$), 40.0 (CH), 110.2 (C), 111.0 (C), 113.0 (C), 113.3 (CH), 113.7 (CH), 118.1 (C), 121.3 (CH), 123.3 (CH), 123.4 (CH), 123.7 (CH), 124.2 (CH), 127.8 (C), 128.2 (C), 128.8 (CH), 134.7 (C), 135.0 (C), 163.2 (C) ppm. LRMS (ESI): m/z=458, 460 and 462 [(M−H)$^-$].

4.2 Synthesis of Compound 5

N-(1-(5-bromo-1H-indol-3-yl)ethyl)-5-fluoro-1H-indole-3-carboxamide 5

To a stirred solution of indolic amine (gb) (72 mg, 0.3 mmol) and 5-fluoro-1H-indole-3-carboxylic acid (20 (59 mg, 0.33 mmol) in 5 mL of dry CH$_2$Cl$_2$, 1-ethyl-3-(3-dimethylaminopropyl)carbodiimide (EDCI, 5 mg, 0.33 mmol) was added at room temperature. The resulting mixture was stirred overnight. Then CH$_2$Cl$_2$ was evaporated then EtOAc (20 mL) and a 1M aqueous solution of hydrochloric acid (20 mL) were added. After extraction, organic phase was washed with an aqueous solution of hydrochloric acid, a 5% aqueous solution of Na$_2$CO$_3$, brine, dried over anhydrous MgSO$_4$, filtered, and concentrated under vacuum. Purification of the crude product by column chromatography using EtOAc-pentane (from 1/9 to 8/2) yielded the pure bis-indole 5 (60 mg, 0.226 mmol) as a beige foam. Yield: 50%.

IR (neat): 3455, 3240, 2975, 2870, 1740, 1595, 1530, 1460, 1425, 1205, 1170, 1080, 1005, 930, 850, 760 cm$^{-1}$. $^1$H NMR (300 MHz, CD$_3$OD-DMSO-d$_6$): δ=1.60 (d, J=6.8 Hz, 3H), 5.49 (q, J=6.8 Hz, 1H), 6.99 (dt, J=2.6 and 9.0 Hz, 1H), 7.09 (dd, J=1.9 and 8.7 Hz, 1H), 7.19-7.23 (m, 2H), 7.44 (dd, J=4.4 and 9.0 Hz, 1H), 7.65 (dd, J=2.6 and 9.6 Hz, 1H), 7.74 (d, J=7.7 Hz, 3H), 8.18 (s, 1H) ppm. $^{13}$C NMR (75.5 MHz, CD$_3$OD-DMSO-d$_6$): δ=21.3, 4.3, 106.9 (d, J=25.1 Hz), 111.9 (d, J=26.6 Hz), 112.3, 112.8, 114.0 (d, J=9.8 Hz), 121.2, 121.4, 121.5, 124.6, 126.2, 127.5, 134.7, 134.9, 135.1, 160.0 (d, J=235.1 Hz), 168.8, 175.5 ppm. LRMS (ESI): m/z=422 and 424 [(M+Na)$^+$].

Example 5: Preparation of N-Methyl Indolic Acids (R'$_6$=Me)

The following procedure given for R=CH$_2$NHBoc, R$_3$ and R'$_3$=Br, and R'$_6$=Me, all other substituents being H, is representative of these compounds (SCHEME IV).

SCHEME IV

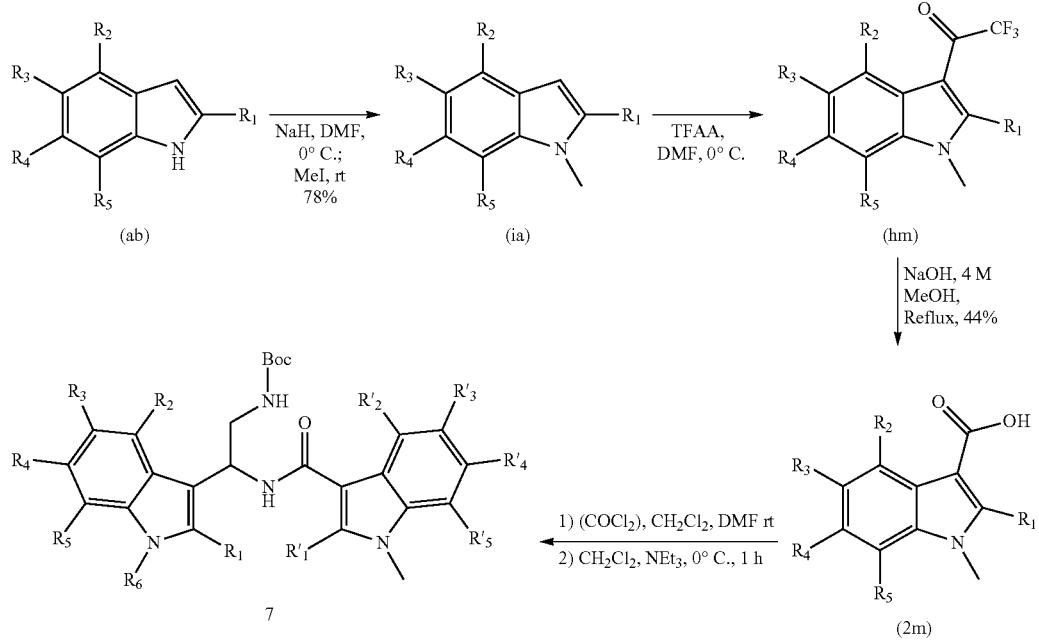

7: R = CH$_2$NHBoc, R$_3$ and R'$_3$ = Br, R'$_6$ = Me, R$_1$, R$_2$, R$_4$-R$_6$ and R'$_1$, R'$_2$, R'$_4$-R'$_5$ = H

5.1: Synthesis of the Compound 7

5-Bromo-1-methyl-1H-indole (ia)

Commercially available, for example:

Sigma-Aldrich P O Box 14508 St. Louis, Mo. 63178 USA or American Custom Chemicals Corp. P O Box 262527 San Diego, Calif. 92196-2527 USA In a dry flask under argon, 5-bromoindole (ab) (1.5 g, 7.65 mmol) was dissolved in dry DMF (15 mL). After cooling this mixture to 0° C., sodium hydride (367 mg, 9.18 mmol, 60% in oil) was added to form the anion. This solution was stirred at 0° C. for 30 minutes. Then, methyl iodide (0.525 mL, 1.196 g, 8.42 mmol) was added. The resulting mixture was then stirred at room temperature for 5 hours and quenched with water. After dilution in ethyl acetate and separation, the organic layer was washed with brine three times, dried over anhydrous MgSO$_4$ and concentrated. The desired product (ia) (1.24 g, 5.9 mmol) was obtained as a yellow solid. Yield: 77%.

$^1$H NMR (300 MHz, CDCl$_3$): δ=3.79 (s, 3H, CH$_3$), 6.42 (d, J=3.3 Hz, 1H, CH), 7.03 (d, J=3.3 Hz, 1H, CH), 7.18 (d, J=8.7 Hz, 1H, CH), 7.25-7.31 (m, 1H, CH), 7.74 (d, J=1.8 Hz, 1H, CH) ppm.

1-(5-Bromo-1-methyl-1H-indol-3-yl)-2,2,2-trifluoroethanone (hm)

In a dry flask under argon, compound (ia) (1.24 g, 5.90 mmol) was dissolved in dry DMF (6 mL). This solution was cooled to 0° C. and trifluoroacetic anhydride (1.23 mL, 1.860 g, 8.86 mmol) was added dropwise. The mixture was stirred at 0° C. for 3 h30 then quenched with water. The crude mixture was filtered to afford a solid. This solid was washed twice with water and dissolved in ethyl acetate. The organic layer was washed with NaHCO$_3$ saturated aqueous solution and brine, dried over anhydrous MgSO$_4$ and evaporated. The desired product (hm) (1.62 g, 5.29 mmol) was obtained as a solid without further purification. Yield: 90%.

$^1$H NMR (300 MHz, CDCl$_3$): δ=3.90 (s, 3H, CH$_3$), 7.26 (d, J=8.7 Hz, 1H, CH), 7.49 (dd, J=2.1 and 8.7 Hz, 1H, CH), 7.88 (d, J=1.5 Hz, 1H, CH), 8.56 (d, J=2.1 Hz, 1H, CH) ppm.

5-Bromo-1-methyl-1H-indole-3-carboxylic acid (2m)

Commercially available, for example:

Thermo Fisher Scientific Brand: Acros Organics, Acros Organics, part of Thermo Fisher Scientific Janssens Pharmaceuticalaan 3A Geel, 2440 Belgium Synthesis, see references: M. Duflos, M.-R. Nourrisson, J. Brelet, J. Courant, G. LeBaut, N. Grimaud, J.-Y. Petit, *European Journal of Medicinal Chemistry* 2001, 36, 545-553. A. Breteche, M. Duflos, A. Dassonville, M.-R. Nourrisson, J. Brelet, G. Le Baut, N. Grimaud, J.-Y. Petit *Journal of Enzyme Inhibition and Medicinal Chemistry* 2002, 17, 415-424.

A flask was charged with compound (hm) (1.53 g, 5.03 mmol) and a 4M aqueous solution of sodium hydroxide (40 mL). This mixture was refluxed for 2 h30. Methanol (10 mL) was added to the mixture which was refluxed overnight, then carefully acidified with 6M HCl. During this acidification, the carboxylic acid precipitated. The resulting suspension was filtered. The solid was washed with water and dissolved in a mixture of ethyl acetate/methanol (about 9/1). The organic layer was dried over anhydrous MgSO$_4$ and evaporated under vacuum. The desired product (2m) (560 mg, 2.20 mmol) was obtained as a beige solid. Yield: 44%.

$^1$H NMR (300 MHz, DMSO-d$_6$): δ=3.84 (s, 3H, CH$_3$), 7.38 (dd, J=2.1 and 8.7 Hz, 1H, CH), 7.52 (d, J=8.7 Hz, 1H, CH), 8.08 (s, 1H, CH), 8.13 (d, J=2.1 Hz, 1H, CH), 12.13 (br s, 1H, OH) ppm. $^{13}$C NMR (75.5 MHz, DMSO-d$_6$): δ=33.1 (CH$_3$), 105.7 (C), 112.8 (CH), 114.2 (C), 122.7 (CH), 124.6 (CH), 128.0 (C), 135.7 (C), 137.1 (CH), 165.1 (C) ppm.

tert-Butyl (2-(5-bromo-1-methyl-1H-indole-3-carboxamido)-2-(5-bromo-1H-indol-3-yl)ethyl) carbamate 7

In a dry flask under argon, the carboxylic acid (2m) (100 mg, 0.39 mmol) was dissolved in dry dichloromethane (3 mL) and few drops of dry DMF. The sluggish solution was cooled to 0° C. and freshly distilled oxalyl chloride (60 mg, 0.47 mmol) was added dropwise. The mixture was then stirred for 4 hours at room temperature and directly evaporated with toluene under reduced pressure. The desired acid chloride was obtained as a yellow solid and used straightaway. In a dry flask under argon, the amine (1b) (70 mg, 0.198 mmol) and triethylamine (32 mg, 0.316 mmol) were dissolved in 2 mL of dry dichloromethane. After cooling this solution to 0° C., the acid chloride previously obtained (65 mg, 0.237 mmol) was added and the mixture was stirred at 0° C. for one hour. The reaction was then quenched with saturated NaHCO$_3$ solution and extracted twice with ethyl acetate. The organic layer was washed with water, dried over anhydrous MgSO$_4$ and concentrated. After purification by flash chromatography (EtOAc/pentane, from 1/1 to neat EtOAc), the desired product 7 (35 mg, 0.059 mmol) was obtained as a white solid. Yield: 30%.

Mp: 233° C. IR (ATR): 3365, 3271, 1668, 1609, 1529, 1513, 1466, 1231, 1156 cm$^{-1}$. $^1$H NMR (400 MHz, DMSO-d$_6$): δ=1.32 (s, 9H, CH$_3$), 3.40-3.54 (m, 2H, CH$_2$), 3.81 (s, 3H, CH$_3$), 5.44-5.50 (m, 1H, CH), 6.92 (br s, 1H, NH), 7.17 (dd, J=2.0 and 8.4 Hz, 1H, CH), 7.30-7.37 (m, 3H, CH and NH), 7.48 (d, J=8.8 Hz, 1H, CH), 7.84 (s, 1H, CH), 8.04-8.07 (m, 2H, CH and NH), 8.30 (s, 1H, CH), 11.13 (br s, 1H, NH) ppm. $^{13}$C NMR (100 MHz, DMSO-d$_6$): δ=28.1 (CH$_3$), 33.0 (CH$_3$), 44.2 (CH$_2$), 45.1 (CH), 77.6 (C), 109.1 (C), 111.7 (C), 112.3 (CH), 113.3 (C), 113.4 (CH), 114.9 (C), 121.1 (CH), 123.2 (CH), 123.3 (CH), 124.0 (CH), 124.3 (CH), 128.19 (C), 128.23 (C), 132.9 (CH), 134.7 (C), 135.3 (C), 155.8 (C), 163.2 (C) ppm.

Example 6: Preparation of Indolic Derivatives Wherein R=(CH$_2$)$_n$OH, CO$_2$H, CO$_2$Alkyl or Cycloalkyl The following procedure given for R=CH$_2$OH, R$_3$ and R'$_3$=Br, all other substituents being H, is representative of these compounds (SCHEME V).

SCHEME V

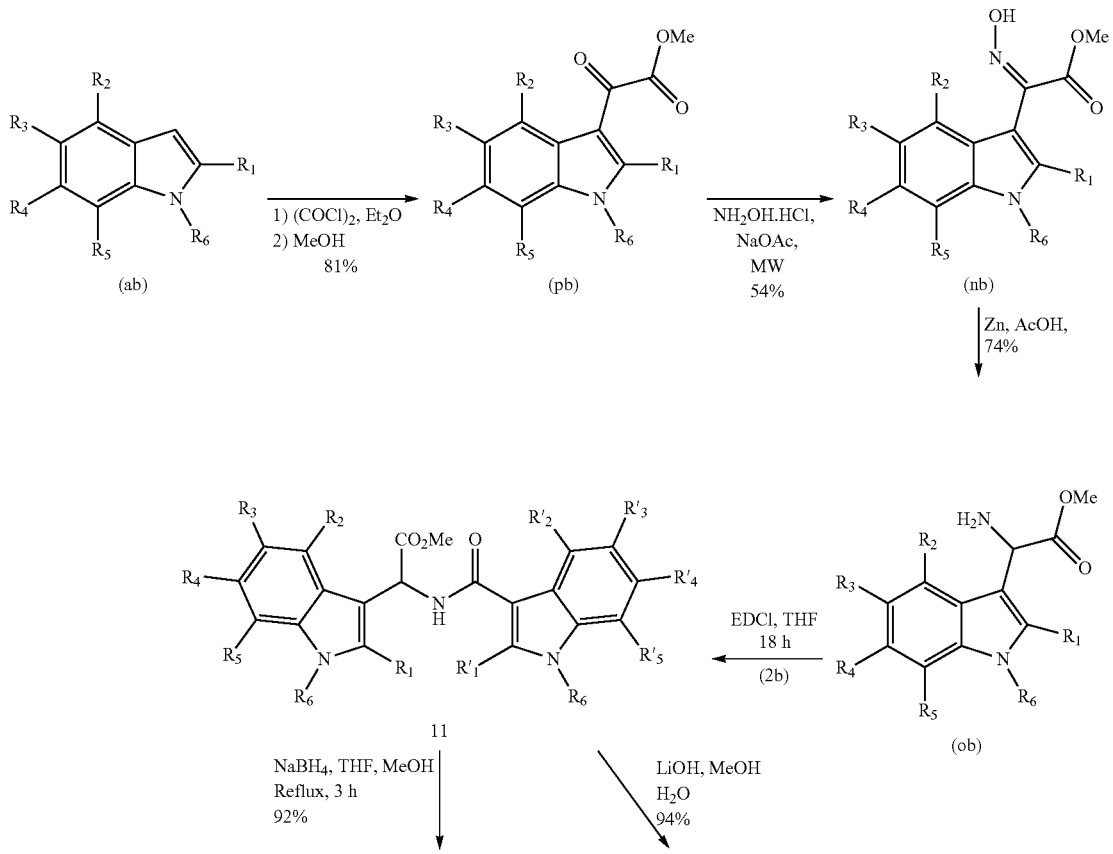

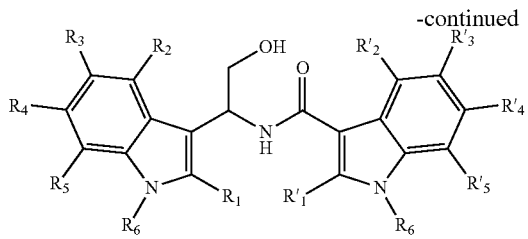
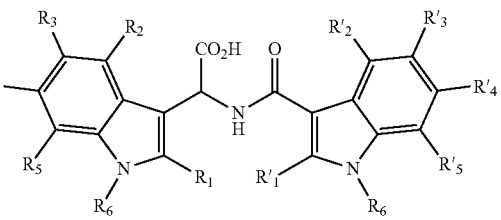

11: R = CO₂Me, R₃ and R′₃ = Br, R₁, R₂, R₄-R₆ and R′₁, R′₂, R′₄-R′₆ = H
12: R = CO₂H, R₃ and R′₃ = Br, R₁, R₂, R₄-R₆ and R′₁, R′₂, R′₄-R′₆ = H
13: R = CH₂OH, R₃ and R′₃ = Br, R₁, R₂, R₄-R₆ and R′₁, R′₂, R′₄-R′₆ = H

6.1: Preparation of Compound 11

Methyl 2-(5-bromo-1H-indol-3-yl)-2-oxoacetate (pb)

A dry flask was charged with 5-bromoindole (ab) (4.0 g, 20.4 mmol) and dry diethyl ether (60 mL) under argon. This solution was cooled to 0° C. and freshly distilled oxalyl chloride (2.10 mL, 24.5 mmol) was added. The solution turned rapidly yellow. After stirring for 1 h30 at 0° C., the mixture was quenched by addition of methanol (16.4 mL, 408 mmol) at 0° C. and stirred for 10 minutes at room temperature. The solution was concentrated and the yellow powder was washed twice with diethyl ether. The yellow solid was then dried under vacuum to afford the desired product (pb) (4.68 g, 16.60 mmol) without any further purification. Yield: 81%.

$^1$H NMR (300 MHz, DMSO-d$_6$): δ=3.89 (s, 3H, CH$_3$), 7.43 (dd, J=1.6 and 8.8 Hz, 1H, CH), 7.54 (d, J=8.8 Hz, 1H, CH), 8.29 (d, J=1.6 Hz, 1H, CH), 8.50 (d, J=3.3 Hz, 1H, CH), 12.66 (br s, 1H, NH) ppm. $^{13}$C NMR (75.5 MHz, DMSO-d$_6$): δ=52.5 (CH$_3$), 111.8 (C), 114.8 (CH), 115.5 (C), 123.2 (CH), 126.4 (CH), 127.3 (C), 135.4 (C), 139.2 (CH), 163.3 (C), 178.3 (C) ppm. LRMS (ESI): m/z=280 and 282 [(M−H)⁻].

Methyl 2-(5-bromo-1H-indol-3-yl)-2-(hydroxyimino)acetate (nb)

A vial was charged with the keto-ester (pb) (600 mg, 2.13 mmol), methanol (10 mL), water (4 mL), sodium acetate (1.74 g, 21.27 mmol) and hydroxylamine hydrochloride (1.47 g, 21.27 mmol). The vial was sealed and heated at 100° C. under microwaves activation for 45 minutes. The resulting brown solution was diluted with ethyl acetate, washed with 1M aqueous HCl and water. The organic layer was dried over anhydrous MgSO$_4$ and concentrated under vacuum. The crude material was purified by flash chromatography (EtOAc/pentane, 4/6) to afford the desired product (nb) (342 mg, 1.15 mmol) as a red-brown solid (2 isomers, ratio, 1/1). Yield: 54%.

Isomer 1
$^1$H NMR (400 MHz, DMSO-d$_6$): δ=3.83 (s, 3H, CH$_3$), 7.27 (d, J=8.8 Hz, 1H, CH), 7.42 (d, J=8.8 Hz, 1H, CH), 7.50 (s, 1H, CH), 8.02 (s, 1H, CH), 11.87 (br s, 1H, NH), 12.2 (s, 1H, OH) ppm. $^{13}$C NMR (100 MHz, DMSO-d$_6$): δ=62.1 (CH$_3$), 116.5 (C), 122.2 (CH), 123.8 (CH), 132.9 (CH), 134.0 (CH), 136.7 (C), 141.4 (CH), 144.1 (C), 157.2 (C), 175.1 (C) ppm.

Isomer 2
$^1$H NMR (400 MHz, DMSO-d$_6$): δ=3.87 (s, 3H, CH$_3$), 7.32 (d, J=8.8 Hz, 1H, CH), 7.42 (d, J=8.8 Hz, 1H, CH), 7.55 (s, 1H, CH), 8.13 (d, J=1.6 Hz, 1H, CH), 11.31 (s, 1H, OH), 11.79 (br s, 1H, NH) ppm. $^{13}$C NMR (100 MHz, DMSO-d$_6$): δ=62.3 (CH$_3$), 113.5 (C), 122.9 (CH), 124.0 (C), 133.5 (CH), 135.0 (CH), 135.4 (C), 138.7 (CH), 145.5 (C), 153.4 (C), 174.1 (C) ppm.

IR (ATR): 3359, 2953, 1719, 1607, 1531, 1419, 1235, 1106 cm⁻¹. LRMS (ESI): m/z=295 and 297 [(M−H)⁻].

Methyl 2-amino-2-(5-bromo-1H-indol-3-yl)acetate (ob)

The indolic oxime (nb) (1.67 g, 5.62 mmol) was dissolved in THF (30 mL). This solution was then added to a cold (0° C.) mixture of acetic acid (55 mL) and water (55 mL). Once the temperature of the mixture was closed to 0° C., zinc dust (3.67 g, 56.23 mmol) was slowly added (over 15 minutes). After addition of zinc, the mixture was stirred for one hour at 0° C. During the reaction, the colour of the mixture was changed from red to green. Ethyl acetate (80 mL) was then added to the solution and the acetic acid was quenched by addition of potassium carbonate. The basic (pH=8-9) aqueous layer was extracted twice with ethyl acetate. The organic layers were combined, washed with brine, dried over anhydrous MgSO$_4$ and concentrated under vacuum. The residue was washed twice with pentane and dried under vacuum to afford the desired amine (ob) (1.17 g, 4.13 mmol) as a brown solid. Yield: 74%.

$^1$H NMR (400 MHz, DMSO-d$_6$): δ=2.21 (br s, 2H, NH$_2$), 3.60 (s, 3H, CH$_3$), 4.76 (s, 1H, CH), 7.19 (d, J=8.8 Hz, 1H, CH), 7.33 (d, J=8.8 Hz, 1H, CH), 7.36 (d, J=2.0 Hz, 1H, CH), 7.80 (d, J=2.0 Hz, 1H, CH), 11.20 (br s, 1H, NH) ppm. $^{13}$C NMR (100 MHz, DMSO-d$_6$): δ=51.3 (CH), 51.6 (CH$_3$), 111.2 (C), 113.4 (CH), 114.3 (C), 121.3 (CH), 123.5 (CH), 124.7 (CH), 127.3 (C), 134.9 (C), 174.7 (C) ppm. LRMS (ESI): m/z=281 and 283 [(M−H)⁻].

Methyl 2-(5-bromo-1H-indol-3-yl)-2-(5-bromo-1H-indole-3-carboxamido)acetate 11

In a flask, the amine (ob) (1.13 g, 4.0 mmol) was dissolved in 50 mL of THF. To this solution, 5-bromo-1H-indole-3-carboxylic acid (2b) (862 mg, 3.6 mmol) and 1-ethyl-3-(3-dimethylaminopropyl) carbodiimide (EDCI, 680 mg, 0.768 mL, 4.38 mmol) were added. The reacting mixture was stirred overnight at room temperature. The crude material was then diluted in a large amount of ethyl acetate. The organic layer was washed twice with 1N aqueous HCl solution and once with brine. The organic layer was dried over anhydrous MgSO$_4$ and concentrated. The crude material was purified by flash chromatography (EtOAc/pentane, 1/1 then 7/3 and neat ethyl acetate) to afford the desired product 11 as a white solid. Yield: 75%. This solid was washed with pentane to remove entirely ethyl acetate (1.10 g, 2.18 mmol). Yield: 61%.

Mp: 126° C. IR (ATR): 3223, 3031, 1752, 1704, 1597, 1537, 1435, 1372, 1204 cm$^{-1}$. $^1$H NMR (300 MHz, DMSO-d$_6$): δ=3.67 (s, 3H, CH$_3$), 5.82 (d, J=6.0 Hz, 1H, CH), 7.24 (dd, J=1.8 and 6.6 Hz, 1H, CH), 7.28 (dd, J=2.1 and 8.7 Hz, 1H, CH), 7.39 (d, J=8.7 Hz, 1H, CH), 7.41 (d, J=8.7 Hz, 1H, CH), 7.53 (d, J=2.4 Hz, 1H, CH), 7.80 (d, J=2.1 Hz, 1H, CH), 8.29 (d, J=2.4 Hz, 1H, CH), 8.33 (d, J=1.8 Hz, 1H, CH), 8.55 (d, J=6.0 Hz, 1H, NH), 11.41 (br s, 1H, NH), 11.78 (br s, 1H, NH) ppm. $^{13}$C NMR (75.5 MHz, DMSO-d$_6$): δ=49.3 (CH), 51.9 (OCH$_3$), 108.9 (C), 109.0 (C), 111.6 (C), 113.2 (C), 113.6 (CH), 113.8 (CH), 121.2 (CH), 123.2 (CH), 123.9 (CH), 124.4 (CH), 126.5 (CH), 127.7 (C), 128.2 (C), 130.1 (CH), 134.7 (C), 134.9 (C), 164.2 (C), 171.6 (C) ppm. LRMS (ESI): m/z=502, 504 and 506 [(M−H)$^-$].

6.2: Preparation of Compound 12

2-(5-Bromo-1H-indol-3-yl)-2-(5-bromo-1H-indole-3-carboxamido) acetic acid 12

The ester 11 (400 mg, 0.80 mmol) was dissolved in a mixture of methanol/water (8 mL/5.3 mL). Lithium hydroxide monohydrate (133 mg, 3.20 mmol) was added to this mixture and the solution was stirred for 1 h45 at 40° C. The reaction was then quenched with 27 mL of 1M aqueous HCl and extracted three times with ethyl acetate. The organic layers were combined, washed with brine, dried over anhydrous MgSO$_4$ and evaporated under vacuum. A brownish solid was obtained. This latter was washed with pentane to remove totally ethyl acetate. The desired carboxylic acid 12 (370 mg, 0.75 mmol) was obtained without further purification as a beige solid. Yield: 94%.

Mp: 195° C. IR (ATR): 3406, 3268, 2974, 1715, 1614, 1529, 1446, 1187, 1098 cm$^{-1}$. $^1$H NMR (400 MHz, DMSO-d$_6$): δ=5.78 (d, J=6.8 Hz, 1H, CH), 7.24 (dd, J=2.0 and 8.8 Hz, 1H, CH), 7.28 (dd, J=2.0 and 8.8 Hz, 1H, CH), 7.39 (d, J=8.8 Hz, 1H, CH), 7.41 (d, J=8.8 Hz, 1H, CH), 7.53 (d, J=2.4 Hz, 1H, CH), 7.84 (d, J=2.0 Hz, 1H, CH), 8.31 (d, J=2.4 Hz, 1H, CH), 8.35 (d, J=2.0 Hz, 1H, CH), 8.46 (d, J=6.8 Hz, 1H, NH), 11.37 (br s, 1H, NH), 11.78 (br s, 1H, NH), 12.54 (br s, 1H, OH) ppm. $^{13}$C NMR (100 MHz, DMSO-d$_6$): δ=49.2 (CH), 109.2 (C), 109.9 (C), 111.5 (C), 113.2 (C), 113.6 (CH), 113.8 (CH), 121.5 (CH), 123.2 (CH), 123.8 (CH), 124.4 (CH), 126.4 (CH), 127.8 (C), 128.2 (C), 130.0 (CH), 134.7 (C), 134.9 (C), 164.1 (C), 172.6 (C) ppm. LRMS (ESI): m/z=488, 490 and 492 [(M−H)$^-$].

6.3: Preparation of Compound 13

5-Bromo-N-(1-(5-bromo-1H-indol-3-yl)-2-hydroxyethyl)-1H-indole-3-carboxamide 13

The ester 11 (150 mg, 0.30 mmol) was dissolved in a mixture of THF/methanol (5 mL/1 mL). To this solution, NaBH$_4$ (114 mg, 3.0 mmol) was added portionwise. During the addition, the solution was fizzing. The mixture was refluxed for 3 hours then diluted in ethyl acetate. The organic layer was washed with water and brine, dried over anhydrous MgSO$_4$ and concentrated. The residue was washed with pentane to afford the pure desired alcohol 13 (130 mg, 0.274 mmol) as a white powder. Yield: 92%.

Mp: 155° C. IR (ATR): 3282, 2948, 1708, 1593, 1541, 1432, 1255, 1204, 1041 cm$^{-1}$. $^1$H NMR (300 MHz, DMSO-d$_6$): δ=3.84 (t, J=6.3 Hz, 2H, CH$_2$), 4.87 (t, J=6.3 Hz, 1H, OH), 5.42 (ddd, J=6.3, 6.3 and 8.4 Hz, 1H, CH), 7.16 (dd, J=1.8 and 8.7 Hz, 1H, CH), 7.26 (dd, J=2.1 and 8.4 Hz, 1H, CH), 7.33 (d, J=8.4 Hz, 1H, CH), 7.37 (s, 1H, CH), 7.40 (d, J=8.7 Hz, 1H, CH), 7.86 (d, J=1.8 Hz, 1H, CH), 8.06 (d, J=1.8 Hz, 1H, NH), 8.17 (s, 1H, CH), 8.33 (d, J=2.1 Hz, 1H, CH), 11.12 (br s, 1H, NH), 11.71 (br s, 1H, NH) ppm. $^{13}$C NMR (75.5 MHz, DMSO-d$_6$): δ=47.3 (CH), 63.8 (CH$_2$), 110.2 (C), 111.0 (C), 113.0 (C), 113.2 (CH), 113.7 (CH), 114.7 (C), 121.2 (CH), 123.2 (CH), 123.3 (CH), 124.2 (CH), 124.4 (CH), 128.1 (C), 128.2 (C), 129.0 (CH), 134.7 (C), 134.8 (C), 163.7 (C) ppm. LRMS (ESI): m/z=474, 476 and 478 [(M−H)$^-$].

Example 7: Preparation of Indolic Derivatives Wherein R=CONH(CH$_2$)$_n$OH and CONH(CH$_2$)$_n$NR$_a$R$_b$ The following procedure given for R=CONH(CH$_2$)$_n$OH, CONH(CH$_2$)$_n$NH$_2$ and R$_3$ and R'$_3$=Br, all other substituents being H, is representative of these compounds (SCHEME VI).

SCHEME VI

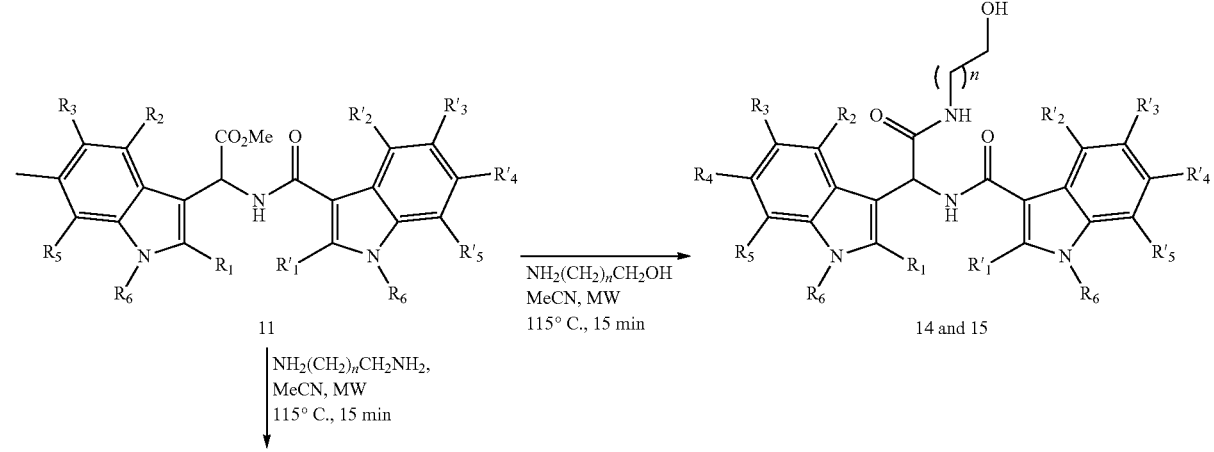

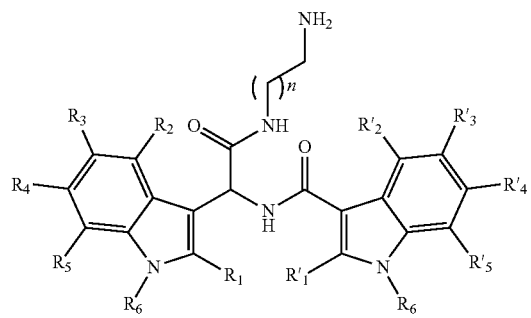

14: R = CONHCH$_2$CH$_2$OH, R$_3$ and R'$_3$ = Br, R$_1$, R$_2$, R$_4$-R$_6$ and R'$_1$, R'$_2$, R'$_4$-R'$_6$ = H
15: R = CONH(CH$_2$)$_3$CH$_2$OH, R$_3$ and R$_3$ = Br, R$_1$, R$_2$, R$_4$-R$_6$ and R'$_1$, R'$_2$, R'$_4$-R'$_6$ = H
16: R = CONH(CH$_2$)$_3$CH$_2$NH$_2$, R$_3$ and R'$_3$ = Br, R$_1$, R$_2$, R$_4$-R$_6$ and R'$_1$, R'$_2$, R'$_4$-R'$_6$ = H

7.1: Preparation of Compound 14

5-Bromo-N-(1-(5-bromo-1H-indol-3-yl)-2-((2-hydroxyethyl)amino)-2-oxoethyl)-1H-indole-3-carboxamide 14

A vial was charged with the ester 11 (50 mg, 0.1 mmol), potassium carbonate (27 mg, 0.2 mmol), ethanolamine (1.0 g) and acetonitrile (1 mL). This mixture was heated at 115° C. for 15 minutes under microwave activation. The crude material was diluted in ethyl acetate, washed three times with water, dried over anhydrous MgSO$_4$ and concentrated. The residue was recrystallized in methanol to afford a white solid 14 (40 mg, 0.075 mmol). Yield: 75%.

Mp: 164° C. IR (ATR): 3420, 3230, 2935, 1644, 1605, 1531, 1495, 1455, 1194 cm$^{-1}$. $^1$H NMR (300 MHz, DMSO-d$_6$): δ=3.15-3.24 (m, 2H, CH$_2$), 3.40-3.46 (m, 2H, CH$_2$), 4.65 (t, J=5.4 Hz, 1H, OH), 5.92 (d, J=7.8 Hz, 1H, CH), 7.19 (dd, J=2.1 and 8.7 Hz, 1H, CH), 7.27 (dd, J=2.1 and 8.7 Hz, 1H, CH), 7.33-7.41 (m, 3H, CH), 7.86 (d, J=1.8 Hz, 1H, CH), 8.15 (t, J=6.0 Hz, 1H, NH), 8.24 (d, J=7.8 Hz, 1H, NH), 8.28 (s, 1H, CH), 8.32 (d, J=2.1 Hz, 1H, CH), 11.24 (s, 1H, NH), 11.76 (br s, 1H, NH) ppm. $^{13}$C NMR (75.5 MHz, DMSO-d$_6$): δ=41.6 (CH$_2$), 49.2 (CH), 59.6 (CH$_2$), 109.4 (C), 111.3 (C), 112.2 (C), 113.2 (C), 113.4 (C), 113.8 (C), 121.4 (CH), 123.1 (CH), 123.5 (CH), 124.3 (CH), 125.7 (CH), 127.9 (C), 128.1 (C), 129.8 (CH), 134.7 (C), 134.8 (C), 163.6 (C), 170.6 (C) ppm.

7.2: Preparation of Compound 15

5-Bromo-N-(1-(5-bromo-1H-indol-3-yl)-2-((4-hydroxybutyl)amino)-2-oxoethyl)-1H-indole-3-carboxamide 15

A vial was charged with the ester 11 (50 mg, 0.1 mmol), potassium carbonate (27 mg, 0.2 mmol), 4-aminobutanol (1.0 g) and acetonitrile (1 mL). This mixture was heated at 115° C. for 15 minutes under microwave activation. The crude material was diluted in ethyl acetate, washed three times with water, dried over anhydrous MgSO$_4$ and concentrated. The residue was recrystallized in methanol/EtOAc to afford the white solid 15 (37 mg, 0.066 mmol). Yield: 66%.

Mp: 187° C. IR (ATR): 3396, 3246, 2932, 1615, 1526, 1446, 1194 cm$^{-1}$. $^1$H NMR (400 MHz, DMSO-d$_6$): δ=1.36-1.47 (m, 4H, CH$_2$), 3.08-3.13 (m, 2H, CH$_2$), 3.30-3.38 (m, 2H, CH$_2$), 4.33 (br s, 1H, OH), 5.89 (d, J=8.0 Hz, 1H, CH), 7.19 (dd, J=2.1 and 8.7 Hz, 1H, CH), 7.27 (dd, J=2.1 and 8.7 Hz, 1H, CH), 7.33-7.41 (m, 3H, CH), 7.87 (d, J=1.8 Hz, 1H, CH), 8.15 (t, J=6.0 Hz, 1H, NH), 8.20 (d, J=7.8 Hz, 1H, NH), 8.28 (s, 1H, CH), 8.32 (d, J=2.1 Hz, 1H, CH), 11.22 (br s, 1H, NH) ppm. $^{13}$C NMR (100 MHz, DMSO-d$_6$): δ=25.6 (CH$_2$), 29.7 (CH$_2$), 39.25 (CH$_2$), 49.2 (CH), 60.3 (CH$_2$), 109.4 (C), 111.3 (C), 112.3 (C), 113.1 (C), 113.4 (CH), 113.7 (CH), 121.4 (CH), 123.1 (CH), 123.5 (CH), 124.3 (CH), 125.6 (CH), 127.8 (C), 128.1 (C), 129.8 (CH), 134.6 (C), 134.8 (C), 163.5 (C), 170.2 (C) ppm.

7.3: Preparation of Compound 16

N-(2-((4-Aminobutyl)amino)-1-(5-bromo-1H-indol-3-yl)-2-oxoethyl)-5-bromo-1H-indole-3-carboxamide 16

A vial was charged with the ester 11 (60 mg, 0.119 mmol), potassium carbonate (58 mg, 0.214 mmol), 4-aminobutanol (1.2 g) and acetonitrile (1.5 mL). This mixture was heated at 115° C. for 15 minutes under microwave activation. The crude material was diluted in ethyl acetate, washed three times with water, dried over anhydrous MgSO$_4$ and concentrated to afford the product 16 (39 mg, 0.07 mmol) as a white solid. Yield: 59%.

Mp: 205° C. IR (ATR): 3256, 2928, 2869, 1610, 1531, 1444, 1205 cm$^{-1}$. $^1$H NMR (300 MHz, DMSO-d$_6$): δ=1.17-1.33 (m, 2H, CH$_2$), 1.33-1.47 (m, 2H, CH$_2$), 2.43-2.52 (m, 2H, CH$_2$), 3.05-3.14 (m, 2H, CH$_2$), 5.89 (d, J=7.8 Hz, 1H, CH), 7.19 (dd, J=1.8 and 8.7 Hz, 1H, CH), 7.27 (dd, J=1.8 and 8.7 Hz, 1H, CH), 7.33-7.41 (m, 3H, CH), 7.88 (d, J=1.8 Hz, 1H, CH), 8.14-8.24 (m, 2H, 2 NH), 8.28-8.32 (m, 2H, CH), 11.22 (br s, 1H, NH) ppm.

Example 8: Comparative Examples

The coupling of compound (1b) with benzoic acid, p-bromobenzylcarboxylic acid, trifluoroacetic acid or pyridine-3-carboxylic acid, (nicotinic acid) gives compounds 8, 8a, 9 and 10 respectively:

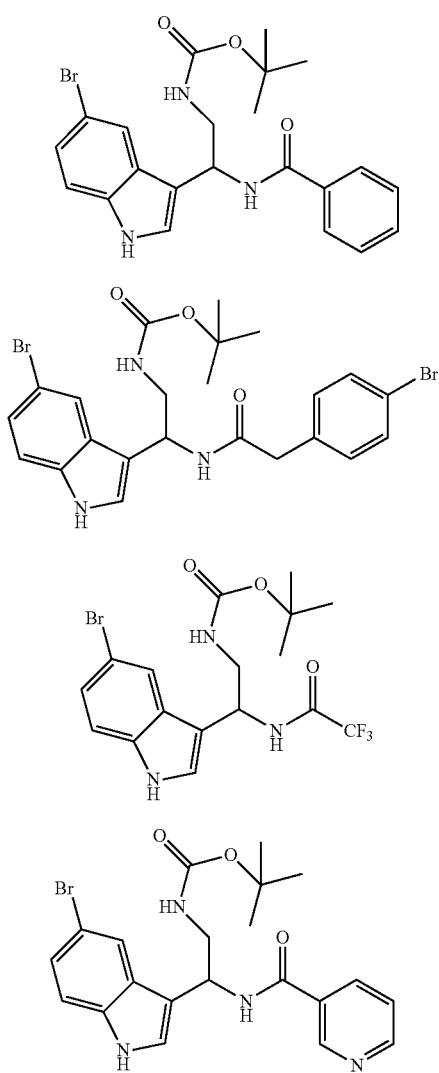

Synthesis of Compounds 8, 8a, 9 and 10 t-Butyl (2-benzamido-2-(5-bromo-1H-indol-3-yl)ethyl) carbamate 8

In a dry flask under argon, the [2-amino-2-(5-bromo-1H-indol-3-yl)ethyl]carbamic acid tert-butyl ester (1b) (60 mg, 0.17 mmol) and triethylamine (0.028 mL, 0.20 mmol) were dissolved in 2 mL of dry dichloromethane. After cooling this solution to 0° C., benzoyl chloride (0.020 mL, 0.17 mmol) was added dropwise and the mixture was stirred at 0° C. for 15 minutes. The reaction was then quenched with water and diluted with ethyl acetate. The organic layer was washed with 1M aqueous HCl and water, dried over anhydrous MgSO$_4$ and concentrated. The crude material was purified by flash chromatography (EtOAc/pentane, from 1/1 to 7/3). After recrystallization in a mixture of ethyl acetate and pentane, the desired product 8 (45 mg, 0.098 mmol) was obtained as a white solid. Yield: 58%.

Mp: 187° C. IR (ATR): 3375, 3310, 1661, 1629, 1519, 1276, 1163 cm$^{-1}$. $^1$H NMR (400 MHz, DMSO-d$_6$): δ=1.33 (s, 9H, CH$_3$), 3.44-3.52 (m, 2H, CH$_2$), 5.42-5.49 (m, 1H, CH), 7.00 (t, J=5.8 Hz, 1H, NH), 7.17 (d, J=6.4 Hz, 1H, CH), 7.32 (d, J=8.8 Hz, 1H, CH), 7.38 (s, 1H, CH), 7.44 (t, J=7.2 Hz, 2H, CH), 7.51 (t, J=7.2 Hz, 1H, CH), 7.82-7.88 (m, 3H, CH and NH), 8.55 (d, J=8.8 Hz, 1H, CH), 11.14 (br s, 1H, NH) ppm. $^{13}$C NMR (100 MHz, DMSO-d$_6$): δ=28.1 (CH$_3$), 44.1 (CH$_2$), 46.2 (CH), 77.6 (C), 111.1 (C), 113.3 (CH), 114.5 (C), 121.0 (CH), 123.4 (CH), 124.2 (CH), 127.3 (CH), 128.0 (CH), 130.9 (CH), 134.61 (C), 134.65 (C), 134.71 (C), 155.8 (C), 165.8 (C) ppm. LRMS (ESI): m/z=480 and 482 [(M+Na)$^+$].

tert-Butyl (2-(p-bromo)benzamido-2-(5-bromo-1H-indol-3-yl)ethyl)carbamate 8a

In a dry flask under argon, 4-bromophenylacetic acid (860 mg, 4 mmol) was dissolved in dry dichloromethane (30 mL) and few drops of dry DMF. The sluggish solution was cooled to 0° C. and freshly distilled oxalyl chloride (0.412 mL, 4.8 mmol) was added dropwise. The mixture was then stirred for 2 hours at room temperature and directly evaporated under reduced pressure.

The desired acid chloride was obtained and dissolved in 4 mL of dichloromethane to make a 1M solution.

In a dry flask under argon, the [2-amino-2-(5-bromo-1H-indol-3-yl)ethyl]carbamic acid tert-butyl ester (1b) (60 mg, 0.17 mmol) and triethylamine (0.033 mL, 0.24 mmol) were dissolved in 1 mL of dry dichloromethane. After cooling this solution to 0° C., the 1M solution of 2-(4-bromophenyl)acetyl chloride previously obtained (0.204 mL, 0.204 mmol) was added dropwise and the mixture was stirred at 0° C. for one hour. The reaction was then quenched with water and diluted with ethyl acetate. The organic layer was washed with a 1M aqueous solution of HCl and water, dried over anhydrous MgSO$_4$ and concentrated. The crude material was purified by flash chromatography (EtOAc/pentane, from 1/1 to 8/2). After recrystallization in a mixture of ethyl acetate and pentane, the desired product 8a (50 mg, 0.09 mmol) was obtained as a white solid. Yield: 54%.

Mp: 131° C. IR (ATR): 3425, 3338, 1678, 1634, 1533, 1488, 1458, 1276, 1169 cm$^{-1}$. $^1$H NMR (400 MHz, DMSO-d$_6$): δ=1.34 (s, 9H, CH$_3$), 3.29-3.43 (m, 2H, CH$_2$), 3.41 (s, 2H, CH$_2$), 5.17-5.23 (m, 1H, CH), 6.82 (t, J=6.0 Hz, 1H, NH), 7.17 (dd, J=1.6 and 8.4 Hz, 1H, CH), 7.21 (d, J=8.4 Hz, 2H, CH), 7.29-7.31 (m, 2H, CH), 7.45 (d, J=8.4 Hz, 2H, CH), 7.66 (s, 1H, CH), 8.30 (d, J=8.8 Hz, 1H, NH), 11.13 (br s, 1H, NH) ppm. $^{13}$C NMR (100 MHz, DMSO-d$_6$): δ=29.1 (CH$_3$), 42.6 (CH$_2$), 45.1 (CH$_2$), 46.3 (CH), 78.6 (C), 112.1 (C), 114.3 (CH), 115.2 (C), 120.4 (C), 122.0 (C), 124.5 (CH), 124.8 (CH), 128.9 (C), 131.9 (CH), 132.1 (CH), 135.8 (C), 136.8 (C), 156.6 (C), 170.0 (C) ppm. LRMS (ESI): m/z=572, 573, 574, 575 and 576 [(M+Na)$^+$].

tert-Butyl (2-(5-bromo-1H-indol-3-yl)-2-(2,2,2-trifluoroacetamido)ethyl)carbamate 9

In a dry flask under argon, the [2-amino-2-(5-bromo-1H-indol-3-yl)ethyl]carbamic acid tert-butyl ester (1b) (80 mg, 0.226 mmol) and triethylamine (0.063 mL, 0.452 mmol) were dissolved in 2 mL of dry dichloromethane. After cooling this solution to 0° C., trifluoroacetic anhydride (0.035 mL, 0.248 mmol) was added and the mixture was stirred at 0° C. for 15 minutes.

The reaction was then quenched with an aqueous saturated solution of NaHCO$_3$ and diluted with dichloromethane. The organic layer was washed with saturated NaHCO$_3$, 1M aqueous HCl and water, dried over anhydrous MgSO$_4$ and concentrated. The crude material was purified by flash chromatography (EtOAc/pentane, 3/7) to afford the desired product 9 (70 mg, 0.156 mmol) as a white solid. Yield: 69%.

IR (ATR): 3441, 3323, 1676, 1533, 1457, 1275, 1162 cm$^{-1}$. $^1$H NMR (300 MHz, DMSO-d$_6$): δ=1.36 (s, 9H, CH$_3$), 3.43-3.48 (m, 2H, CH$_2$), 5.25-5.32 (m, 1H, CH), 7.03 (t, J=5.7 Hz, 1H, NH), 7.20 (dd, J=2.0 and 8.7 Hz, 1H, CH), 7.34 (d, J=8.7 Hz, 1H, CH), 7.38 (d, J=2.0 Hz, 1H, CH), 7.72 (s, 1H, CH), 9.63 (d, J=8.7 Hz, 1H, NH), 11.24 (br s, 1H, NH) ppm. $^{13}$C NMR (75.5 MHz, DMSO-d$_6$): δ=28.0 (CH$_3$), 43.4 (CH$_2$), 46.6 (CH), 77.8 (C), 111.4 (C), 112.3 (C), 133.5 (CH), 120.6 (CH), 123.7 (CH), 127.7 (CH), 155.9 (CF$_3$, J$_{C-F}$=288.8 Hz), 127.7 (C), 134.7 (C), 155.6 (C, J$_{C-F}$=15.8 Hz), 156.0 (C) ppm. LRMS (ESI): m/z=472 and 474 [(M+Na)$^+$].

tert-Butyl (2-(5-bromo-1H-indol-3-yl)-2-(nicotinamido)ethyl) carbamate 10

In a dry flask under argon, nicotinic acid (492 mg, 4 mmol) was dissolved in dry dichloromethane (30 mL) and few drops of dry DMF. The sluggish solution was cooled to 0° C. and freshly distilled oxalyl chloride (0.412 mL, 4.8 mmol) was added dropwise. The mixture was then stirred for 2 hours at room temperature and directly evaporated under reduced pressure. The solid was washed with pentane and dried under vacuum. The desired nicotinoyl chloride hydrochloride was obtained as a white solid and used straightaway.

In a dry flask under argon, the [2-amino-2-(5-bromo-1H-indol-3-yl)ethyl]carbamic acid tert-butyl ester (1b) (80 mg, 0.226 mmol) and triethylamine (0.094 mL, 0.68 mmol) were dissolved in 2 mL of dry dichloromethane. After cooling this solution to 0° C., the nicotinoyl chloride hydrochloride previously obtained (48 mg, 0.271 mmol) was added and the mixture was stirred at 0° C. for 30 minutes. The reaction was then quenched with water and diluted with ethyl acetate. The organic layer was washed with 1M aqueous HCl and water, dried over anhydrous MgSO$_4$ and concentrated. The crude material was purified by flash chromatography (EtOAc/pentane, 1/1 until neat EtOAc). After recrystallization in a mixture of ethyl acetate and pentane, the desired product 10 (60 mg, 0.131 mmol) was obtained as a white solid. Yield: 58%.

Mp: 195° C. IR (ATR): 3325, 3209, 2972, 1682, 1634, 1544, 1272, 1167 cm$^{-1}$. $^1$H NMR (400 MHz, DMSO-d$_6$): δ=1.32 (s, 9H, CH$_3$), 3.46-3.50 (m, 2H, CH$_2$), 5.43-5.49 (m, 1H, CH), 7.03 (t, J=6.0 Hz, 1H, NH), 7.18 (d, J=8.4 Hz, 1H, CH), 7.32 (d, J=8.4 Hz, 1H, CH), 7.40 (s, 1H, CH), 7.49 (dd, J=4.8 and 8.0 Hz, 1H, CH), 7.83 (s, 1H, CH), 8.19 (d, J=8.0 Hz, 1H, CH), 8.68 (d, J=3.6 Hz, 1H, CH), 8.77 (d, J=8.8 Hz, 1H, NH), 9.02 (s, 1H, CH), 11.16 (s, 1H, NH) ppm. $^{13}$C NMR (100 MHz, DMSO-d$_6$): δ=29.1 (CH$_3$), 45.1 (CH$_2$), 47.3 (CH$_3$), 78.6 (C), 112.2 (C), 114.4 (CH), 115.1 (C), 121.9 (CH), 124.2 (CH), 124.4 (CH), 125.3 (CH), 129.0 (C), 131.1 (C), 135.7 (C), 136.0 (CH), 149.5 (CH), 152.6 (CH), 156.8 (C), 165.4 (C) ppm. LRMS (ESI): m/z=459 and 461 [(M+H)$^+$].

Experimental Part—Biology

Example 9: Antibacterial and NorA Efflux Pump Activity Evaluation 9.1: Determination of the Minimum Inhibitory Concentration (MIC)

The microdilution method recommended by the Clinical and Laboratory Standard Institute [M07-A8, Vol. 29, No. 2] was used. The activity of indolic compounds was tested against 29 bacterial strains belonging to 17 different species and 12 different genera (*Staphylococcus, Streptococcus, Enterococcus, Listeria, Bacillus, Haemophilus, Escherichia, Klebsiella, Enterobacter, Serratia, Pseudomonas*, and *Acinetobacter*). Bacterial inocula were prepared in Mueller Hinton broth (MH2, bioMérieux, Marcy L'Etoile, France), supplemented with 10% sheep blood for fastidious species (i.e., *Streptococcus pneumoniae* and *Haemophilus influenzae*). They were dispensed in 96 well microtiter plates (5×10$^5$ CFU/ml of final inoculum). Indolic compounds were added to the wells as to obtain two-fold serial concentrations (0.50-128 mg/L of final concentrations). Plates were incubated at 37° C. in ambient air, or at 37° C. in 5% CO$_2$ enriched atmosphere for fastidious species. MICs were read after 18 hours incubation of cultures, and corresponded to the minimum indolic compound concentration that allowed complete visual growth inhibition of bacteria. Drug-free cultures served as growth controls. Cultures receiving gentamicin, ciprofloxacin or cefotaxime served as positive controls.

The results are given in the following Table II-1:

Compounds of the invention present a strong intrinsic antibacterial activity, in particular against *Staphylococcus aureus* and *Staphylococcus epidermidis*.

Further, compounds of the invention present an anti-*Staphylococcus* activity even against strains presenting an acquired resistance to beta-lactams, including methicillin-resistant *Staphylococcus aureus* (MRSA) strains such as CIP65.25 (MetiR) and ATCC 33592 (MetiR), and/or to glycopeptides such as the VISA (vancomycin-intermediate *S. aureus*) strain ATCC 106414. These multi-resistant bacterial strains are frequently implicated in severe hospital infections.

The lack of intrinsic antibacterial activity of compounds 8, 8a, 9 and 10 shows that the presence of the bis-indoles moieties is essential for the antibacterial activity of the compounds of the invention.

TABLE I-1

| Compounds | 3a | 3b | 3c | 3d | 3e | 3f | 3g | 3h | 3i |
|---|---|---|---|---|---|---|---|---|---|
| *Staphylococcus* (Micrococcaceae Gram+) | | | | | | | | | |
| S. aureus ATCC 25923 | >128 | 8 | 8 | 8 | 16 | 1 | 2 | 1 | 2 |
| S. aureus ATCC 29213 | >128 | 8 | 8 | 8 | 8 | 1 | 2 | 1 | 2 |
| S. aureus ATCC 9144 | | 8 | 8 | 8 | 8 | 1 | 2 | 1 | 2 |
| S. aureus ATCC 6538 | | 8 | 8 | 8 | 8 | 1 | 2 | 1 | 2 |
| S. aureus CIP 65.6 | | 8 | 8 | 8 | 16 | 1 | 2 | 2 | 1 |
| S. aureus CIP 103428 | | 8 | 8 | 8 | 8 | 1 | 1 | 2 | 1 |
| S. aureus CEP 65.25 (MRSA) | | 8 | 8 | 8 | 8 | 2 | 1 | 1 | 1 |
| S. aureus ATCC 33592 (MRSA) | | 8 | 8 | 8 | 32 | 2 | 2 | 2 | 1 |
| S. aureus ATCC 106414 (VISA) | | 8 | 8 | 8 | 8 | 2 | 1 | 1 | 1 |

TABLE I-1-continued

| | | | | | | | | | |
|---|---|---|---|---|---|---|---|---|---|
| S. epidermidis ATCC 12228 | >128 | 8 | 8 | 16 | 8 | 1 | 1 | 1 | 2 |
| S. epidermidis CIP 81.55 | | 8 | 8 | 16 | 8 | 2 | 2 | 1 | 2 |
| S. epidermidis CIP 103627 | | 8 | 8 | 16 | 128 | 1 | 2 | 2 | 2 |
| S. aureus SA-1199B | | 8 | 8 | 8 | 8 | 2 | 2 | 2 | 1 |
| *Streptococcus* and *Enterococcus* (Streptococcaceae Gram+) | | | | | | | | | |
| S. pneumoniae ATCC 49619 | >128 | — | 32 | 64 | — | 32 | 32 | 32 | 32 |
| S. pneumoniae ATCC 6303 | >128 | — | 32 | 64 | — | 32 | 32 | 32 | 32 |
| S. agalactiae (group B) ATCC 12400 | >128 | — | 64 | 64 | — | 32 | 64 | 32 | 32 |
| S. pyogenes (group A) CIP 104226 | >128 | — | 64 | 64 | — | 32 | 64 | 32 | 32 |
| S. mitis CIP 103335 | >128 | — | 64 | 64 | — | 64 | 64 | 32 | 64 |
| E. faecium CIP 54.32 | >128 | — | >128 | 64 | — | >128 | >128 | 32 | 64 |
| E. faecalis ATCC 29212 | >128 | — | >128 | >128 | — | >128 | >128 | >128 | >128 |
| *Listeria* (Listeriaceae Gram+) | | | | | | | | | |
| Listeria innocua CIP 80.11 | >128 | — | >128 | 32 | — | >128 | 128 | 32 | 32 |
| *Bacillus* (Bacillaceae Gram+) | | | | | | | | | |
| Bacillus subtilis CIP 5262 | >128 | — | 64 | 64 | — | 32 | 32 | 32 | 64 |
| Enterobacteriaceae (Gram−) | | | | | | | | | |
| Escherichia. coli ATCC 25922 | >128 | — | >128 | >128 | — | >128 | >128 | >128 | >128 |
| Klebsiella pneumoniae API ATCC 35657 | >128 | — | >128 | >128 | — | >128 | >128 | >128 | >128 |
| Enterobacter cloacae ATCC13047 | >128 | — | >128 | >128 | — | >128 | >128 | >128 | >128 |
| Serratia marcescens CIP 103551 | >128 | — | >128 | >128 | — | >128 | >128 | >128 | >128 |
| Pseudomonadaceae (Gram−) | | | | | | | | | |
| Pseudomonas aeruginosa CIP 5933 | >128 | — | >128 | >128 | — | >128 | >128 | >128 | >128 |
| *Acinetobacter* (Moraxellaceae Gram−) | | | | | | | | | |
| Acinetobacter baumanii ATCC 19606 | >128 | — | >128 | >128 | — | >128 | >128 | >128 | >128 |
| *Haemophilus* (Pasteurellaceae Gram−) | | | | | | | | | |
| Haemophilus influenzae ATCC 49766 | >128 | — | >128 | 64 | — | 32 | 64 | 16 | 16 |

| Compounds | 4 | 5 | 6a | 6b | 7 | 8 | 8a | 10 | 9 |
|---|---|---|---|---|---|---|---|---|---|
| *Staphylococcus* (Micrococcaceae Gram+) | | | | | | | | | |
| S. aureus ATCC 25923 | 2 | 16 | 4 | 4 | >128 | >128 | >128(>32) | >128 | >128 |
| S. aureus ATCC 29213 | 2 | 16 | ≤2 | 4 | >128 | >128 | >32 | 128 | 64 |
| S. aureus ATCC 9144 | 2 | 16 | 4 | 4 | >128 | >128 | >32 | >128 | >128 |
| S. aureus ATCC 6538 | 2 | 16 | 4 | 4 | >128 | >128 | >32 | 64 | 128 |
| S. aureus CIP 65.6 | 2 | >32 | 4 | 4 | >128 | >128 | >32 | >128 | 128 |
| S. aureus CIP 103428 | 2 | 16 | 4 | 4 | >128 | >128 | >32 | 64 | 128 |
| S. aureus CIP 65.25 (MRSA) | 2 | 16 | 4 | 4 | >128 | >128 | >32 | >128 | 128 |
| S. aureus ATCC 33592 (MRSA) | 2 | 16 | 4 | 4 | >128 | >128 | >32 | >128 | 128 |
| S. aureus ATCC 106414 (VISA) | 2 | 16 | 4 | 4 | >128 | >128 | >32 | >128 | 128 |
| S. epidermidis ATCC 12228 | 2 | 16 | 4 | 4 | >128 | >128 | >32 | >128 | >128 |
| S. epidermidis CIP 81.55 | 2 | 16 | 4 | 4 | >128 | >128 | >32 | >128 | >128 |
| S. epidermidis CIP 103627 | 4 | 16 | 4 | 8 | >128 | >128 | >32 | >128 | >128 |
| S. aureus SA-1199B | 2 | — | 4 | 4 | >128 | >128 | >32 | 64 | 128 |
| *Streptococcus* and *Enterococcus* (Streptococcaceae Gram+) | | | | | | | | | |
| S. pneumoniae ATCC 49619 | — | — | 64 | 64 | >128 | >128 | | 128 | >128 |
| S. pneumoniae ATCC 6303 | — | — | 32 | 64 | >128 | >128 | 128 | 128 | >128 |
| S. B ATCC 12400 | — | — | 64 | 128 | >128 | >128 | 64 | 128 | >128 |
| S. pyogenes (group A) CIP 104226 | — | — | 64 | 128 | >128 | >128 | >128 | 128 | >128 |
| S. mitis CIP 103335 | — | — | 64 | 128 | >128 | >128 | >128 | >128 | >128 |
| E. faecium CIP 54.32 | — | — | >128 | >128 | >128 | >128 | >128 | >128 | >128 |
| E. faecalis ATCC 29212 | — | — | >128 | >128 | >128 | >128 | >128 | >128 | >128 |
| *Listeria* (Listeriaceae Gram+) | | | | | | | | | |
| Listeria innocua CIP 80.11 | — | — | >128 | >128 | >128 | >128 | >128 | >128 | >128 |
| *Bacillus* (Bacillaceae Gram+) | | | | | | | | | |
| Bacillus subtilis CIP 5262 | — | — | 64 | 64 | >128 | >128 | >128 | 128 | 128 |
| Enterobacteriaceae (Gram−) | | | | | | | | | |
| Escherichia coli ATCC 25922 | >128 | — | >128 | >128 | >128 | >128 | | >128 | >128 |
| Klebsiella pneumoniae API ATCC 35657 | >128 | — | >128 | >128 | >128 | >128 | 64 | >128 | >128 |
| Enterobacter cloacae API Ec10 ATCC13047 | >128 | — | >128 | >128 | >128 | >128 | | >128 | >128 |
| Serratia marcescens CIP 103551 | >128 | — | >128 | >128 | >128 | >128 | | >128 | >128 |
| Pseudomonadaceae (Gram−) | | | | | | | | | |
| Pseudomonas aeruginosa CIP 5933 | >128 | — | >128 | >128 | >128 | >128 | >128(>32) | >128 | >128 |
| *Acinetobacter* (Moraxellaceae Gram−) | | | | | | | | | |
| Acinetobacter baumanii ATCC 19606 | >128 | | >128 | >128 | >128 | >128 | >128(>32) | >128 | >128 |

TABLE I-1-continued

| Haemophilus (Pasteurellaceae Gram−) | | | | | | | | |
|---|---|---|---|---|---|---|---|---|
| Haemophilus influenzae ATCC 49766 | — | >128 | >128 | >128 | >128 | | >128 | >128 |

| Compounds | 11 | 12 | 13 | 14 | 15 | 16 |
|---|---|---|---|---|---|---|
| Staphylococcus (Micrococcaceae Gram+) | | | | | | |
| S. aureus ATCC 25923 | 4 | >32 | 4 | 32 | 32 | 8 |
| S. aureus ATCC 29213 | 4 | >32 | 4 | 32 | 16 | 8 |
| S. aureus ATCC 9144 | 4 | >32 | 4 | 32 | 32 | 8 |
| S. aureus ATCC 6538 | 4 | >32 | 4 | 32 | 16 | 8 |
| S. aureus CIP 65.6 | 4 | >32 | 4 | >32 | 32 | 8 |
| S. aureus CIP 103428 | 4 | >32 | 4 | 32 | 16 | 8 |
| S. aureus CIP 65.25 (MRSA) | 4 | >32 | 4 | 32 | 32 | 8 |
| S. aureus ATCC 33592 (MRSA) | 4 | >32 | 4 | 32 | 32 | 8 |
| S. aureus ATCC 106414 (VISA) | 4 | >32 | 4 | 32 | 32 | 8 |
| S. epidermidis ATCC 12228 | 4 | >32 | 4 | 32 | 32 | 8 |
| S. epidermidis CIP 81.55 | 4 | >32 | 4 | 32 | >32 | 8 |
| S. epidermidis CIP 103627 | 4 | >32 | 4 | 32 | 32 | 8 |
| S. aureus SA-1199B | 4 | >32 | 8 | — | — | — |
| Streptococcus and Enterococcus (Streptococcaceae Gram+) | | | | | | |
| S. pneumoniae ATCC 49619 | — | — | — | 64 | 128 | >128 |
| S. pneumoniae ATCC 6303 | — | — | — | 128 | 128 | >128 |
| S. agalactiae (group B) ATCC 12400 | — | — | — | 64 | 64 | >128 |
| S. pyogenes (group A) CIP 104226 | — | — | — | 64 | 128 | >128 |
| S. mitis CIP 103335 | — | — | — | >128 | >128 | >128 |
| E. faecium CIP 54.32 | — | — | — | >128 | >128 | >128 |
| E. faecalis ATCC 29212 | — | — | — | >128 | >128 | >128 |
| Listeria (Listeriaceae Gram+) | | | | | | |
| Listeria innocua CIP 80.11 | — | — | — | >128 | >128 | >128 |
| Bacillus (Bacillaceae Gram+) | | | | | | |
| Bacillus subtilis CIP 5262 | — | — | — | >128 | >128 | >128 |
| Enterobacteriaceae (Gram−) | | | | | | |
| Escherichia coli ATCC 25922 | — | — | — | >32 | >32 | 16 |
| Klebsiella pneumoniae API ATCC 35657 | — | — | — | >32 | >32 | >32 |
| Enterobacter cloacae API Ec10 ATCC13047 | — | — | — | >32 | >32 | 16 |
| Serratia marcescens CIP 103551 | — | — | — | >32 | >32 | >32 |
| Pseudomonadaceae (Gram−) | | | | | | |
| Pseudomonas aeruginosa CIP 5933 | — | — | — | >32 | >32 | 32 |
| Acinetobacter (Moraxellaceae Gram−) | | | | | | |
| Acinetobacter baumanii ATCC 19606 | — | — | — | >32 | >32 | >32 |
| Haemophilus (Pasteurellaceae Gram−) | | | | | | |
| Haemophilus influenzae ATCC 49766 | — | — | — | >128 | >128 | >128 |

MRSA: methicillin-resistant *Staphylococcus aureus*
VISA: vancomycin intermediate *Staphylococcus aureus*

9.2: Determination of the Minimum Inhibitory Concentration (MIC) of Compounds 3f and 4 Against a Large Panel of *Staphylococcus* Sp. Strains The MIC of compounds 3f and 4 in Table II-2 (see below) were determined against a large panel of *Staphylococcus* strains, using subttle modifications of the previous protocol, as described below:

The microdilution method recommended by the Clinical and Laboratory Standard Institute [M07-A9, Vol. 32, N° 2] was used. The activity of bis-indolic compounds 3f and 4 was tested against 35 *Staphylococcus* bacterial strains corresponding to 12 different species, Bacterial inocula were prepared in Mueller Hinton broth (MH2, BioMérieux, Marcy L'Etoile, France). They were dispensed in 96 well microtiter plates ($5 \times 10^5$ CFU/ml of final inoculum, 192 µL per well). Indolic compounds diluted in pure DMSO (8 µL per well, concentrated 25 times) were added to the wells as to obtain two-fold serial concentrations (0.5-32 mg/L of final concentrations). The final concentration of DMSO was 4% in each well.

To avoid cross-contaminations in microtiter plates, one row was left blank between each strain tested. Microplates were incubated for 18 h at 37° C. in ambient air. Then MICs were read visually and, in case of visual reading difficulties, confirmed using a spectrophotometer at a wavelength of 630 nm (BioTek® EL808 Absorbance Microplate Reader). MICs corresponded to the minimum bis-indolic compound concentration that allowed complete visual growth inhibition of bacteria. Drug-free cultures served as growth controls.

Bacterial Strains

Four *Staphylococcus aureus* strains were used. Two reference strains were provided by the French reference center for *Staphylococcus* spp. (Lyon, France), including one methicillin-susceptible (MSSA 476) and one methicillin-resistant (MRSA 252) *S. aureus* strains. The two remaining *S. aureus* strains were purchased from the CRBIP (Centre de Ressources Biologiques de l'Institut Pasteur): a vancomycin-intermediate strain (ATCC 106414) and a *S. aureus* strain (SA-1199B) resistant to fluoroquinolones due to overexpression of the NorA multidrug efflux pump.

Coagulase-negative *Staphylococcus* strains included three reference strains purchased from CRBIP: a methicillin-susceptible *S. epidermidis* strain (ATCC 12228), a methicillin-resistant *S. epidermidis* strain (ATCC 49461), and a methicillin-susceptible *S. sciuri* strain (ATCC 29061). We also used clinical strains belonging to the following coagulase-negative *Staphylococcus* species: *S. auricularis* (two strains), *S. warneri* (five strains), *S. capitis* (five strains), *S. haemolyticus* (four strains), *S. hominis* (seven strains), *S. cohnii* (two strains), and *S. saprophyticus, S. caprae* and *S. simulans* (one strain each). Identification of the clinical strains was obtained using VITEK® 2 System (Biomérieux). The specified strain numbers correspond to an internal number of the bacterial strain collection of our laboratory.

The results are presented in Table II-2 below:

TABLE II-2

| *Staphylococcus* (Micrococcaceae Gram+) | Compounds | |
|---|---|---|
| | 3f | 4 |
| *Staphylococcus aureus* ATCC 106414 (VISA) | 2 | 1 |
| *Staphylococcus aureus* MRSA 252 | 2 | 2 |
| *Staphylococcus aureus* MSSA 476 | 2 | 1 |
| *Staphylococcus aureus* SA-1199B (NorA) | 2 | 2 |
| *Staphylococcus auricularis* (CHUG-Saur1) | 2 | 1 |
| *Staphylococcus auricularis* (CHUG-Saur3) | 8 | — |
| *Staphylococcus capitis* (CHUG-Scap1) | 4 | 2 |
| *Staphylococcus capitis* (CHUG-Scap5) | 16 | — |
| *Staphylococcus capitis* (CHUG-Scap4) | 4 | — |
| *Staphylococcus capitis* (CHUG-Scap6) | 8 | — |
| *Staphylococcus capitis* (CHUG-Scap7) | 16 | — |
| *Staphylococcus caprae* (CHUG-Scapra1) | 8 | — |
| *Staphylococcus cohnii* (CHUG-Scoh1) (MRSA) | 16 | — |
| *Staphylococcus cohnii* (CHUG-Scoh2) | 16 | — |
| *Staphylococcus epidermidis* ATCC 12228 | 2 | 1 |
| *Staphylococcus epidermidis* ATCC 49461 | 2 | 1 |
| *Staphylococcus haemolyticus* (CHUG-Shae1) | 4 | 2 |
| *Staphylococcus haemolyticus* (CHUG-Shae5) | 16 | — |
| *Staphylococcus haemolyticus* (CHUG-Shae4) | 16 | — |
| *Staphylococcus haemolyticus* (CHUG-Shae6) | 16 | — |
| *Staphylococcus hominis* (CHUG-Shom1) | 4 | 1 |
| *Staphylococcus hominis* (CHUG-Shom6) | 8 | — |
| *Staphylococcus hominis* (CHUG-Shom4) | 8 | — |
| *Staphylococcus hominis* (CHUG-Shom7) | 8 | — |
| *Staphylococcus hominis* (CHUG-Shom5) | 8 | — |
| *Staphylococcus hominis* (CHUG-Shom3) | 16 | — |
| *Staphylococcus hominis* (CHUG-Shom8) | 8 | — |
| *Staphylococcus saprophyticus* (CHUG-Ssap2) | 8 | — |
| *Staphylococcus sciuri* ATCC 29061 | 4 | 2 |
| *Staphylococcus simulans* (CHUG-Ssim1) | 16 | — |
| *Staphylococcus warneri* (CHUG-Swar1) | 2 | 1 |
| *Staphylococcus warneri* (CHUG-Swar5) | 8 | — |
| *Staphylococcus warneri* (CHUG-Swar4) | 8 | — |
| *Staphylococcus warneri* (CHUG-Swar6) | 8 | — |
| *Staphylococcus warneri* (CHUG-Swar7) | 8 | — |

MRSA: methicillin-resistant *Staphylococcus aureus*
VISA: vancomycin intermediate *Staphylococcus aureus*
NorA: overexpression of NorA efflux pump

9.2: Determination of the Minimum Bactericidal Concentration (MBC)

The MBC was determined using a macro-method. Sterile tubes were filled with a primary bacterial inoculum prepared in Mueller Hinton broth as above ($10^6$ CFU/mL of final inoculum) and indolic compounds were added at twofold serial concentrations (0.25-64 mg/L of final concentrations). After 18 hours incubation of cultures, ten-fold serial dilutions of the cultures with no visible bacterial growth were prepared, and 100 μL of each dilution were inoculated to Mueller Hinton agar media for 24-48 hours. CFU counts were then determined and the MBC corresponded to the minimal indolic compound concentration for which 99.9% of more bacterial cells were killed after 18 hours of incubation.

Using compounds 3f and 4, we found a reduction of the primary bacterial inoculum, whereas a significant bacterial growth was observed in drug-free controls. However, this reduction was only 1-2 log CFU/mL, and thus MBC could not be determined.

9.3: Determination of Killing Curves

The method described by Motyl et al. [M. Motyl, K. Dorso, J. Barrett, R. Giacobbe, Basic Microbiological Techniques Used in Antibacterial Drug Discovery. *Current Protocols in Pharmacology*. UNIT 13A.3. January, 2006] was used.

Killing curves corresponded to the measure of the kinetic of bactericidal activity of indolic compounds over time (time-kill curves) or after 18 h incubation of cultures according to different drug concentrations (concentration-killing curves). Sterile tubes were inoculated with: 1/sterile Mueller Hinton broth, to serve as negative control; 2/a drug-free bacterial inoculum, to serve as a growth control; 3/a bacterial inoculum ($10^5$ CFU/mL of final concentration) with various concentrations of the tested indolic compound. The tubes were incubated at 37° C. with agitation (50 rpm). Bacterial inocula are determined in each tube using the CFU count method at the beginning of the experiments, and then after 18 h for concentration-killing curves, or after 1 h, 2 h, 4 h, 8 h and 18 h for time-kill curves. A significant bactericidal effect corresponds to reduction of the initial bacterial load of 3 logs or more at any time of incubation.

9.4: Determination of the Mutation Frequency

The mutation frequency is the number of individuals in a population with a particular mutation. In the present case, the mutation frequency was determined for a specific bacterial species and a specific indolic compound. Mueller Hinton agar plates containing various indolic compound concentrations, i.e., MIC×2, MIC×4, MIC×8, and MIC×16 were prepared. These plates were inoculated with various bacterial suspensions: $10^7$, $10^8$ or $10^9$ UFC/mL. After 24 hours incubation of media at 37° C., CFU were numerated. The mutation frequency corresponded to the ratio of resistant mutants counted on a specific plate to the CFU count of the primary inoculum, expressed as a percentage.

The mutation frequency was determined for *S. aureus* ATCC 25923 strain, and for compounds 3f, 4 and 19. We found the following results: $2\times10^{-9}$, $<1.5\times10^{-10}$ and $8\times10^{-9}$, for the compounds 3f, 4 and 19, respectively. Thus, very low mutation frequencies leading to resistance of *S. aureus* ATCC 25923 to any of these three indolic compounds were found experimentally. These mutations are close to those observed for *S. aureus* and the penicillin M compounds (methicillin, oxacillin), i.e., $\sim10^{-9}$.

9.5: In Vitro Selection of Resistant Mutants

In vitro mutant strains that resisted to the most active indolic compounds were selected. A bacterial inoculum ($5\times10^4$ CFU/mL) was prepared in Mueller Hinton broth and dispensed in a 24-well microtiter plate (1 ml per well). Each row received two-fold serial concentrations of the tested indolic compound (½ to 16 times the MIC of the wild-type strain). Plates were incubated 72-96 hours, and bacterial growth obtained in the well with the highest indolic compound concentration were harvested, diluted 1/40 and dispensed in a new 24-well microtiter plate with increased drug concentrations (½ to 16 times the new MIC). The procedure was repeated several fold until we obtained high-level resistant mutants. The final and intermediate resistant mutant populations were all kept frozen at −80° C. for later analysis.

Several independent mutant strains with acquired resistance to indolic compounds in *S. aureus* and in *S. epidermidis* strains have been selected. Selection of resistance was slow and difficult to obtain, but high-level resistant mutants (MIC of 64-128 mg/L) could be isolated. These mutants have been used to better characterize the mode of action of indolic compounds and resistance mechanisms that may be developed by *Staphylococcus* species to resist the action of these new antibiotics.

9.6: Determination of Antibacterial Activity as Efflux Pump Inhibition

The efflux pump inhibition potential of the bis-indolic derivatives was tested using two steps.

In a first step, the intrinsic antibacterial activity of the compounds was assayed against the following strains:

*Staphylococcus aureus* (ATCC 25923), *Staphylococcus aureus* 1199B, which is resistant to fluoroquinolones due notably to the overexpression of the NorA efflux pump (G. W. Kaatz, S. M. Seo, *Antimicrob. Agents Chemother.* 1995, 39, 2650-2655) and *Staphylococcus aureus* K2378 which overexpresses the efflux pump NorA from a multicopy plasmid (S. Sabatini, G. W. Kaatz, G. M. Rossolini, D. Brandini, A. Fravolini *J. Med. Chem.* 2008, 51, 4321-4330).

The following experimental protocol was used: indolic derivatives (initially solubilised in DMSO at 10 mg/mL) were dispensed in a 96-wells microplate by two fold serial dilutions in Muller-Hinton medium (MH, Bio Rad) using a Biomek 2000 (Beckman) handling robot. 100 µL of the bacterial inoculum (an overnight culture at 37° C. in 5 mL MH diluted 100-fold) was then added in each well. The total volume was 200 µL in each well and the final bacteria concentration $10^6$ CFU/mL (CFU: colony forming unit). The highest final indolic derivative concentration was 128 mg/L. Growth was assayed with a microplate reader by monitoring absorption at 620 nm after 1, 2, 5, 7 and 24 h incubation at 37° C. In addition, the plates were read visually after 24 hours incubation. Cultures containing 5 µL DMSO were used as growth controls. In addition, two controls containing a sub-inhibitory or a inhibitory antibiotic concentration for the tested strain were performed. The antibiotics used were ampicillin (0.5 and 32 µg/mL) for *E. coli*, kanamycin (0.5 and 16 µg/mL) for *S. aureus* ATCC 25923, ciprofloxacin (4 and 64 mg/L) for *S. aureus* 1199B, ciprofloxacin (0.5 and 2 mg/L) for *S. aureus* K2378. All experiments were performed in duplicate.

In spite of slight differences in the experimental protocol, all compounds described in the present invention showed similar antibacterial activity (at most a 4-fold difference was observed between MIC values) using the experimental procedure described in paragraph 9.1 and in the present paragraph).

Efflux pump inhibition assays were then performed against resistant *Staphylococcus aureus* strains SA 1199B and SA K2378 for bis-indolic derivatives. A serial dilution method was used to test the bis-indolic compounds (maximal concentration 128 mg/L) in the presence of a sub-inhibitory concentration of the ciprofloxacin (4 mg/L, MIC/8) or less for SA 1199B and ciprofloxacin (0.5 mg/L, MIC/4) for SA K2378. The minimal inhibitory concentration (MIC) of the bis-indolic compound allowing a complete inhibition of the bacterial growth in the presence of ciprofloxacin was determined.

Results are presented in table III:

TABLE III

| | MIC, mg/L (Ciprofloxacin concentration, mg/L) | |
| --- | --- | --- |
| Compounds | *Staphylococcus aureus* 1199B | *Staphylococcus aureus* K2378 |
| 3a | 0.25 (4) | 4 (0.5) |
| | 0.5 (2) | |
| | 2 (1) | |
| 7 | 0.25 (4) | 0.125 (0.5) |
| | 1 (2) | |
| | 4 (1) | |
| 12 | 64 (4) | 64 (0.5) |
| | 32 (2) | |
| 16 | 1 (4) | — |

Some compounds of the invention showing no intrinsic antibacterial activity (MIC>128 mg/L) against *S. aureus* ATCC 25923 and/or *S. aureus* 1199B according to the above described experiments present a strong activity as NorA pump efflux inhibitor, as shown against *Staphylococcus aureus* 1199B, a fluoroquinolone resistant strain overexpressing NorA and confirmed against *Staphylococcus aureus* K2378 which overexpresses the efflux pump NorA from a multicopy plasmid as a unique resistance mechanism. Some compounds, as exemplified with compound 16, show an intrinsic antibacterial activity when used alone (MIC 8 mg/L for compound 16 against *Staphylococcus aureus* ATCC 25923) and a reduced MIC in presence of ciprofloxacin, which could result from an additive or synergistic effect with ciprofloxacin or from a distinct activity as a pump efflux inhibitor.

9.7 Cytotoxicity Determination of the Compound of the Invention

In vitro cytotoxicity was assayed on three cell lines—KB (human mouth carcinoma), MCR5 (human lung fibroblast) and HCT116 (human colon tumor). Results are presented in table IV as % of cellular growth inhibition in presence of $10^{-5}$ M and $10^{-6}$ M of the tested bis-indolic derivatives.

$IC_{50}$ are presented in table V.

TABLE IV

| Compounds | KB $10^{-5}$M ($10^{-6}$M) | MRC5 $10^{-5}$M (10–6M) | HCT116 10–5M ($10^{-6}$M) |
| --- | --- | --- | --- |
| 3a | 18 ± 1 (16 ± 1) | 14 ± 1 (2 ± 7) | 22 ± 5 (11 ± 2) |
| 3b | 41 ± 6 (0 ± 4) | 8 ± 5 (7 ± 4) | 30 ± 2 (0 ± 9) |
| 3c | 46 ± 8 (0 ± 16) | 16 ± 9 (0 ± 5) | 42 ± 3 (11 ± 2) |
| 3d | 67 ± 3 (0 ± 9) | 73 ± 6 (0 ± 1) | 73 ± 3 (9 ± 5) |
| 3e | 99 ± 1 (0 ± 22) | 92 ± 6 (0 ± 9) | 92 ± 1 (2 ± 5) |
| 3f | 97 ± 1 (0 ± 5) | 91 ± 10 (0 ± 8) | 89 ± 9 (0 ± 9) |
| 3g | 98 ± 1 (0 ± 10) | 83 ± 10 (0 ± 6) | 86 ± 2 (9 ± 4) |
| 3h | 100 ± 1 (0 ± 3) | 92 ± 1 (0 ± 16) | 100 ± 3 (0 ± 1) |
| 3i | 100 ± 1 (3 ± 1) | 91 ± 7 (10 ± 5) | 91 ± 1 (4 ± 7) |
| 4 | 13 ± 3 (0 ± 5) | 36 ± 4 (7 ± 4) | 12 ± 1 (0 ± 3) |
| 5 | ND | ND | ND |
| 6a | 87 ± 6 (4 ± 8) | 82 ± 4 (0 ± 9) | 80 ± 9 (0 ± 5) |
| 6b | 92 ± 4 (2 ± 4) | 99 ± 1 (0 ± 3) | 97 ± 6 (0 ± 4) |
| 7 | 52 ± 2 (2 ± 7) | 23 ± 6 (12 ± 3) | 35 ± 3 (8 ± 3) |

TABLE IV-continued
| Compounds | KB 10⁻⁵M (10⁻⁶M) | MRC5 10⁻⁵M (10⁻⁶M) | HCT116 10⁻⁵M (10⁻⁶M) |
|---|---|---|---|
| 11 | 51 ± 1 (0 ± 2) | 28 ± 9 (0 ± 1) | 51 ± 5 (0 ± 5) |
| 12 | 0 ± 1 (0 ± 4) | 3 ± 3 (3 ± 2) | 0 ± 4 (0 ± 2) |
| 13 | 1 ± 4 (0 ± 3) | 6 ± 1 (0 ± 2) | 12 ± 5 (0 ± 5) |
TABLE V
IC$_{50}$ from 100 μM to 0.005 μM on HCT116 in DMSO (duplicate)
| Compounds | HCT116 IC$_{50}$ |
|---|---|
| 3b | 15.0/11.2 |
| 3c | 8.02/5.43 |
| 3f | 5.24/5.05 |
| 3g | 5.48/6.06 |
| 3h | 3.33/4.11 |
| 3i | 1.90/2.10 |
| 4 | 6.43/10.04 |
| 6a | 4.35/3.79 |
| 7 | 10.1/13.1 |
| 8 | 6.14/7.33 |
| 16 | 52.9/42.8 |
| — | — |
The invention claimed is:
1. A product comprising a compound selected from the group consisting of:
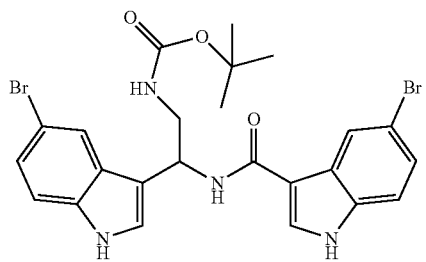
Compound 3f
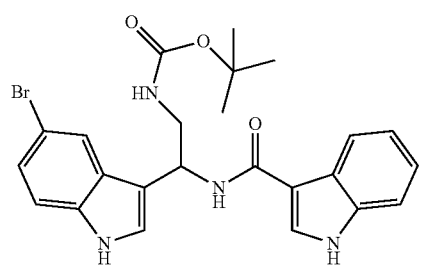
Compound 3b
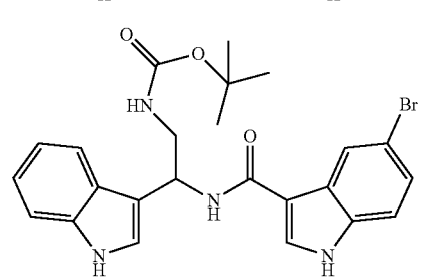
Compound 3c
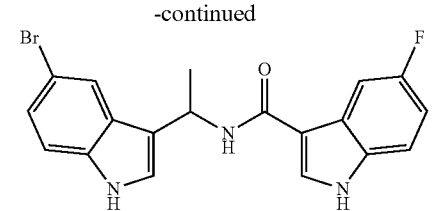
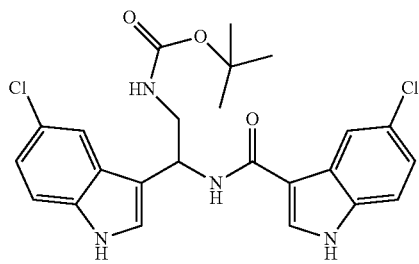
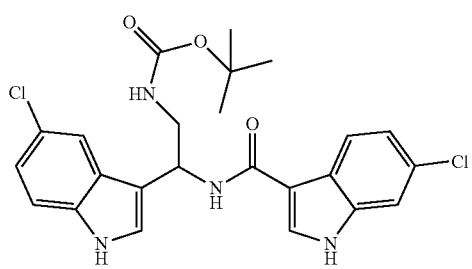
Compound 4
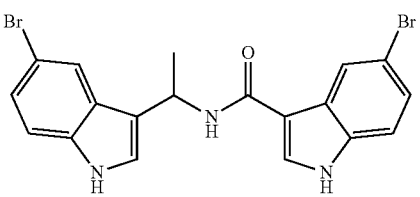
Compound 12
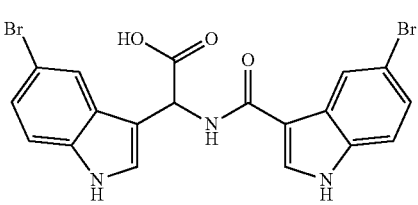
Compound 11
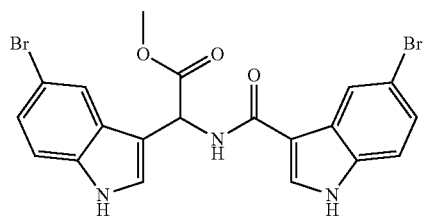
Compound 13
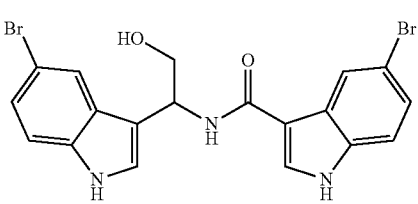

Compound 14
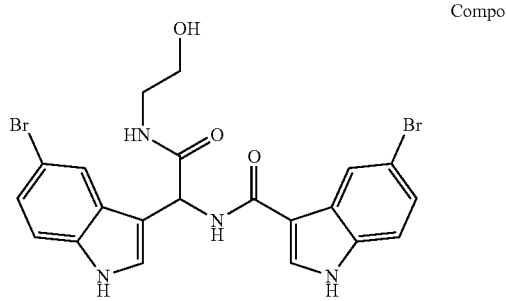
Compound 15
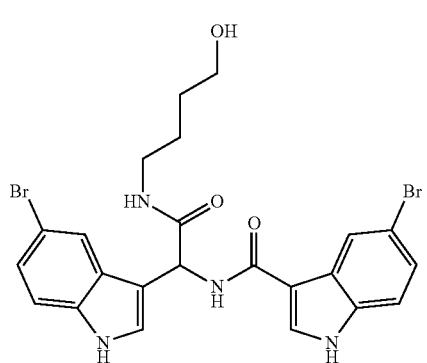
Compound 16
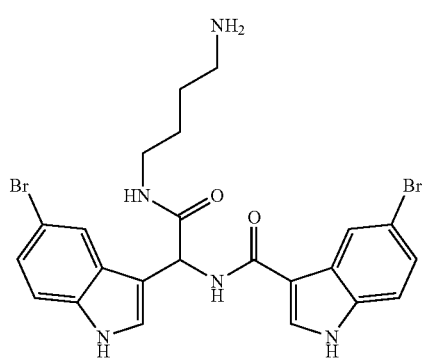
Compound 3i
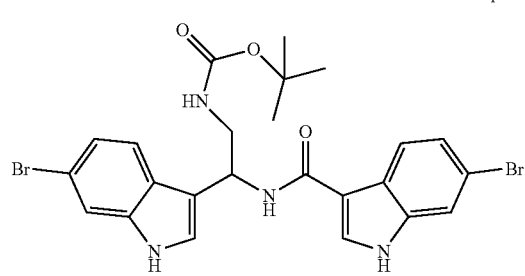
Compound 3d
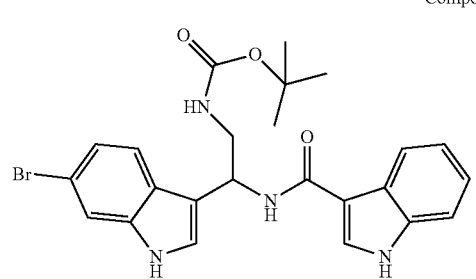
Compound 3e
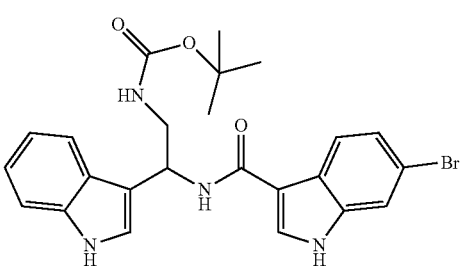
Compound 3g
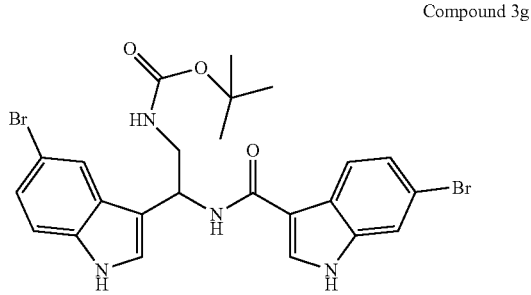
Compound 3h
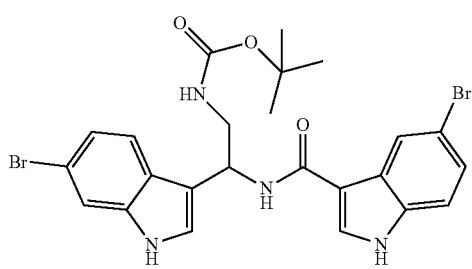
Compound 7
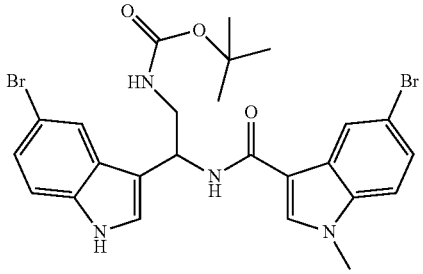
Composé 3a
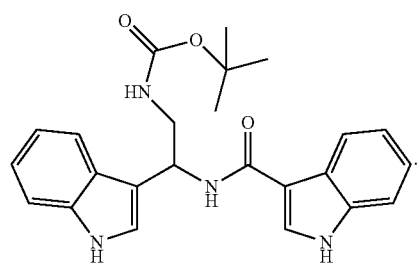
2. A pharmaceutical composition, comprising:
a compound having a general formula selected from the group consisting of:

general formula VI:

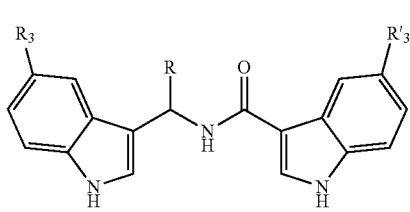

wherein:
$R_3$ and $R'_3$ represent independently from each other H, F, Cl, Br, I,
R represents a $(C_1$-$C_7)$-alkyl, $CH_2NHCO_2$ $(C_1$-$C_7)$-alkyl, $(CH_2)_nOH$, $CH_2NH(CH_2)_n$—OH, $CH_2NH(CH_2)_n$—$NR_aR_b$, $CO_2H$, $CO_2$—$(C_1$-$C_7)$-alkyl, CONH—$(CH_2)_nOH$, CONH—$(CH_2)_nNR_aR_b$, wherein $R_a$ and $R_b$ represents H, a linear or branched $(C_1$-$C_7)$-alkyl, a $(C_3$-$C_7)$-cycloalkyl, an aryl substituted or not, $CH_2$-aryl, CO—$(C_1$-$C_7)$-alkyl, CO-aryl, $CO_2$—$(C_1$-$C_7)$-alkyl, $CO_2$-aryl, wherein aryl is a substituted or not aromatic group or a substituted or not heteroaromatic group and n=2 to 12;

general formula VII:

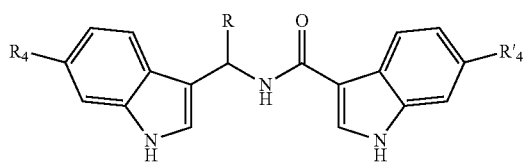

wherein:
$R_4$ and $R'_4$ represent independently from each other H, F, Cl, Br, I,
R represents a $(C_1$-$C_7)$-alkyl, $CH_2NHCO_2$ $(C_1$-$C_7)$-alkyl, $(CH_2)_nOH$, $CH_2NH(CH_2)_n$—OH, $CH_2NH(CH_2)_n$—$NR_aR_b$, $CO_2H$, $CO_2$—$(C_1$-$C_7)$-alkyl, CONH—$(CH_2)_nOH$, CONH—$(CH_2)_nNR_aR_b$ wherein $R_a$, $R_b$, and n being as defined above;

general formula VIII:

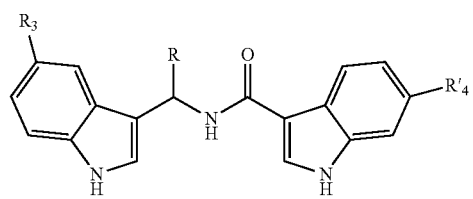

wherein:
$R_3$ and $R'_4$ represent independently from each other F, Cl, Br, I,
R represents a $(C_1$-$C_7)$-alkyl, $CH_2NHCO_2$ $(C_1$-$C_7)$-alkyl, $(CH_2)_nOH$, $CH_2NH(CH_2)_n$—OH, $CH_2NH(CH_2)_n$—$NR_aR_b$, $CO_2H$, $CO_2$—$(C_1$-$C_7)$-alkyl, CONH—$(CH_2)_nOH$, CONH—$(CH_2)_nNR_aR_b$ wherein $R_a$, $R_b$, and n being as defined above;

general formula IX:

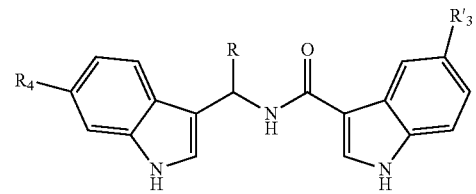

wherein:
$R_4$ and $R'_3$ represent independently from each other F, Cl, Br, I,
R represents a $(C_1$-$C_7)$-alkyl, $CH_2NHCO_2$ $(C_1$-$C_7)$-alkyl, $CO_2H$, $(CH_2)_nOH$, $CH_2NH(CH_2)_n$—OH, $CH_2NH(CH_2)_n$—$NR_aR_b$, $CO_2$—$(C_1$-$C_7)$-alkyl, CONH—$(CH_2)_nOH$, CONH—$(CH_2)_nNR_aR_b$ wherein $R_a$, $R_b$, and n being as defined above;

general formula X:

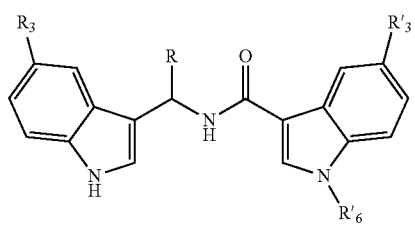

wherein:
$R_3$ and $R'_3$ represent independently from each other F, Cl, Br, I,
R represents a $(C_1$-$C_7)$-alkyl, $CH_2NHCO_2$ $(C_1$-$C_7)$-alkyl, $(CH_2)_nOH$, $CH_2NH(CH_2)_n$—OH, $CH_2NH(CH_2)_n$—$NR_aR_b$, $CO_2H$, $CO_2$—$(C_1$-$C_7)$-alkyl, CONH—$(CH_2)_nOH$, CONH—$(CH_2)_nNR_aR_b$,
$R'_6$ represents a $(C_1$-$C_7)$-alkyl wherein $R_a$, $R_b$, and n being as defined above; and general formula XI:

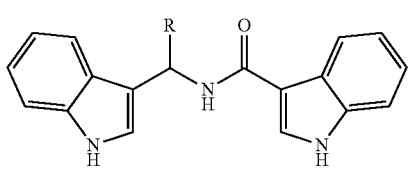

wherein:
R represents a $(C_1$-$C_7)$-alkyl, $CH_2NHCO_2(C_1$-$C_7)$-alkyl; and
a pharmaceutically acceptable vehicle.

3. A pharmaceutical composition, comprising:
a compound selected from the group consisting of:
Compound 3i
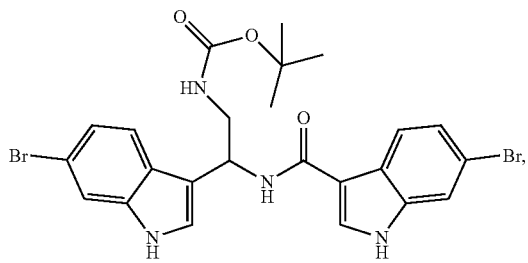
Compound 3d
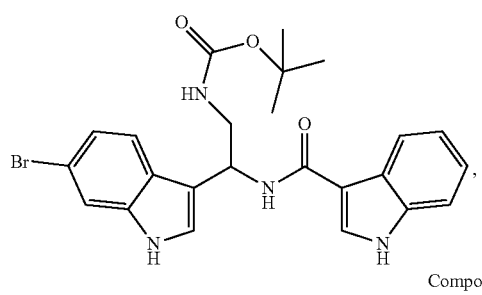
Compound 3e
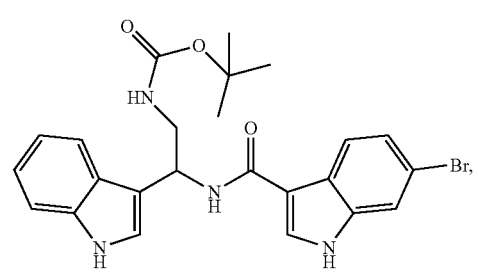
Compound 3g
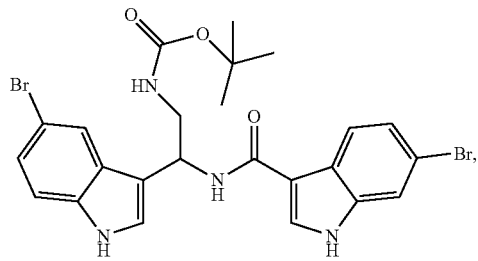
Compound 3h
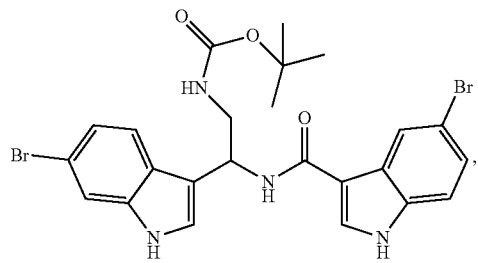
-continued
Compound 7
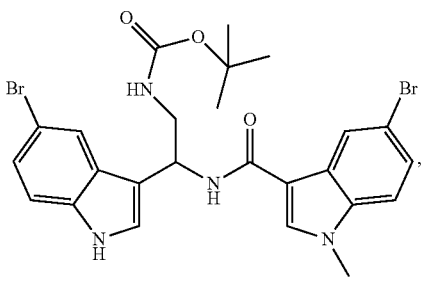
Compound 3a
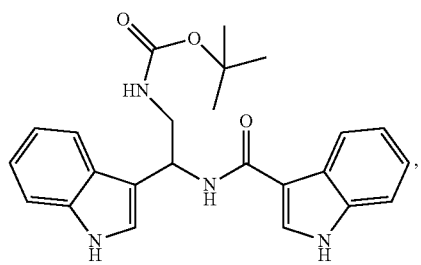
Compound 6b
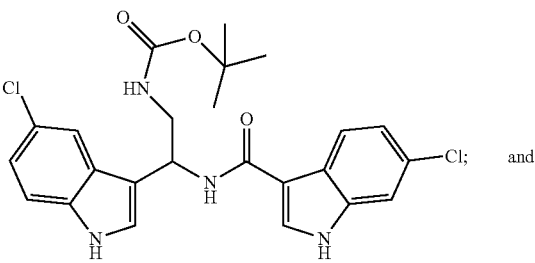
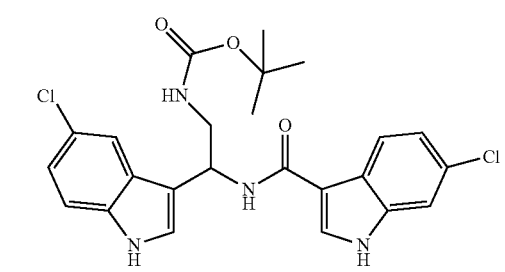 [SMILES: CC(C)(C)OC(=O)NCC(NC(=O)c1c[nH]c2cc(Cl)ccc12)c1c[nH]c2ccc(Cl)cc12]
a pharmaceutically acceptable vehicle.
* * * * *